United States Patent
Michaud et al.

(10) Patent No.: US 11,305,057 B2
(45) Date of Patent: Apr. 19, 2022

(54) METHOD AND SYSTEM OF OPERATING AN INFUSION PUMP WITH A REMOTE CONTROL DEVICE

(71) Applicant: Tandem Diabetes Care, Inc., San Diego, CA (US)

(72) Inventors: Michael Michaud, San Diego, CA (US); Geoffrey A. Kruse, San Diego, CA (US); Jason Farnan, San Diego, CA (US); Ian Cadieux, San Diego, CA (US); Anthony Elbancol, San Diego, CA (US); Preston Sobel, San Diego, CA (US); David Nguyen, San Diego, CA (US); Robert Eastridge, San Diego, CA (US); Kennen Dietz, San Diego, CA (US); Caleb Butler, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 249 days.

(21) Appl. No.: 16/830,415

(22) Filed: Mar. 26, 2020

(65) Prior Publication Data

US 2020/0306445 A1 Oct. 1, 2020

Related U.S. Application Data

(60) Provisional application No. 62/823,991, filed on Mar. 26, 2019.

(51) Int. Cl.
*A61M 5/142* (2006.01)
*G08B 21/00* (2006.01)
(Continued)

(52) U.S. Cl.
CPC ......... *A61M 5/14248* (2013.01); *G08B 21/00* (2013.01); *G16H 20/17* (2018.01);
(Continued)

(58) Field of Classification Search
CPC ... A61M 5/14248; G16H 20/17; G16H 40/67; G08B 21/00
(Continued)

(56) References Cited

U.S. PATENT DOCUMENTS

| RE28,890 E | 7/1976 | Ingram et al. |
| 4,624,661 A | 11/1986 | Arimond |

(Continued)

FOREIGN PATENT DOCUMENTS

| EP | 2624745 A2 | 8/2013 |
| WO | WO-2005018507 A2 | 3/2005 |

(Continued)

OTHER PUBLICATIONS

Application and File history for U.S. Appl. No. 16/507,146, filed Jul. 10, 2019, Inventors Farnan et al.
(Continued)

*Primary Examiner* — Kerri L McNally
(74) *Attorney, Agent, or Firm* — Patterson Thuente Pedersen, P.A.

(57) ABSTRACT

Embodiments of the present disclosure enable a user-wearable infusion pump that may have a limited user interface including no display to execute and provide feedback on a number of functions. A remote control device having a display can be used to control the infusion pump. The infusion pump can include one or more indicator lights that can be indicate different statuses with different light patterns. The remote control device can include a display screen that provides further information relating to various pump statuses.

20 Claims, 67 Drawing Sheets

(51) Int. Cl.
*G16H 20/17* (2018.01)
*G16H 40/67* (2018.01)

(52) U.S. Cl.
CPC ......... *G16H 40/67* (2018.01); *A61M 2205/18* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/583* (2013.01); *A61M 2205/584* (2013.01); *A61M 2205/587* (2013.01); *A61M 2205/8206* (2013.01); *A61M 2205/8243* (2013.01)

(58) Field of Classification Search
USPC .................................................. 340/539.12
See application file for complete search history.

(56) References Cited

U.S. PATENT DOCUMENTS

| | | | |
|---|---|---|---|
| 4,678,460 | A | 7/1987 | Rosner |
| 5,000,739 | A | 3/1991 | Kulisz et al. |
| 5,558,638 | A | 9/1996 | Evers et al. |
| 5,578,832 | A | 11/1996 | Trulson et al. |
| 5,582,593 | A | 12/1996 | Hultman |
| 5,593,552 | A | 1/1997 | Joshi et al. |
| 5,704,366 | A | 1/1998 | Tacklind et al. |
| 5,860,957 | A | 1/1999 | Jacobsen et al. |
| 5,954,752 | A | 9/1999 | Mongeon et al. |
| 6,013,020 | A | 1/2000 | Meloul et al. |
| 6,017,318 | A | 1/2000 | Gauthier et al. |
| 6,070,761 | A | 6/2000 | Bloom et al. |
| 6,144,866 | A | 11/2000 | Miesel et al. |
| 6,165,155 | A | 12/2000 | Jacobsen et al. |
| 6,185,460 | B1 | 2/2001 | Thompson |
| 6,223,080 | B1 | 4/2001 | Thompson |
| 6,238,423 | B1 | 5/2001 | Bardy |
| 6,398,718 | B1 | 6/2002 | Yachia et al. |
| 6,402,689 | B1 | 6/2002 | Scarantino et al. |
| 6,488,652 | B1 | 12/2002 | Weijand et al. |
| 6,514,689 | B2 | 2/2003 | Han et al. |
| 6,561,978 | B1 | 5/2003 | Conn et al. |
| 6,564,104 | B2 | 5/2003 | Nelson et al. |
| 6,594,634 | B1 | 7/2003 | Hampton et al. |
| 6,610,003 | B1 | 8/2003 | Meloul et al. |
| 6,649,403 | B1 | 11/2003 | McDevitt et al. |
| 6,656,159 | B2 | 12/2003 | Flaherty |
| 6,683,690 | B1 | 1/2004 | Tobias |
| 6,740,059 | B2 | 5/2004 | Flaherty |
| 6,804,555 | B2 | 10/2004 | Warkentin |
| 6,821,249 | B2 | 11/2004 | Casscells, III et al. |
| 6,827,524 | B2 | 12/2004 | Starry, Jr. et al. |
| 6,857,572 | B2 | 2/2005 | Martin |
| 6,864,101 | B1 | 3/2005 | Winkler et al. |
| 6,916,159 | B2 | 7/2005 | Rush et al. |
| 6,943,034 | B1 | 9/2005 | Winkler et al. |
| 6,960,192 | B1 | 11/2005 | Flaherty et al. |
| 6,963,770 | B2 | 11/2005 | Scarantino et al. |
| 6,970,742 | B2 | 11/2005 | Mann et al. |
| 7,010,340 | B2 | 3/2006 | Scarantino et al. |
| 7,011,630 | B2 | 3/2006 | Desai et al. |
| 7,025,716 | B1 | 4/2006 | Meloul et al. |
| 7,029,455 | B2 | 4/2006 | Flaherty |
| 7,053,761 | B2 | 5/2006 | Schofield et al. |
| 7,070,577 | B1 | 7/2006 | Haller et al. |
| 7,089,608 | B2 | 8/2006 | Erb |
| 7,137,964 | B2 | 11/2006 | Flaherty |
| 7,144,384 | B2 | 12/2006 | Gorman et al. |
| 7,181,505 | B2 | 2/2007 | Haller et al. |
| 7,193,521 | B2 | 3/2007 | Moberg et al. |
| 7,198,603 | B2 | 4/2007 | Penner et al. |
| 7,204,823 | B2 | 4/2007 | Estes et al. |
| 7,291,107 | B2 | 11/2007 | Hellwig et al. |
| 7,303,549 | B2 | 12/2007 | Flaherty et al. |
| 7,316,899 | B2 | 1/2008 | McDevitt et al. |
| 7,366,925 | B2 | 4/2008 | Keely et al. |
| 7,385,443 | B1 | 6/2008 | Denison |
| 7,399,401 | B2 | 7/2008 | Rush |
| 7,483,743 | B2 | 1/2009 | Mann et al. |
| 7,497,827 | B2 | 3/2009 | Brister et al. |
| 7,553,281 | B2 | 6/2009 | Hellwig et al. |
| 7,558,629 | B2 | 7/2009 | Keimel et al. |
| 7,604,593 | B2 | 10/2009 | Parris et al. |
| 7,605,710 | B2 | 10/2009 | Crnkovich et al. |
| 7,615,007 | B2 | 11/2009 | Shults et al. |
| 7,625,354 | B2 | 12/2009 | Hochman |
| 7,651,489 | B2 | 1/2010 | Estes et al. |
| 7,651,868 | B2 | 1/2010 | McDevitt et al. |
| 7,654,976 | B2 | 2/2010 | Peterson et al. |
| 7,654,982 | B2 | 2/2010 | Carlisle et al. |
| 7,691,330 | B1 | 4/2010 | Winkler et al. |
| 7,699,775 | B2 | 4/2010 | Desai et al. |
| 7,704,227 | B2 | 4/2010 | Moberg et al. |
| 7,711,402 | B2 | 5/2010 | Shults et al. |
| 7,713,574 | B2 | 5/2010 | Brister et al. |
| 7,714,757 | B2 | 5/2010 | Denison et al. |
| 7,722,536 | B2 | 5/2010 | Goodnow |
| 7,737,581 | B2 | 6/2010 | Spurlin et al. |
| 7,774,145 | B2 | 8/2010 | Brauker et al. |
| 7,775,975 | B2 | 8/2010 | Brister et al. |
| 7,788,369 | B2 | 8/2010 | McAllen et al. |
| 7,811,279 | B2 | 10/2010 | John |
| 7,837,647 | B2 | 11/2010 | Estes et al. |
| 7,850,674 | B2 | 12/2010 | Goodnow et al. |
| 7,933,780 | B2 | 4/2011 | De La Huerga |
| 7,949,382 | B2 | 5/2011 | Jina |
| 7,973,667 | B2 | 7/2011 | Crnkovich et al. |
| 8,005,547 | B2 | 8/2011 | Forsberg et al. |
| 8,012,119 | B2 | 9/2011 | Estes et al. |
| 8,029,443 | B2 | 10/2011 | Goodnow |
| 8,034,019 | B2 | 10/2011 | Nair et al. |
| 8,083,718 | B2 | 12/2011 | Rush et al. |
| 8,095,197 | B2 | 1/2012 | Santini, Jr. et al. |
| 8,100,852 | B2 | 1/2012 | Moberg et al. |
| 8,106,534 | B2 | 1/2012 | Spurlin et al. |
| 8,118,770 | B2 | 2/2012 | Galley et al. |
| 8,121,857 | B2 | 2/2012 | Galasso et al. |
| 8,147,511 | B2 | 4/2012 | Perry et al. |
| 8,226,558 | B2 | 7/2012 | Say et al. |
| 8,234,128 | B2 | 7/2012 | Martucci et al. |
| 8,275,438 | B2 | 9/2012 | Simpson et al. |
| 8,277,416 | B2 | 10/2012 | Gibbs et al. |
| 8,280,476 | B2 | 10/2012 | Jina |
| 8,287,454 | B2 | 10/2012 | Wolpert et al. |
| 8,287,495 | B2 | 10/2012 | Michaud et al. |
| 8,311,749 | B2 | 11/2012 | Brauker et al. |
| 8,323,188 | B2 | 12/2012 | Tran |
| 8,357,091 | B2 | 1/2013 | Say et al. |
| 8,369,919 | B2 | 2/2013 | Kamath et al. |
| 8,372,351 | B2 | 2/2013 | Ow-Wing |
| 8,402,145 | B2 | 3/2013 | Holden et al. |
| 8,414,523 | B2 | 4/2013 | Blomquist et al. |
| 8,414,563 | B2 | 4/2013 | Kamen et al. |
| 8,444,595 | B2 | 5/2013 | Brukalo et al. |
| 8,449,523 | B2 | 5/2013 | Brukalo et al. |
| 8,451,230 | B2 | 5/2013 | Celentano et al. |
| 8,454,557 | B1 | 6/2013 | Qi et al. |
| 8,460,243 | B2 | 6/2013 | Goodnow et al. |
| 8,502,662 | B2 | 8/2013 | Pohlman et al. |
| 8,533,475 | B2 | 9/2013 | Frikart et al. |
| 8,573,027 | B2 | 11/2013 | Rosinko et al. |
| 8,639,288 | B1 | 1/2014 | Friedman |
| 8,726,266 | B2 | 5/2014 | Kiaie et al. |
| 8,932,250 | B2 | 1/2015 | Montgomery et al. |
| 8,986,253 | B2 | 3/2015 | DiPerna |
| 9,008,803 | B2 | 4/2015 | Blomquist |
| 9,049,982 | B2 | 6/2015 | Brukalo et al. |
| 9,132,227 | B2 | 9/2015 | Bryant, Jr. et al. |
| 9,155,900 | B2 | 10/2015 | Meskens |
| 9,173,992 | B2 | 11/2015 | Bengtsson et al. |
| 9,381,297 | B2 | 7/2016 | Brown et al. |
| 9,474,856 | B2 | 10/2016 | Blomquist |
| 9,486,571 | B2 | 11/2016 | Rosinko |
| 9,565,718 | B2 * | 2/2017 | Swanson ............... H04W 88/04 |

(56) References Cited

U.S. PATENT DOCUMENTS

| | | |
|---|---|---|
| 9,675,756 B2 | 6/2017 | Kamen |
| 9,737,656 B2 | 8/2017 | Rosinko |
| 9,750,873 B2 | 9/2017 | Brown et al. |
| 9,970,044 B2 | 5/2018 | Tonks |
| 9,970,893 B2 | 5/2018 | Morgan |
| 9,974,903 B1 | 5/2018 | Davis et al. |
| 9,980,140 B1 | 5/2018 | Spencer et al. |
| 9,993,595 B2 | 6/2018 | Michaud et al. |
| 10,213,547 B2 | 2/2019 | Rosinko |
| 10,279,106 B1 | 5/2019 | Cook et al. |
| 10,279,107 B2 | 5/2019 | Michaud |
| 10,357,603 B2 | 7/2019 | Michaud et al. |
| 10,430,043 B2 | 10/2019 | Rosinko et al. |
| 10,478,551 B2 | 11/2019 | Rosinko |
| 10,492,141 B2 | 11/2019 | Kruse |
| 10,736,037 B2 | 8/2020 | Kruse et al. |
| 10,773,015 B2 | 9/2020 | Blomquist et al. |
| 10,806,851 B2 | 10/2020 | Rosinko |
| 10,864,318 B2 | 12/2020 | Michaud |
| 10,888,655 B2 | 1/2021 | Farnan et al. |
| 10,918,785 B2 | 2/2021 | Rosinko |
| 10,926,025 B2 | 2/2021 | Betts et al. |
| 2001/0027791 A1 | 10/2001 | Wallace et al. |
| 2002/0040208 A1 | 4/2002 | Flaherty et al. |
| 2002/0072733 A1 | 6/2002 | Flaherty |
| 2002/0126036 A1 | 9/2002 | Flaherty et al. |
| 2003/0036683 A1 | 2/2003 | Kehr et al. |
| 2003/0060765 A1 | 3/2003 | Campbell et al. |
| 2003/0114836 A1 | 6/2003 | Estes et al. |
| 2004/0010207 A1 | 1/2004 | Flaherty et al. |
| 2004/0073161 A1 | 4/2004 | Tachibana |
| 2004/0172222 A1 | 9/2004 | Simpson et al. |
| 2004/0260233 A1 | 12/2004 | Garibotto et al. |
| 2005/0060030 A1 | 3/2005 | Lashinski et al. |
| 2005/0085760 A1 | 4/2005 | Ware et al. |
| 2005/0137530 A1 | 6/2005 | Campbell et al. |
| 2005/0171512 A1 | 8/2005 | Flaherty |
| 2005/0228234 A1 | 10/2005 | Yang |
| 2005/0277912 A1 | 12/2005 | John |
| 2006/0001538 A1 | 1/2006 | Kraft et al. |
| 2006/0137695 A1 | 6/2006 | Hellwig et al. |
| 2006/0173444 A1 | 8/2006 | Choy et al. |
| 2007/0150019 A1 | 6/2007 | Youker et al. |
| 2007/0233051 A1 | 10/2007 | Hohl et al. |
| 2007/0287985 A1 | 12/2007 | Estes et al. |
| 2008/0004601 A1 | 1/2008 | Jennewine et al. |
| 2008/0017194 A1 | 1/2008 | Hassanein et al. |
| 2008/0089313 A1 | 4/2008 | Cayo et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0125700 A1 | 5/2008 | Moberg et al. |
| 2008/0125701 A1 | 5/2008 | Moberg et al. |
| 2008/0195060 A1 | 8/2008 | Roger et al. |
| 2008/0208627 A1 | 8/2008 | Skyggebjerg |
| 2008/0215035 A1 | 9/2008 | Yodfat et al. |
| 2008/0215120 A1 | 9/2008 | Dicks et al. |
| 2008/0224852 A1 | 9/2008 | Dicks et al. |
| 2008/0231226 A1 | 9/2008 | Hoffman et al. |
| 2008/0287922 A1 | 11/2008 | Panduro |
| 2008/0294024 A1 | 11/2008 | Cosentino et al. |
| 2008/0312584 A1 | 12/2008 | Montgomery et al. |
| 2009/0037020 A1 | 2/2009 | Brown |
| 2009/0069868 A1 | 3/2009 | Bengtsson et al. |
| 2009/0085768 A1 | 4/2009 | Patel et al. |
| 2009/0088731 A1 | 4/2009 | Campbell et al. |
| 2009/0108016 A1 | 4/2009 | Brown et al. |
| 2009/0115628 A1 | 5/2009 | Dicks et al. |
| 2009/0177142 A1 | 7/2009 | Blomquist et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0209945 A1 | 8/2009 | Lobl et al. |
| 2009/0212966 A1 | 8/2009 | Panduro |
| 2009/0227855 A1 | 9/2009 | Hill et al. |
| 2009/0227888 A1 | 9/2009 | Salmi et al. |
| 2009/0240193 A1 | 9/2009 | Mensinger et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0281393 A1 | 11/2009 | Smith |
| 2010/0022937 A1 | 1/2010 | Bedingfield et al. |
| 2010/0023582 A1 | 1/2010 | Pedersen et al. |
| 2010/0063765 A1 | 3/2010 | Carlisle et al. |
| 2010/0093319 A1 | 4/2010 | Sherman |
| 2010/0094110 A1 | 4/2010 | Heller et al. |
| 2010/0121169 A1 | 5/2010 | Petisce et al. |
| 2010/0134305 A1 | 6/2010 | Lu et al. |
| 2010/0152811 A1 | 6/2010 | Flaherty |
| 2010/0160759 A1 | 6/2010 | Celentano et al. |
| 2010/0179402 A1 | 7/2010 | Goode, Jr. et al. |
| 2010/0192686 A1 | 8/2010 | Kamen et al. |
| 2010/0198142 A1 | 8/2010 | Sloan et al. |
| 2010/0198183 A1 | 8/2010 | Lanigan et al. |
| 2010/0234709 A1 | 9/2010 | Say et al. |
| 2010/0235439 A1 | 9/2010 | Goodnow |
| 2010/0274218 A1 | 10/2010 | Yodfat et al. |
| 2010/0286653 A1 | 11/2010 | Kubel et al. |
| 2010/0292556 A1 | 11/2010 | Golden |
| 2010/0305421 A1 | 12/2010 | Ow-Wing |
| 2010/0324382 A1 | 12/2010 | Cantwell et al. |
| 2011/0009824 A1 | 1/2011 | Yodfat et al. |
| 2011/0040247 A1 | 2/2011 | Mandro et al. |
| 2011/0040251 A1 | 2/2011 | Blomquist et al. |
| 2011/0046469 A1 | 2/2011 | Nelson et al. |
| 2011/0047499 A1 | 2/2011 | Mandro et al. |
| 2011/0066555 A1 | 3/2011 | Dicks et al. |
| 2011/0078441 A1 | 3/2011 | Dicks et al. |
| 2011/0149759 A1 | 6/2011 | Jollota |
| 2011/0152770 A1 | 6/2011 | DiPerna et al. |
| 2011/0152970 A1 | 6/2011 | Jollota et al. |
| 2011/0169610 A1 | 7/2011 | Geissler et al. |
| 2011/0172744 A1 | 7/2011 | Davis et al. |
| 2011/0190614 A1 | 8/2011 | Brister et al. |
| 2011/0190694 A1 | 8/2011 | Lanier, Jr. et al. |
| 2011/0193704 A1 | 8/2011 | Harper et al. |
| 2011/0201911 A1 | 8/2011 | Johnson et al. |
| 2011/0213329 A1 | 9/2011 | Yodfat et al. |
| 2011/0213621 A1 | 9/2011 | Dicks et al. |
| 2011/0256024 A1 | 10/2011 | Cole et al. |
| 2011/0257895 A1 | 10/2011 | Brauker et al. |
| 2012/0022324 A1 | 1/2012 | Forsell |
| 2012/0029433 A1 | 2/2012 | Michaud et al. |
| 2012/0041415 A1 | 2/2012 | Estes et al. |
| 2012/0091813 A1 | 4/2012 | Spurlin et al. |
| 2012/0095393 A1 | 4/2012 | Reinke et al. |
| 2012/0116197 A1 | 5/2012 | Moberg et al. |
| 2012/0185267 A1 | 7/2012 | Kamen et al. |
| 2012/0232520 A1 | 9/2012 | Sloan et al. |
| 2012/0277667 A1* | 11/2012 | Yodat ............... A61M 5/1456 604/65 |
| 2012/0302991 A1 | 11/2012 | Blomquist et al. |
| 2013/0053816 A1 | 2/2013 | DiPerna et al. |
| 2013/0162426 A1 | 6/2013 | Wiesner et al. |
| 2013/0283196 A1 | 10/2013 | Farnan et al. |
| 2013/0324928 A1 | 12/2013 | Kruse |
| 2013/0331790 A1 | 12/2013 | Brown et al. |
| 2014/0054883 A1 | 2/2014 | Lanigan et al. |
| 2014/0075169 A1 | 3/2014 | Andrews |
| 2014/0113553 A1 | 4/2014 | Brukalo et al. |
| 2014/0175682 A1 | 6/2014 | Johnson et al. |
| 2014/0187890 A1 | 7/2014 | Mensinger et al. |
| 2014/0200426 A1 | 7/2014 | Taub et al. |
| 2014/0276419 A1 | 9/2014 | Rosinko et al. |
| 2014/0276423 A1 | 9/2014 | Lecanu-Fayet |
| 2014/0323961 A1 | 10/2014 | Blomquist et al. |
| 2014/0371816 A1 | 12/2014 | Matos |
| 2015/0011970 A1 | 1/2015 | Kamen et al. |
| 2015/0052511 A1 | 2/2015 | Kiaie et al. |
| 2015/0077038 A1 | 3/2015 | Chao et al. |
| 2015/0174320 A1 | 6/2015 | Grant et al. |
| 2015/0187187 A1 | 7/2015 | Del Toro et al. |

(56) References Cited

U.S. PATENT DOCUMENTS

| | | |
|---|---|---|
| 2016/0004390 A1 | 1/2016 | Laska |
| 2016/0015888 A1 | 1/2016 | Tieck et al. |
| 2016/0098848 A1 | 4/2016 | Zamanakos et al. |
| 2016/0228041 A1 | 8/2016 | Heller et al. |
| 2016/0271325 A1 | 9/2016 | Farnan et al. |
| 2016/0328991 A1 | 11/2016 | Simpson et al. |
| 2016/0339172 A1 | 11/2016 | Michaud et al. |
| 2016/0367753 A1* | 12/2016 | Kamen ............ A61M 5/14248 |
| 2017/0049957 A1 | 2/2017 | Michaud |
| 2017/0049960 A1 | 2/2017 | Nguyen |
| 2017/0056590 A1 | 3/2017 | DiPerna et al. |
| 2017/0127462 A1 | 5/2017 | Liu |
| 2017/0142658 A1 | 5/2017 | Kruse |
| 2017/0173261 A1 | 6/2017 | O'Connor et al. |
| 2017/0216523 A1* | 8/2017 | Neftel .................. A61M 5/172 |
| 2017/0266381 A1 | 9/2017 | Bryant, Jr. et al. |
| 2017/0290535 A1 | 10/2017 | Rao et al. |
| 2017/0300206 A1 | 10/2017 | Rosinko et al. |
| 2017/0312423 A1 | 11/2017 | Rosinko |
| 2018/0071454 A1 | 3/2018 | Betts et al. |
| 2018/0137252 A1 | 5/2018 | Mairs et al. |
| 2018/0137938 A1 | 5/2018 | Vaddiraju et al. |
| 2018/0193555 A1* | 7/2018 | Michaud ........... A61M 5/14248 |
| 2018/0264189 A1 | 9/2018 | Michaud et al. |
| 2019/0121506 A1 | 4/2019 | Matikyan |
| 2019/0175823 A1 | 6/2019 | Rosinko |
| 2019/0240398 A1 | 8/2019 | Seitz et al. |
| 2019/0255248 A1 | 8/2019 | Michaud |
| 2019/0321545 A1 | 10/2019 | Rosinko |
| 2019/0321546 A1 | 10/2019 | Michaud et al. |
| 2019/0321552 A1 | 10/2019 | DiPerna et al. |
| 2019/0351134 A1 | 11/2019 | Cook et al. |
| 2020/0009319 A1 | 1/2020 | Ludolph |
| 2020/0009320 A1 | 1/2020 | Ludolph |
| 2020/0206420 A1 | 7/2020 | Michaud |
| 2020/0261644 A1 | 8/2020 | Farnan et al. |
| 2020/0306445 A1 | 10/2020 | Michaud et al. |
| 2020/0329433 A1 | 10/2020 | Kruse et al. |
| 2020/0372995 A1 | 11/2020 | Kruse et al. |

FOREIGN PATENT DOCUMENTS

| | | |
|---|---|---|
| WO | WO-2007098265 A2 | 8/2007 |
| WO | WO-2007098287 A2 | 8/2007 |
| WO | WO-2009013736 A1 | 1/2009 |
| WO | WO-2009016636 A2 | 2/2009 |
| WO | WO-2016059616 A1 | 4/2016 |
| WO | WO-2016145094 A2 | 9/2016 |
| WO | WO-2017007775 A2 | 1/2017 |
| WO | WO 2018/111928 A1 | 6/2018 |
| WO | WO 2020/198422 A1 | 10/2020 |

OTHER PUBLICATIONS

Application and File history for U.S. Appl. No. 15/868,461, filed Jan. 11, 2018, Inventors Michaud et al.

Application and File history for U.S. Appl. No. 16/502,196, filed Jul. 3, 2019, Inventors Michaud et al.

Wu J., et al., "Wireless Power and Data Transfer via a Common Inductive Link Using Frequency Division Multiplexing," IEEE Transactions on Industrial Electronics, vol. 62 (12), Jul. 9, 2015, pp. 1-10.

Search Report and Written Opinion dated Jul. 25, 2020 for PCT Application No. PCT/US2020/024857, 11 pages.

* cited by examiner

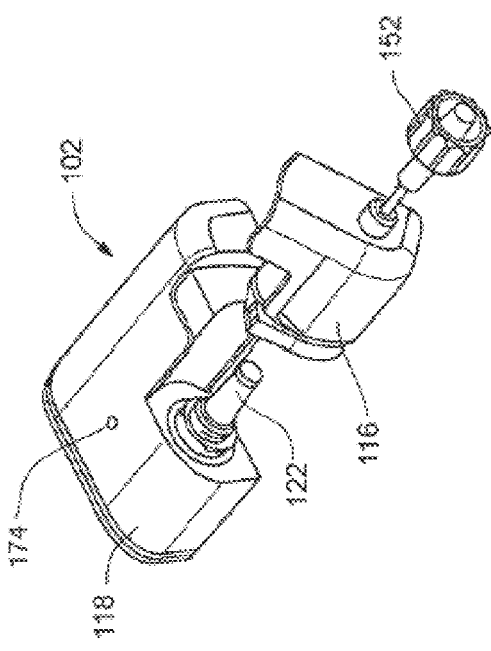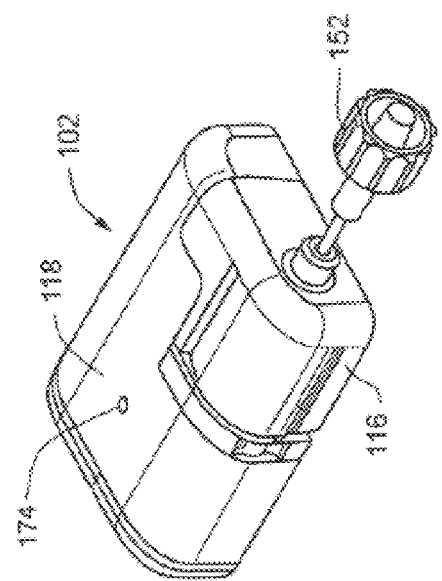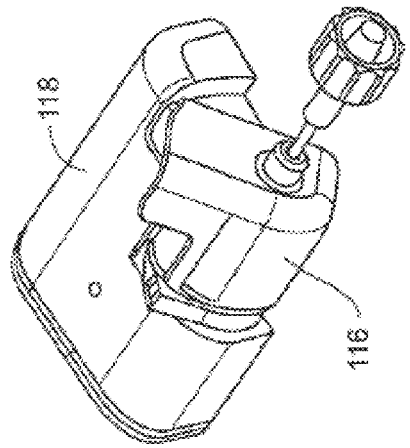

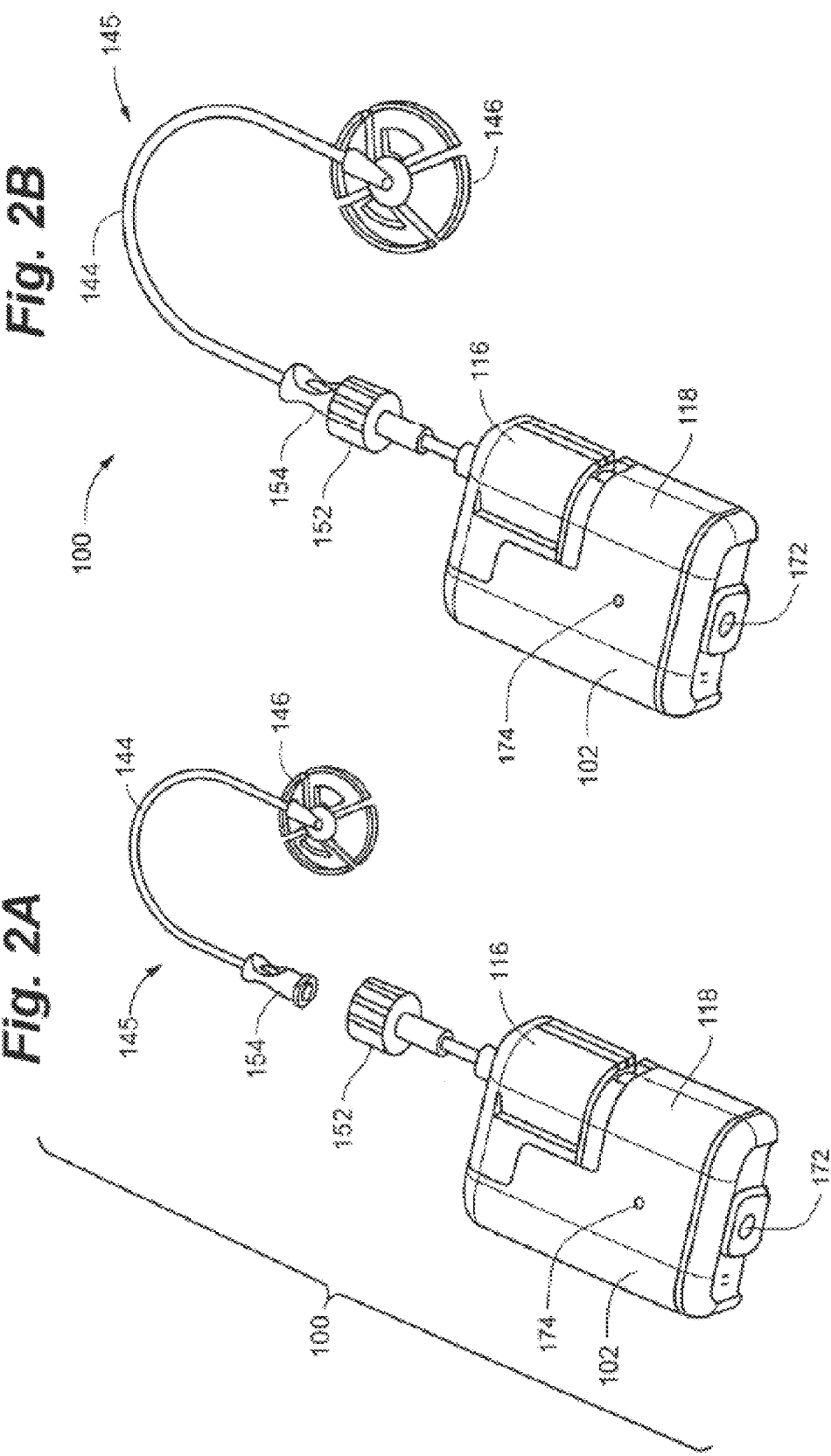

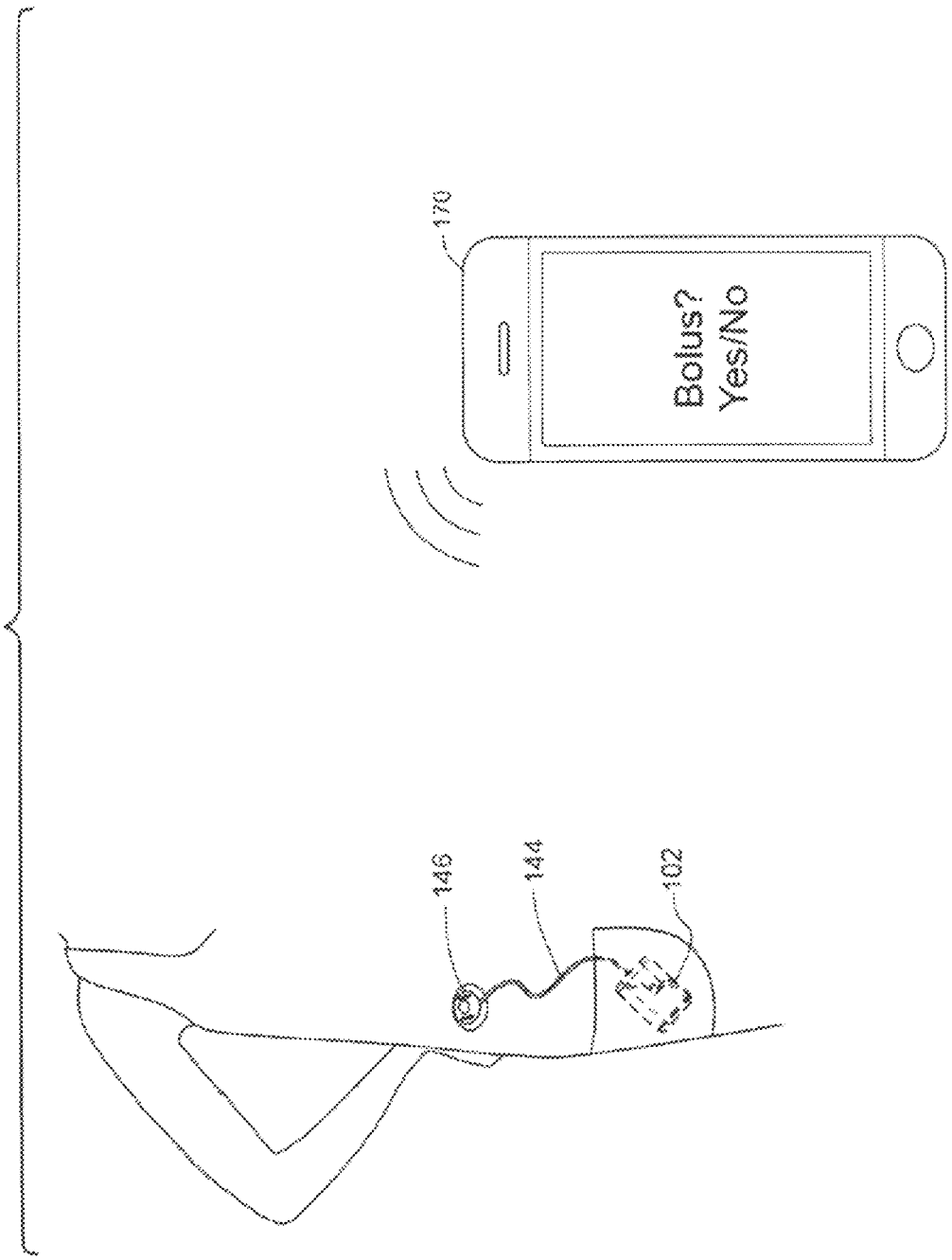

LED TERMINOLOGY (LED colors used for example only)

Below are the terms used for LED patterns throughout the Wombat workflows.

| LED DISPLAY | LED TERM | DEFINITION |
|---|---|---|
|  | DISPLAY | The LED is set to ON and stays ON until turned off by the user or by the system. The duration is indicated by the workflows. |
|  | BLINK | The LED is set to ON, displays for a set period of time, and is then set to OFF for a set period of time. The pattern repeats as indicated by the workflows. |
|  | PULSATE | The LED is set to ON at the lowest allowable brightness, increases to the highest allowable brightness, and then returns to the lowest allowable brightness in a set period of time. The pattern repeats as indicated by the workflows. |

*Fig. 5A*

VIBE TERMINOLOGY

Below are the terms used for Vibe patterns throughout the Wombat workflows.

| VIBE TERM | DEFINITION |
|---|---|
| SHORT | The vibe will last approximately 100 ms. |
| MEDIUM | The vibe will last approximately 500 ms. |
| LONG | The vibe will last approximately 1 second. |

*Fig. 5B*

SYSTEM DRIVEN EVENTS

A System Driven Event is when the pump alerts the user without pressing the Quick Bolus button of the Wombat pump.

| LED DISPLAY | SYSTEM EVENT | LED PATTERN | BEEP PATTERN | VIBE PATTERN | RE-ANNUNCIATION |
|---|---|---|---|---|---|
| | BOLUS INITIATED<br>From Pump<br>OR From Controller | • Blink LEDs alternately on and off at 500 ms/blink for each LED.<br>• Repeat 4 more times (Total of 5 Blink patterns)<br>• Turn LEDs OFF | Bolus Initiated Alert Pattern from t:slim (1 beep upon Bolus Initiation)<br>*Does not occur if Bolus Volume is set to VIBRATE in Sound Volume* | Bolus Initiated Alert Pattern from t:slim (1 Vibe upon Bolus Initiation at 1 sec per Vibe) | N/A |
| | PUMP MALFUNCTION | • Both LEDs display for 5 seconds<br>• Turn LEDs OFF | Pump Malfunction Pattern from t:slim<br>*Occurs at HIGH Volume* | Pump Malfunction Pattern from t:slim | Pump Malfunction Pattern from t:slim |
| | PUMP ALARM | • Blink both LEDs 3 times every 1 second<br>• Wait 1 second<br>• Repeat 2 more times (Total of 3 Blink Patterns)<br>• Turn LEDs OFF | Pump Alarm Pattern from t:slim (3 beep pattern, repeated three times)<br>*Does not occur if Alarm Volume is set to VIBRATE in Sound Volume* | Pump Alarm Pattern from t:slim (3 Vibes at 1 sec per Vibe) | Pump Alarm Pattern from t:slim (Re-annunciates all patterns if not acknowledged within 3 min) |
| | PUMP ALERT | • Blink both LEDs 3 times every 1 second<br>• Wait 1 second<br>• Repeat 2 more times (Total of 3 Blink Patterns)<br>• Turn LEDs OFF | Pump Alert Pattern from t:slim (3 beep pattern, repeated twice)<br>*Does not occur if Alert Volume is set to VIBRATE in Sound Volume* | Pump Alert Pattern from t:slim (2 Vibes at 1 sec per Vibe) | Pump Alert Pattern from t:slim (Re-annunciates all patterns if not acknowledged within 5 min) |

ORDER OF ANNUNCIATION FOR SYSTEM DRIVEN EVENTS

When a System Event is triggered –

1. The pump will annunciate the BEEP PATTERN.
2. The VIBE PATTERN will annunciate 1 second after the BEEP PATTERN has completed.
3. The LED PATTERN will start at the time the System Event is triggered and will display its pattern until complete, independent of the BEEP and VIBE PATTERNS.

*Fig. 6A*

SYSTEM DRIVEN EVENTS – DESCRIPTION AND RULES

A System Driven Event is when the pump alerts the user without pressing the Function button of the Wombat pump.

R1 & E1 – When a System Driven Event occurs, the annunciation pattern of beeps, vibes, and LEDs will complete before starting any other user initiated pattern.
R2 & E2 – When a System Driven Event occurs, the Function button vibe will be disabled for the duration of the annunciation pattern (the [...] vibe that occurs when the user presses the Function button).

| LED DISPLAY | SYSTEM EVENT | LED PATTERN | BEEP PATTERN | VIBE PATTERN | RE-ANNUNCIATION |
|---|---|---|---|---|---|
| | BOLUS INITIATED From Pump OR From Controller | • Pulsate LEDs alternately on and off<br>• LED pattern lasts for approx 10 seconds<br>• Turn LEDs OFF | Bolus Initiated Alert Pattern from t:slim (1 beep upon Bolus Initiation) [...] | Bolus Initiated Alert Pattern from t:slim (1 LONG Vibe upon Bolus Initiation) | N/A |
| | PUMP MALFUNCTION | • Blink both LEDs 3 times<br>• Wait 1 second<br>• Repeat 4 more times (Total of 5 Blink Patterns)<br>• Turn LEDs OFF | Pump Malfunction Pattern from t:slim (3 beep pattern, repeated three times) [...] | Pump Malfunction Pattern from t:slim (3 LONG Vibes) | Pump Malfunction Pattern from t:slim (Re-annunciates all patterns if not acknowledged in 3 min) |
| | PUMP ALARM | • Blink both LEDs 3 times<br>• Wait 1 second<br>• Repeat 4 more times (Total of 5 Blink Patterns)<br>• Turn LEDs OFF | Pump Alarm Pattern from t:slim (3 beep pattern, repeated three times) [...] | Pump Alarm Pattern from t:slim (3 LONG Vibes) | Pump Alarm Pattern from t:slim (Re-annunciates all patterns if not acknowledged in 3 min) |
| | PUMP ALERT | • Blink both LEDs 2 times<br>• Wait 1 second<br>• Repeat 4 more times (Total of 5 Blink Patterns)<br>• Turn LEDs OFF | Pump Alert Pattern from t:slim (3 beep pattern, repeated twice) [...] | Pump Alert Pattern from t:slim (2 LONG Vibes) | Pump Alert Pattern from t:slim (Re-annunciates all patterns if not acknowledged in 5 min) |
| | CGM ALERT | • Blink both LEDs 2 times<br>• Wait 1 second<br>• Repeat 4 more times (Total of 5 Blink Patterns)<br>• Turn LEDs OFF | CGM Alert Pattern from t:slim (Unique to each CGM Alert) [...] | CGM Alert Pattern from t:slim (Unique to each CGM Alert) | CGM Alert Pattern from t:slim (Unique to each CGM Alert) |
| | PUMP REMINDER | • Blink both LEDs 1 time<br>• Wait 1 second<br>• Repeat 4 more times (Total of 5 Blink Patterns)<br>• Turn LEDs OFF | Pump Reminder Pattern from t:slim (3 beep pattern, annunciated once) [...] | Pump Reminder Pattern from t:slim (1 LONG Vibe) | Pump Reminder Pattern from t:slim (Re-annunciates all patterns if not acknowledged in 10 min) |

ORDER OF ANNUNCIATION FOR SYSTEM DRIVEN EVENTS

When a System Event is triggered –

1. The pump will annunciate the BEEP PATTERN.
2. The VIBE PATTERN will annunciate 1 second after the BEEP PATTERN has completed.
3. The LED PATTERN will start at the time the System Event is triggered and will display its pattern until complete, independent of the BEEP and VIBE PATTERNS.

*Fig. 6B*

USER DRIVEN EVENTS

A User Driven Event is when the user presses the Quick Bolus button once to view the current status of the pump.
A User Driven Event is LED display ONLY – Beeps and Vibes do NOT annunciate, even if an Alert, Alarm or Malfunction is still present.
Once the Quick Bolus button is pressed, the LED pattern will display as indicated below.
The LEDs will return to the OFF state when 5 seconds has elapsed, or if the user presses the Quick Bolus button while the pattern is in progress.

USER DRIVEN EVENTS – PUMP ALERTS, PUMP ALARMS & MALFUNCTIONS

If a Pump Alert, Alarm or Malfunction is present, its LED Pattern will take priority over all other Pumping State patterns.
Pump Alert, Alarm or Malfunction LED Patterns will remain active on the pump until the user has acknowledged it on the Controller.

| LED DISPLAY | SYSTEM EVENT | LED PATTERN | PRIORITY |
|---|---|---|---|
|  | PUMP MALFUNCTION | • Both LEDs display for 5 seconds<br>• Turn LEDs OFF | 1st |
|  | PUMP ALARM | • Blink both LEDs 3 times every 1 second<br>• Wait 1 second<br>• Repeat 2 more times (Total of 3 Blink Patterns)<br>• Turn LEDs OFF | 2nd |
|  | PUMP ALERT | • Blink both LEDs 3 times every 1 second<br>• Wait 1 second<br>• Repeat 2 more times (Total of 3 Blink Patterns)<br>• Turn LEDs OFF | 3rd |

*Fig. 7A*

USER DRIVEN EVENTS – PUMPING STATE

The LED Patterns below indicate the current pumping state of the pump. Each LED Pattern lasts for a total of approx 10 seconds and then both LEDs turn off.

| LED DISPLAY | SYSTEM STATUS | LED PATTERN | PRIORITY |
|---|---|---|---|
| | STANDARD BOLUS IN PROGRESS <br><br> Includes Standard, Override, Correction, Standard/Correction, Quick Boluses and Auto-Boluses from Control-IQ | • Pulsate LEDs alternately on and off <br> • LED pattern lasts for approx 10 seconds <br> • Turn LEDs OFF | 1st |
| | EXTENDED BOLUS IN PROGRESS <br><br> This is for the Extended Portion ONLY. The Standard Portion will display the Standard Bolus Pattern above | • LED 1 displays ON <br> • LED 2 pulsates <br> • LED pattern lasts for approx 10 seconds <br> • Turn LEDs OFF | 2nd |
| | USER SET TEMP RATE IN PROGRESS | • LED 1 displays ON <br> • LED 2 pulsates <br> • LED pattern lasts for approx 10 seconds <br> • Turn LEDs OFF | 3rd |
| | BASAL PUMPING AS EXPECTED <br><br> This includes increased or decreased basal via Control-IQ | • Pulsate LEDs alternately on and off <br> • LED pattern lasts for approx 10 seconds <br> • Turn LEDs OFF | 4th |
| | BASAL PUMPING ALL DELIVERIES STOPPED BY ALGORITHM <br><br> This includes basal suspended from Basal-IQ or Control-IQ | • Pulsate LEDs alternately on and off <br> • LED pattern lasts for approx 10 seconds <br> • Turn LEDs OFF | 4th |
| | ALL DELIVERIES STOPPED BY USER <br><br> This is if the user manually stopped insulin using the controller (STOP INSULIN or through Load sequences) | • Blink both LEDs 1 time <br> • Wait 1 second <br> • Repeat 2 more times (Total of 3 Blink Patterns) <br> • Turn LEDs OFF | 5th |

*Fig. 7B*

USER DRIVEN EVENTS – PUMP ALERTS, PUMP ALARMS & MALFUNCTIONS

If a Pump Alert, Alarm or Malfunction is present, its LED Pattern will take priority over all other Pumping State patterns.
Pump Alert, Alarm or Malfunction LED Patterns will remain active on the pump until the user has acknowledged it on the Controller.

| LED DISPLAY | SYSTEM EVENT | LED PATTERN | PRIORITY |
|---|---|---|---|
|  | PUMP MALFUNCTION | • Both LEDs display for 5 seconds<br>• Turn LEDs OFF | 1st |
|  | PUMP ALARM | • Blink both LEDs 3 times every 1 second<br>• Wait 1 second<br>• Repeat 2 more times (Total of 3 Blink Patterns)<br>• Turn LEDs OFF | 2nd |
|  | PUMP ALERT<br>CGM ALERT | • Blink both LEDs 2 times every 1 second<br>• Wait 1 second<br>• Repeat 2 more times (Total of 3 Blink Patterns)<br>• Turn LEDs OFF | 3rd |
|  | PUMP REMINDER | • Blink both LEDs 1 time every 1 second<br>• Wait 1 second<br>• Repeat 2 more times (Total of 3 Blink Patterns)<br>• Turn LEDs OFF | 4th |

*Fig. 7C*

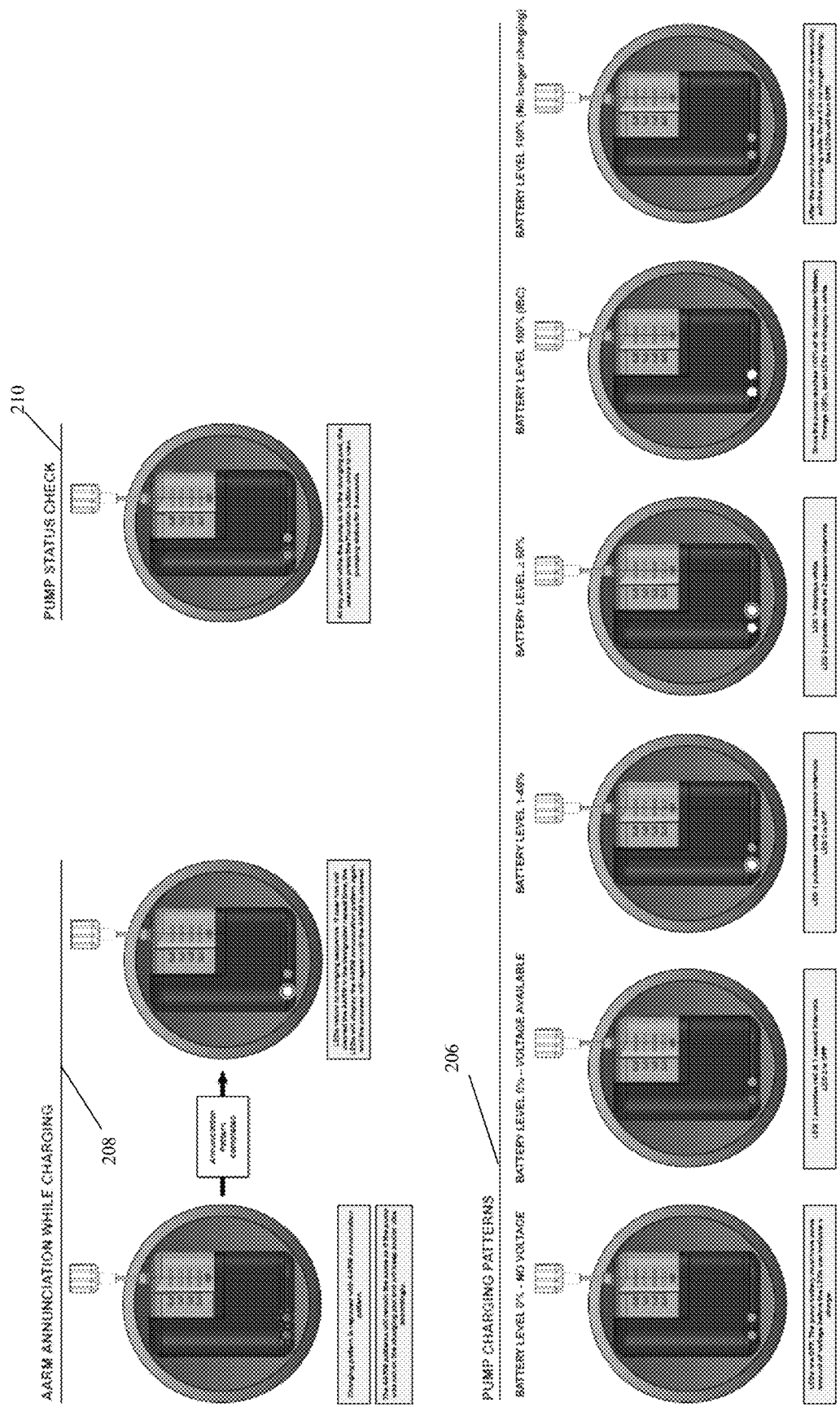

LIST OF INTERACTIONS THAT WILL RESET THE AUTO-OFF TIMER

| PUMP INTERACTIONS | CONTROLLER INTERACTIONS | CONTROLLER INTERACTIONS | CONTROLLER INTERACTIONS |
|---|---|---|---|
| Snooze (includes if setting is disabled) | Bolus Button on Home Screen | High BG Reminder Setting Save | Time Setting Save |
| Quick Bolus (when it setting disabled?) | Requesting Bolus on Confirmation Screen | After Bolus BG Reminder Settings Save | Date Setting Save |
| Pump starts to charge | Requesting Insulin on Options Screen | Missed Meal Bolus Settings (1-4) Save | Pump Favorite Settings Save |
| Pump completes charging | Site Reminder Setting Save | Low Insulin Alert Setting Save | Pump Alerts & Alarms Sound Settings Save |
| Pump enters Pairing Sequence | Exercise Start/Stop | Auto-off Setting Save | Security PIN Setting Save |
| Pump completes Pairing Sequence | Sleep Start/Stop | Quiet Bolus Settings Save | Forget My Pump |
| Pump is Unpaired | Sleep Schedule (1/2) Settings Save | CGM Start/Stop Sensor | View Delivery Summary |
| | Temp Rate Start/Stop | Calibrate CGM | View Total Daily Dose |
| | Personal Profile New Profile Save | CGM High Alert Setting Save | View Bolus History |
| | Timed Segment Save | CGM Low Alert Setting Save | View Basal History |
| | Bolus Settings Save | CGM Rise Alert Setting Save | View Lows History |
| | Duplicate Profile Save | CGM Fall Alert Setting Save | View BG History |
| | Control IQ/Basal IQ Settings Save | CGM Out of Range Setting Save | CGM Out of Range Setting Save |
| | Low BG Reminder Setting Save | CGM Transmitter ID Save | View Alerts and Alarms History |

| CONTROLLER INTERACTIONS |
|---|
| View Control-IQ/Basal-IQ History |
| View Ecosystem History |
| View CGM Sessions and Calibrations History |
| View CGM Alerts and Errors History |
| View CGM Complete History |

METHOD AND SYSTEM OF OPERATING AN INFUSION PUMP WITH A REMOTE CONTROL DEVICE

RELATED APPLICATION

The present application claims the benefit of U.S. Provisional Application No. 62/823,991 filed Mar. 26, 2019, which is hereby incorporated herein in its entirety by reference.

TECHNICAL FIELD

The present invention relates to medical pumps for delivering medicament to a patient, and more specifically, to a user-wearable pump controllable with a remote control device.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of insulin injecting pumps that have been developed for the administration of insulin for those suffering from both type I and type II diabetes. Some insulin injecting pumps configured as portable infusion devices can provide continuous subcutaneous insulin injection and/or infusion therapy for the treatment of diabetes. Therapy may include the regular and/or continuous injection or infusion of insulin into the skin of a person suffering from diabetes and offer an alternative to multiple daily injections of insulin by an insulin syringe or an insulin pen. These pumps can be ambulatory/portable infusion pumps that are worn by the user and may use replaceable cartridges. Medicaments other than or in addition to insulin, such as glucagon, pramlintide, etc. can also be delivered. Examples of such pumps and various features that can be associated with such pumps include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790, U.S. Pat. No. 8,287,495 and U.S. patent application Ser. No. 15/158,125, each of which is hereby incorporated herein by reference in its entirety.

One type of pump that has been developed is a patch pump also known as a micro pump. Patch pumps are small pumps, typically ambulatory, that may be carried directly on the skin under the user's clothing. In some cases, the pumps are situated directly on, or very near to, the injection site such that little or no tubing is required to deliver the insulin or other medicament to the patient. Some patch pumps include a single button on the pump to initiate delivery of medicament and do not include a built-in display or user interface. These pumps are therefore primarily remote-controlled. Having only a single button on the pump provides the advantage of being more robust for waterproofing and resistance to external contaminants. However, a disadvantage is that the functionality of a pump with a single button is limited without the use of a remote control apparatus, typically including a user interface. Such functionality is further limited if the patch pump does not include a display screen.

With the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

SUMMARY

Embodiments of the present disclosure enable a user-wearable infusion pump that may have a limited user interface including no display to execute and provide feedback on a number of functions. A remote control device having a display can be used to control the infusion pump. The infusion pump can include one or more indicator lights that can be indicate different statuses with different light patterns. The remote control device can include a display screen that provides further information relating to various pump statuses.

In an embodiment, a method of operating a user-wearable infusion pump having no display screen with a remote control device is provided. A plurality of menus can be presented on a display screen of the remote control device, with the plurality of menus including menu items enabling programming of operating parameters for the user-wearable infusion pump. A current status of the infusion pump can be detected and an indication provided of the current status with a light pattern of indicator light(s) of the pump with the light pattern of the current status being selected from a plurality of different light patterns stored in memory each indicating a different type of pump status. Information relating to the current status of the infusion pump indicated by the light pattern of the current status can also be presented on the display screen of the remote control device.

In an embodiment, a system for operating an infusion pump with a remote control device is provided. The system can include a user-wearable infusion pump having one or more indicator lights and a display screen. The one or more indicator lights can provide an indication of a current status of the infusion pump by displaying a light pattern corresponding to the current status selected from a plurality of different light patterns each indicating a different type of pump status. The system can further include a remote control device having a display screen configured to present a plurality of menus including menu items enabling programming of operation parameters for the infusion pump to remotely control the user-wearable infusion pump. The remote control device can display on the display screen information relating to the current status of the infusion pump indicated by the light pattern displayed by the one or more indicator lights of the infusion pump.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1C depict an embodiment of an infusion pump system according to the disclosure.

FIGS. 2A-2C depict an embodiment of an infusion pump system according to the disclosure.

FIG. 3 depicts an embodiment of an infusion pump system according to the disclosure.

FIGS. 5A-5B depict aspects of an infusion pump system according to the disclosure.

FIGS. 6A-6B depict aspects of an infusion pump system according to the disclosure.

FIGS. 7A-7D depict aspects of an infusion pump system according to the disclosure.

FIGS. 9A-9B depict charging sequences for an infusion pump system according to the disclosure.

FIGS. 30A-30C depict a workflow and various screens that can be displayed on a remote control device for an infusion pump system relating to an auto-off feature according to the disclosure.

FIG. 33 depicts a workflow and various screens that can be displayed on a remote control device for an infusion pump system for accessing device history according to the disclosure.

Figure 2C:
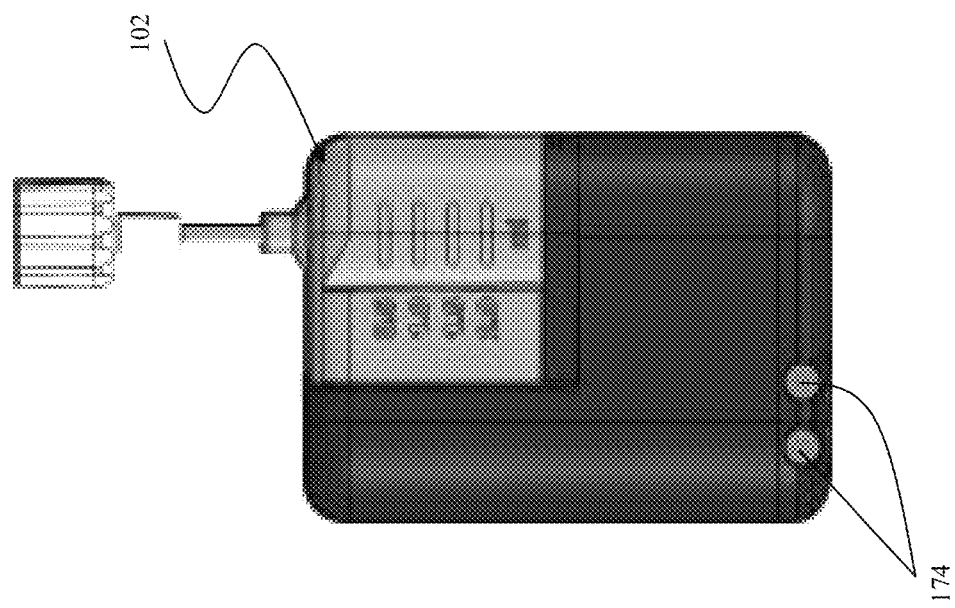

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Infusion Pump System

Referring to FIGS. 1A-1C, a pump system 100 including a pump 102 is depicted in accordance with an embodiment of the disclosure. Drive unit 118 of pump 102 includes a drive mechanism 122 that mates with a recess in medicament cartridge 116 of pump 102 to attach the medicament cartridge 116 to the drive unit 118. Further details regarding example embodiments of such delivery mechanisms can be found in U.S. Patent Publication No. 2017/0049957, which is hereby incorporated by reference in its entirety.

As depicted in the embodiment of FIGS. 2A-2B, pump system 100 can include a pump 102 and an infusion set 145. FIG. 2A depicts this infusion set 145 as not connected to pump while FIG. 2B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user, while pump 102 can be carried in a separate location, such as the user's pocket or another location on the user's body. Various lengths of tubing 144 can be used in this embodiment to accommodate the user's preference. Further details regarding such pumps can be found in U.S. patent application Ser. No. 14/707,851 (filed May 8, 2015); U.S. Patent Application Publication No. 2016/0339172; and U.S. Patent Application Publication No. 2017/0049957, each of which is hereby incorporated herein by reference in its entirety.

In one embodiment, pump 102 includes a processor that controls operations of the pump and, in some embodiments, may communicate in either one-way or two-way modes to, e.g., receive operational commands and/or other signals, including data, from a separate device and/or, e.g., to send signals, including data, to a separate device. Pump 102 can include one or more buttons configured to cause the processor to initiate one or more functions. In the depicted embodiment, pump 102 includes only a single button 172, although more than one button may be present on pump 102. Button 172 can be configured to, for example, initiate delivery of medicament. Any single button such as button 172 can be utilized to execute a plurality of functions or operations. For example, a single press of button may initiate one function, holding the button down for a predetermined period of time may initiate another function, etc. Because the depicted pump 102 optionally does not itself include a display or user interface, information and feedback regarding medicament delivery or dosing initiated with button 172 can be communicated to and displayed on a remote control device or other device having a display and/or other type of user interface. Further details regarding use of button 172 can be found in U.S. Patent Publication No. 2018/0193555, which is hereby incorporated by reference in its entirety.

In one embodiment, pump 102 includes a light source, such as a light emitting diode (LED) 174. Light source 174 can be configured to provide user feedback regarding user input and/or the performance of a desired function. For example, in one embodiment, light source 174 can illuminate or blink one or more times to indicate that the one or more buttons 172 have been activated and/or that a desired function has been initiated. In one embodiment, pump 102 can additionally and/or alternatively vibrate and/or provide audible notifications to indicate that the one or more buttons 172 have been activated and/or that a desired function has been initiated or, e.g., to provide user feedback regarding user input and/or the performance of the desired function. Illumination of light source 174 and/or vibrations and/or audible notifications may be executed in any number of patterns, frequencies, durations, sequences, combinations, colors, brightness levels, etc. to indicate particular information, such as particular input received and/or particular functions or operations enabled and/or initiated, to the pump user or caregiver. FIG. 2C depicts another embodiment of a pump 102 that includes two indicator lights 174.

Figure 4B:
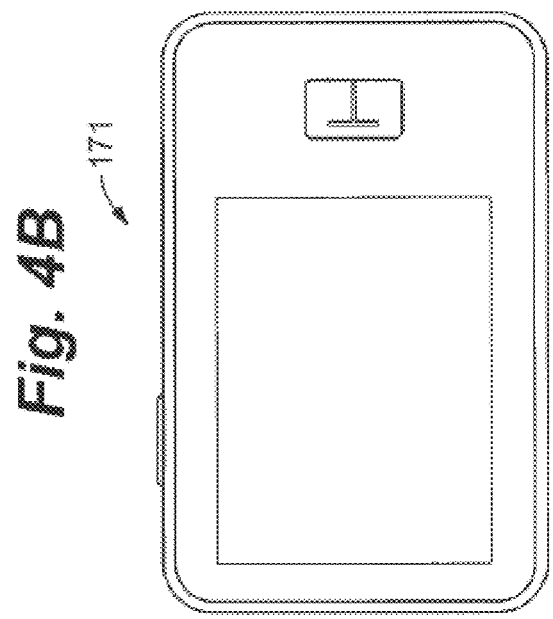
FIGS. 4A-4B depict remote control devices for an infusion pump system according to the disclosure.
Figure 4A:
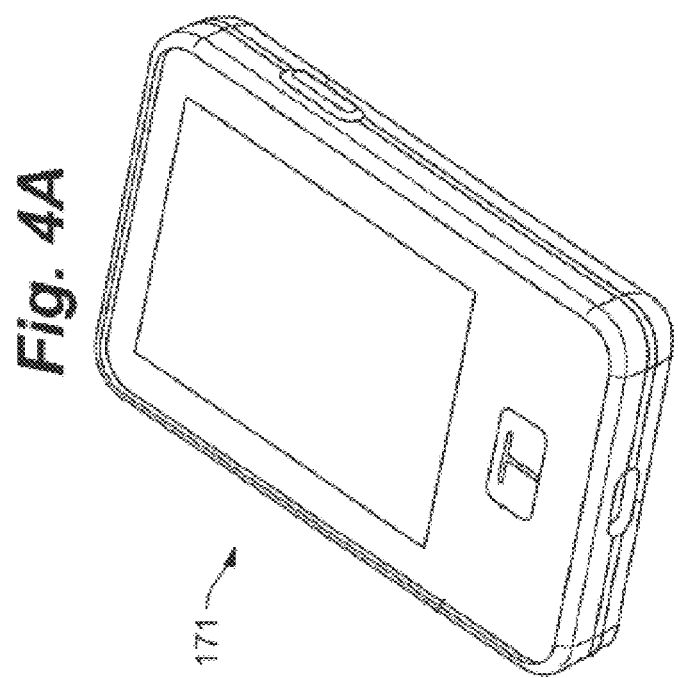

Referring to FIGS. 3-4B, one or more remote control devices 170, 171 can be used to communicate with the processor of pump 102 to control delivery of medicament and transfer data with pump 102 via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 3) executing a software application for control of the pump, a dedicated remote controller 171 (as depicted in FIGS. 4A-4B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Embodiments of the present invention include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

Annunciation Patterns

As noted above, illumination of the one or more indicator lights 174, and particularly in a pump such as that in FIG. 2C having two indicator lights 174, can be executed in any number of patterns, frequencies, durations, sequences, combinations, colors, brightness levels, etc. to indicate particular information. FIGS. 5A-5B set forth indicator light and vibration terminology that can be employed with an infusion pump system according to an embodiment. The indicator lights 174 can include a display pattern, a blink pattern and a pulsate pattern. In the display pattern of this embodiment, the light or lights are set to on and stay(s) on until turned off by the user or by the system. The blink pattern causes the light or lights to turn on for a set period time, then off for a period of time, repeating as required by the system for a particular notification. In a pulsate pattern, the light or lights are turned on at the lowest level of brightness, gradually increase to the highest level of brightness and then return to the lowest brightness in a set period of time, which can then be repeated as required for a particular notification. Similarly, vibration notifications can include short, medium and long vibrations. In one embodiment, short vibrations last for approximately 100 ms, medium vibrations for 500 ms and long vibrations for 1 second.

As will be described herein, the remote control device for the pump can provide display screens, icons, etc. that can communicate pump status and information that correspond to the indications provided by the indicator lights of the pump. The user can therefore use the remote control device display to find out more information regarding a status indicated by the pump lights, respond to or otherwise address a status requiring user action, etc.

FIG. 6A depicts annunciation patterns for communicating system driven events according to an embodiment. A system driven event can include events in which the pump alerts the user unilaterally without the user pressing the button 172 on the pump or otherwise actively requesting a pump status. Each system event can be annunciated with one or more of an indicator light pattern, a beep/sound pattern and/or a vibration/vibe pattern. In one embodiment, when a system even is triggered the pump will first annunciate the beep pattern with the vibe pattern following a predetermined time, e.g., 1 second, after the beep pattern has completed. The indicator light pattern can start when the system even is triggered and the pattern will be displayed until complete, independent of the beep and vibration patterns. System driven events can include a bolus being initiated (whether at the pump or a remote controller), a pump malfunction, a pump alarm and a pump alert. Various example indicator light, beep/sound and vibration/vibe patterns that can correspond to each specific event according to an embodiment are set forth in FIG. 6A. For some events, such as, for example, pump malfunctions, alarms and/or alerts, one or more of the patterns may be re-annunciated if the initial announcement is not acknowledged by the user, such as by pressing the pump button or on a corresponding screen on a remote control. FIG. 6B depicts annunciation patterns for additional system driven events, including CGM alerts for systems in communication with a CGM device and pump reminders. Alerts, alarms, reminders and malfunctions may be generically referred to herein as AARMs. When a system driven event occurs, the annunciation pattern of beeps, vibrations and/or lights will complete before starting any other user-initiated pattern. The input or function button 172 of the pump may also be disabled during the duration of the annunciation pattern.

In embodiments, each different type of AARM can have a specific distinct meaning. Alarms can automatically notify a user of an actual or potential stopping of insulin delivery, such as, for example, the insulin cartridge being empty. Alerts can automatically notify users of safety conditions that the user needs to know about, such as, for example, the amount of insulin in the reservoir is low. Malfunctions can automatically notify a user when the pump detects a system error, such as a mechanical error in the drive mechanism, and the system then stops all deliveries of insulin due to the error. Reminders can automatically notify a user of an optional notification that the user has set for the device, such as, for example, a reminder to check BG after a bolus.

Figure 7D:
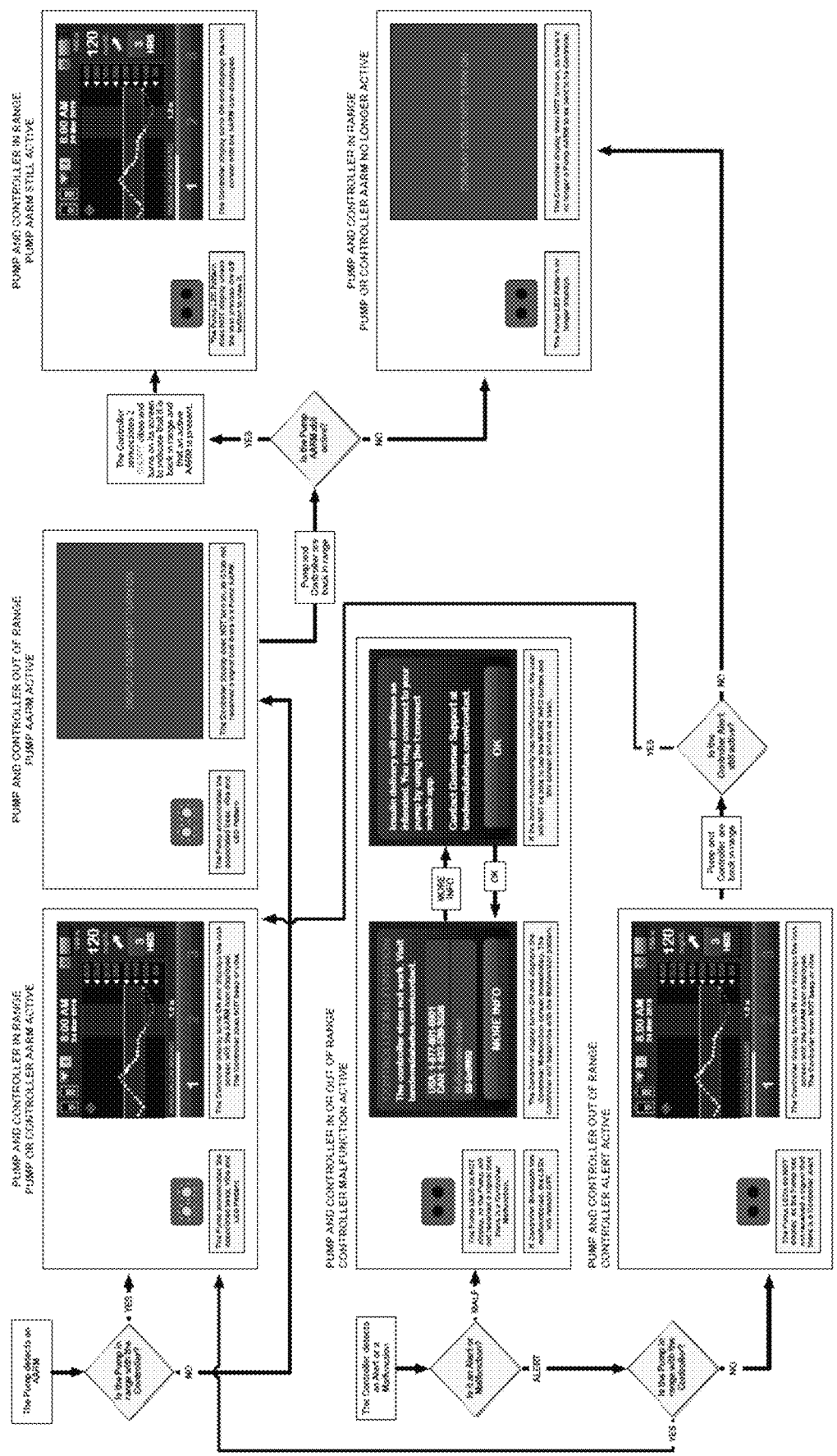

FIGS. 7A-7B depict annunciation patterns for various user driven events according to some embodiments. User driven events can occur when the user presses the button 172 on the pump or otherwise seeks to obtain a current status of the pump. In certain embodiments, user driven events are indicated only by indicator lights 174 and no beep or vibrations will annunciate the status, even if an AARM is present. When the button 172 on the pump is pressed, indicator light patterns can display to indicate various events as depicted in FIGS. 7A-7B. The indicator lights can turn off after a predetermined period of time, such as, for example, 5 seconds. In some embodiments, the lights can be turned off during the displayed pattern by the user pressing the button 172 again. If an AARM is present when the pump status request is received, the AARM can take priority over any other status and the indicator light patterns described in FIG. 7A can remain active until the user acknowledges the annunciation, such as on a remote control device. Other user driven events that can be indicated with different indicator light patterns include pumping state events such as basal rate being delivered, temporary basal rate in progress, standard bolus in progress, extended bolus in progress, all insulin deliveries stopped user and all deliveries stopped by a closed-loop algorithm operating on the pump. One embodiment of indicator light patterns for these events is depicted in FIG. 7B. FIG. 7C depicts additional user driven events that can be indicated with light patterns, including CGM alerts and pump reminders. These additional events can also take precedence over any pumping state patterns if present. FIG. 7D depicts a workflow and remote controller display screens relating to occurrence of an AARM.

Charging Sequence

Figure 8A:
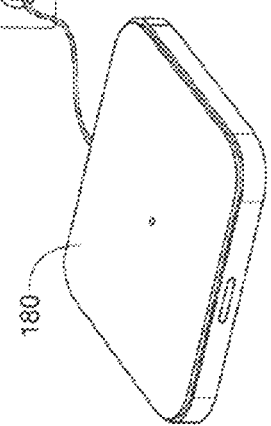
FIGS. 8A-8D depict a procedure for inductively charging a battery of an infusion pump system according to the disclosure.
Figure 8C:
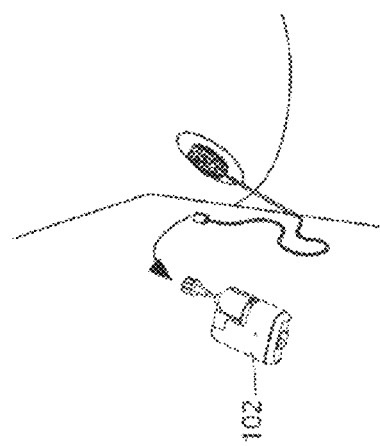
Figure 8B:
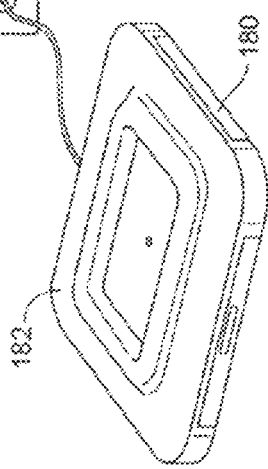
Figure 8D:
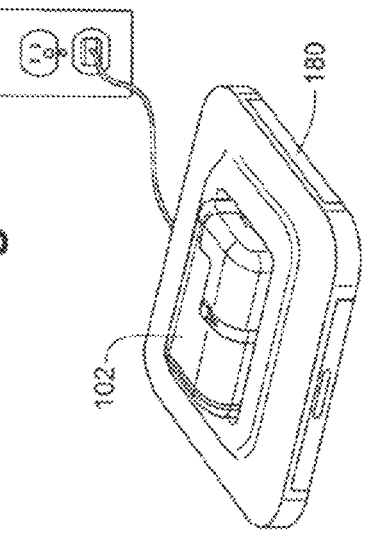

Referring to FIGS. 8A-8D, pumps according to embodiments of the present disclosure can include one or more rechargeable batteries in and/or associated with the pump drive unit 118. In some embodiments, a rechargeable battery can be wirelessly charged, for example through inductive charging by an inductive charging pad 180. As depicted in FIG. 5B, in some embodiments, the charging pad 180 can include a cover 182 having a cutout sized to receive pump 102 in order to properly position and retain pump 102 on the charging pad 180 during recharging. In some embodiments, as shown in FIGS. 8A, 8B and 8D, the charging pad 180 may receive power by being connected to a wall outlet. In other embodiments, the charging pad 180 may additionally or alternatively include a wired and/or wireless power connection to, for example, a computer (e.g., via USB or IEEE 1394), a 12 volt automobile outlet, a battery pack (e.g., via USB or IEEE 1394), optical means, and/or a solar panel, among others.

Figure 9B:
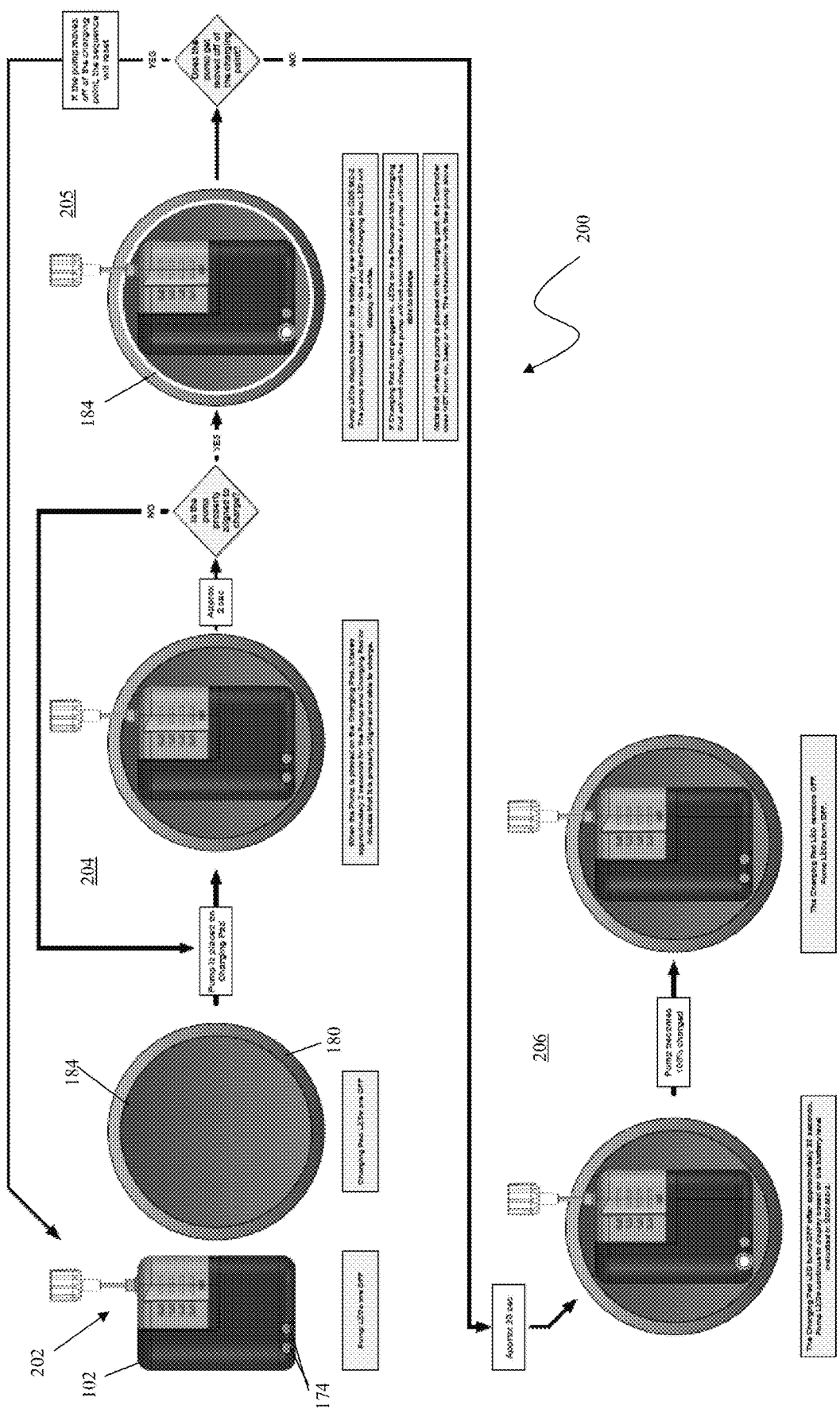

FIGS. 9A-9B depicts a charging sequence 200 for an infusion pump according to an embodiment. At initial step 202, the pump 102 has not yet been placed on the charging pad 180, and the indicator lights 174 are in the off state. The pump 102 is placed on the charging pad at step 204. When the pump has reached the correct charging location (i.e., when the receiving coils in the pump 102 are aligned with the charging coils in the pad 180), the indicator lights can illuminate based on the current battery level of the pump and the pump can vibrate and/or beep to indicate that charging has been initiated. In one embodiment, the pump vibrates two times to indicate charging has been initiated. If the charging pad is not plugged in, this sequence will not take place and the indicator lights will remain off. As the pump battery charges at step 206, the indicator lights can indicate a current charging status of the battery by changing a light pattern and/or color. For example, if the pump battery is at 0%, one or more lights can turn on to indicate that voltage for charging is available and then the light pattern and/or color can change when the battery is between 1-49%, when the battery is between 50-100% and when the battery is 100% charged. The lights can be off if the pump is not charging, either because no voltage is available to charge the pump or once the battery is charged 100% and the lights have already indicated that charging is complete for a period of time. One exemplary embodiment of such light patterns and colors is depicted in FIG. 9A.

During the charging sequence of FIGS. 9A-9B, an annunciation of a system driven event may be required and/or a user-initiated pump status check may occur. If an AARM occurs while the pump is charging, at step 208 the charging pattern displayed by the indicator lights is replaced by the corresponding system driven event annunciation pattern. After the annunciation pattern is complete, the indicator lights can return to the charging pattern. However, if the user has not cleared the event (e.g., on the remote control device), the annunciation pattern may continually repeat until the event is cleared, at which point the indicator lights can return to and remain in the charging state. If a pump status check is initiated while the pump is charging such as by the user pressing the button 172 on the pump, at step 210 the current pump status can be displayed by the corresponding light pattern and/or color, as described above, for a predetermined period of time, such as, for example, 5 seconds. The indicator lights can then revert to the charging status. In some embodiments, the pump status displays only a single time each time the status check is requested.

FIG. 9B depicts further aspects of charging sequence 200. The charging pad 180 can also include an indicator, such as an LED light 184 that provides feedback on the charging process. At the initial step 202, the charging pad light 184 is off. After the pump 102 is placed on the charging pad at step 104, if the pump and the charging pad are properly aligned, the charging pad light 184 will illuminate at step 205 to indicate that charging has been initiated. This charging indication may be provided alternatively to or in addition to the vibratory indication provided by the pump described with respect to FIG. 9A. In embodiments, this charging indication is provided by only the pump and charging pad such that the remote control does not provide any indication of charging. After a predetermined period of time, such as, for example, 30 seconds, the charging pad light 184 turns off and the pump continues to charge with the indicator lights 174 changing to indicate the current battery level at step 206 as described above. In another embodiment, the charging pad light can remain illuminated during charging and change color to indicate a current charge of the battery.

Quick Bolus

Figure 10:
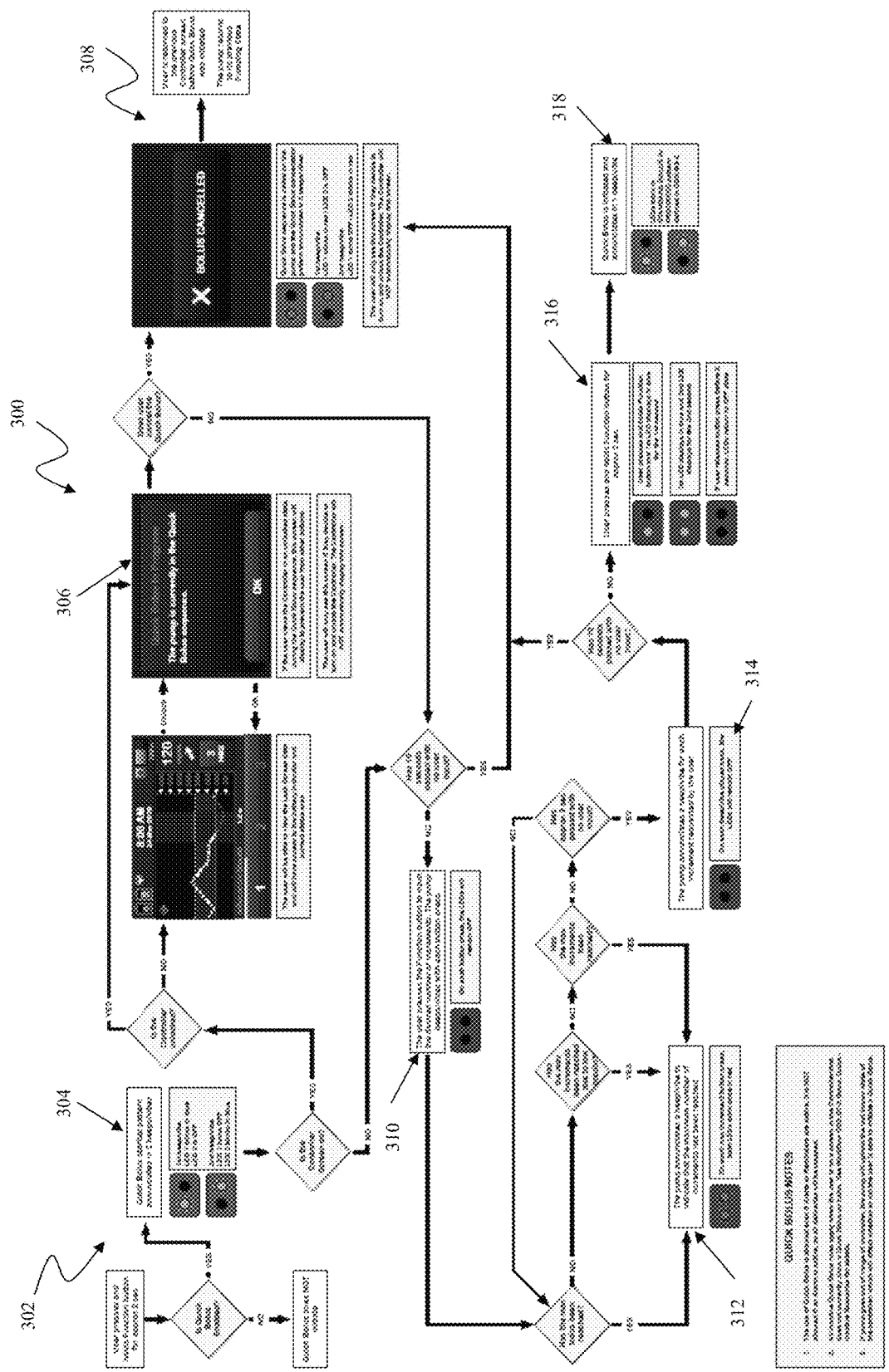
FIGS. 10-11B depict a procedure for programming a quick bolus for an infusion pump system according to the disclosure.

In some embodiments, pump 102 can be used to deliver a "quick" or "audio" bolus of medicament. A quick bolus enables programming of a bolus using a single button with the pump and/or remote control device, with a confirmation of the bolus provided with audible sounds, vibrations, visual indications or combinations thereof. FIG. 10 depicts one embodiment of a method 300 for programming of a quick bolus for a system including a pump 102 and a remote controller 170, 171 such as those described herein.

A quick bolus can be initiated at step 302 by user interaction with the button 172 on pump causing the system to determine if the quick bolus feature has been enabled. In this embodiment, a quick bolus is initiated by the user holding the button 172 down for approximately 2 seconds. If quick bolus has not been enabled, e.g., by activating a quick bolus option on the remote control menu, then the quick bolus feature does not initiate. If quick bolus is enabled, the quick bolus startup pattern is annunciated by the pump at step 304. In this embodiment, the quick bolus startup pattern includes an alternating pattern of lights blinking accompanied by beeps and/or vibrations in which the first indicator light illuminates with the second indicator light off followed by the second indicator light illuminating with the first indicator light off, with each light illuminating either only a single time or multiple times.

After the quick bolus startup pattern has been annunciated, if the user has turned on and unlocked the remote controller a quick bolus active screen can be displayed on the remote controller at step 306. If the controller is not unlocked, the lock screen will be displayed on the controller. The quick bolus screen includes only a single selectable close icon that can be selected to cancel the bolus in order to prevent the user from carrying out other actions with the controller that would interfere with the quick bolus. If the user does not turn on and unlock the controller, this screen will not appear. If the user does select the close item to cancel the quick bolus, a bolus cancelled screen can be displayed on the controller and the remote can issue a quick bolus cancellation annunciation at step 308. In this embodiment, the quick bolus cancellation pattern is identical to the quick bolus startup pattern except that a different color is displayed by the indicator lights (e.g., red for cancellation and blue for startup). The remote control can then be returned back to the previous screen that was displayed prior to initiation of the quick bolus and the pump can return to the previous pumping state. The quick bolus can also be cancelled if there is no user input received (i.e., another press of the pump button) for a predetermined time after the quick bolus start up pattern is annunciated, such as, for example, 10 seconds.

At step 310, the user can increase the quick bolus amount by pressing the button 172 on the pump, with each button press corresponding to a predetermined increment. The pump can beep and/or vibrate to indicate each button press and the indicator lights can further provide an indication of each button press. Alternatively, the pump may beep and/or vibrate with each button press but the lights will remain off. If a maximum number of bolus increments has been reached during programming, at step 312 that pump can provide a maximum increment annunciation, which, in this embodiment, causes the indicator lights to flash red after each button press after reaching the maximum. The maximum increment amount can be reached in a number of ways including one or more of reaching a maximum bolus amount of a single bolus, reaching a total maximum bolus amount that can be delivered over a set time period such as an hour, the insulin reservoir being too low to deliver additional increments and/or a preset maximum number of increments for a quick bolus. After programming of the quick bolus has been initiated, if a predetermined time passes without further user input, i.e., button presses, at step 314 the pump annunciates the quick bolus amount. In one embodiment, the quick bolus amount annunciation issues one beep and/or vibration per programmed bolus increment with the indicator lights blinking along with each beep and/or vibration. Alternatively, the indicator lights may remain off during the annunciation.

Following annunciation of the quick bolus amount, the user may be required to confirm the quick bolus amount prior to delivery. In this embodiment, at step 316 the user confirms the quick bolus amount by holding the button 172 on the pump down for a predetermined period of time, such as, for example, 2 seconds. The indicator lights 174 on the pump can indicate the status of the confirmation as shown in FIG. 10. When the confirmation is received, the pump can provide a beep and/or vibration to indicate that delivery of the quick bolus has been initiated and the indicator lights 174 can indicate the delivery of the bolus in an ongoing manner as described previously at step 318.

Figure 11A:
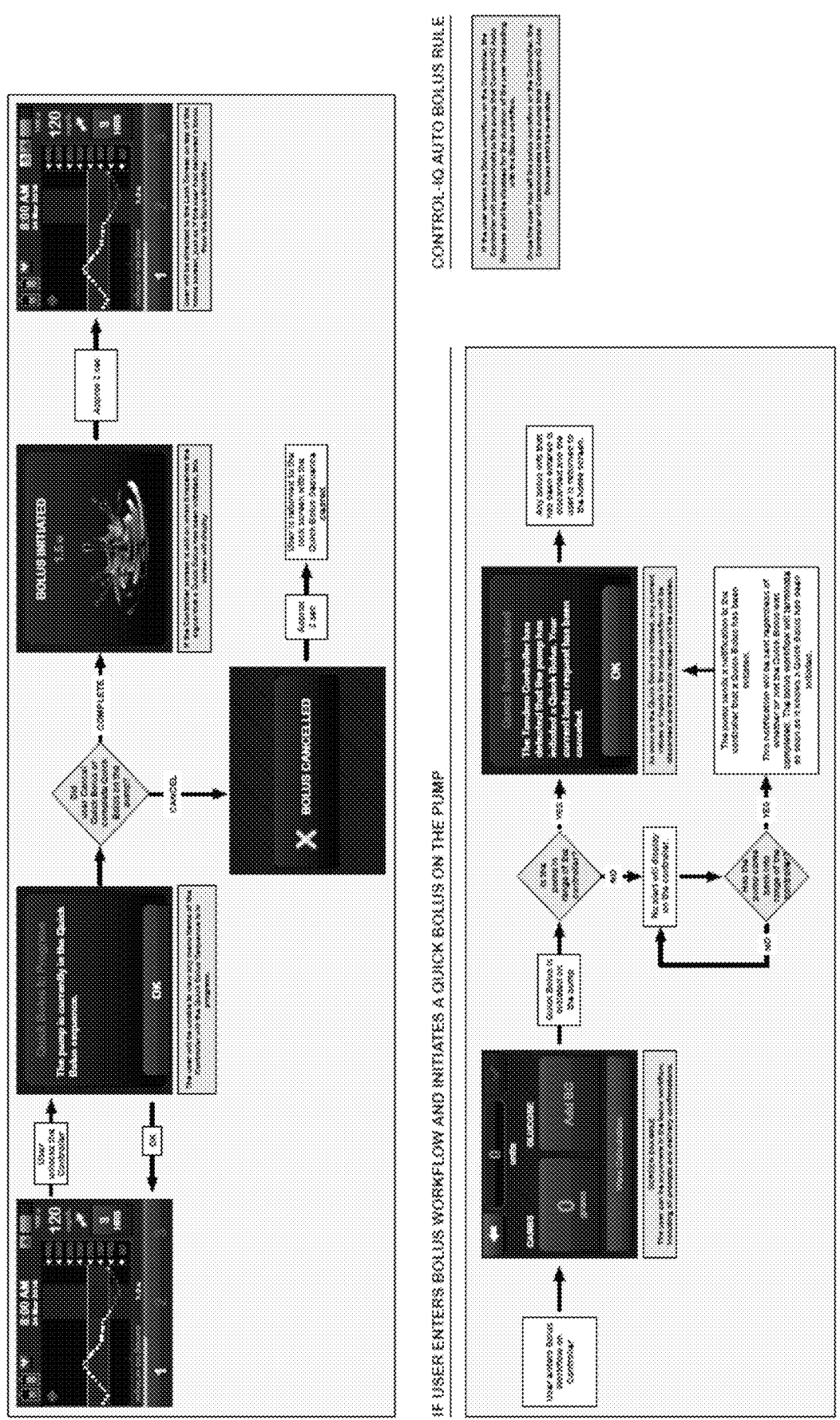

FIG. 11A depicts a series of screens that can be displayed on the remote controller if the controller is unlocked during the quick bolus sequence or if the user initiates a quick bolus with a bolus workflow open on the controller. Generally, no interaction with the controller screen is allowed when programming a quick bolus. Thus, when the quick bolus active screen is displayed, the user can only cancel the quick bolus by pressing the close/OK item. Similarly, the user may still program a quick bolus if the bolus workflow screen is open, but the user will then be notified that a quick bolus has been initiated with the pump and any programmed values on the remote will be discarded. Once a quick bolus has been programmed and delivery initiated, the user can also be notified of the quick bolus on the controller as shown in FIG. 11A.

Figure 11B:
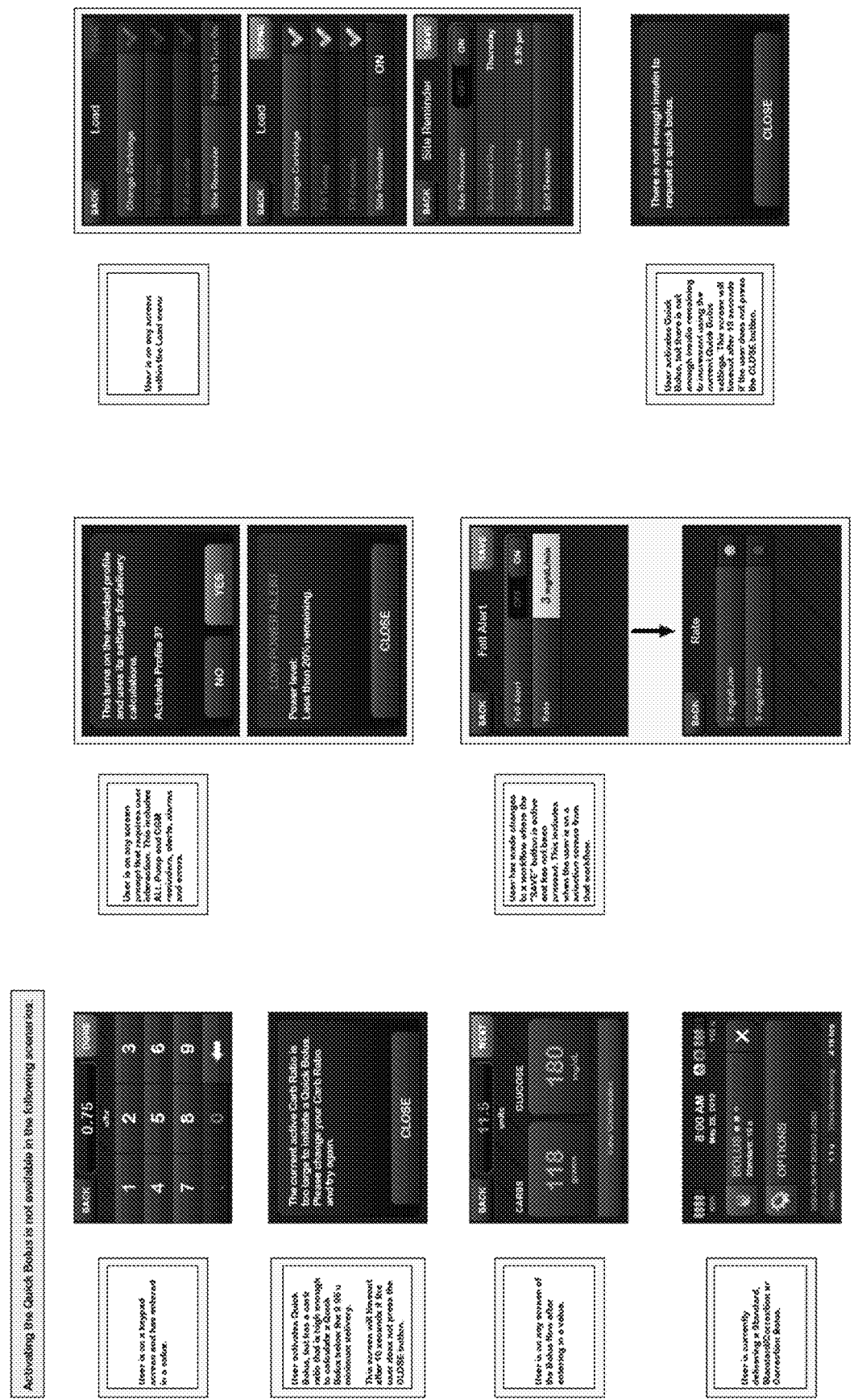

In some embodiments, programming of a quick bolus with the pump is not available if the remote control device is on certain menu screens. FIG. 11B depicts a number of remote control screens and/or conditions that will make the quick bolus feature of the pump unavailable if the remote control is on one of these screens and/or one of the conditions is present in the system.

Alarm Screens

Figure 12A:
FIGS. 12A-12E depict various screens that can be displayed on a remote control device for an infusion pump system according to the disclosure.
Figure 12B:
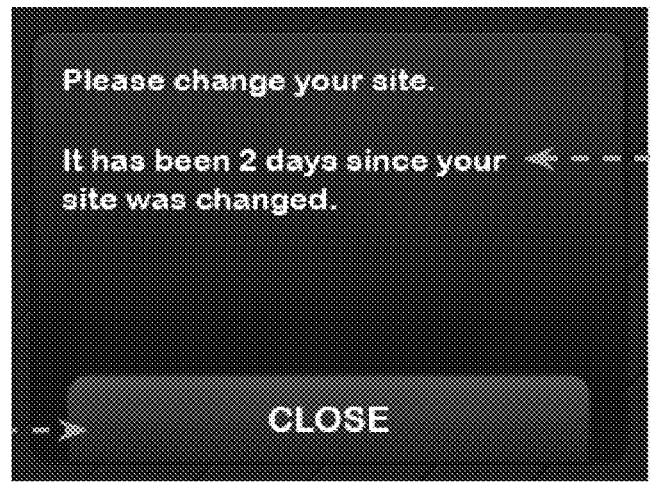
Figure 12C:
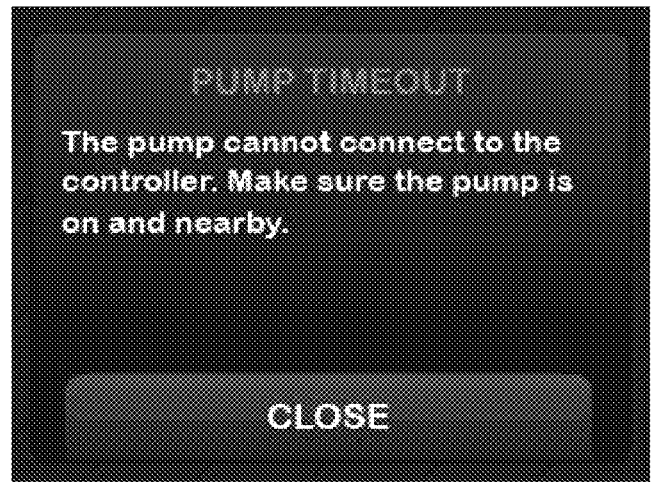
Figure 12D:
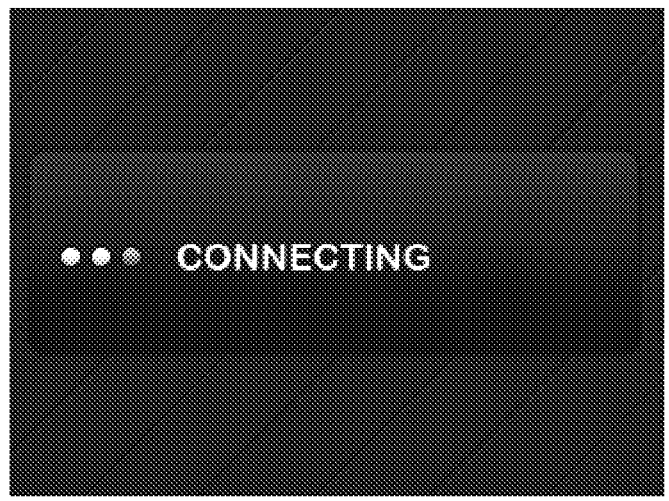
Figure 12E:
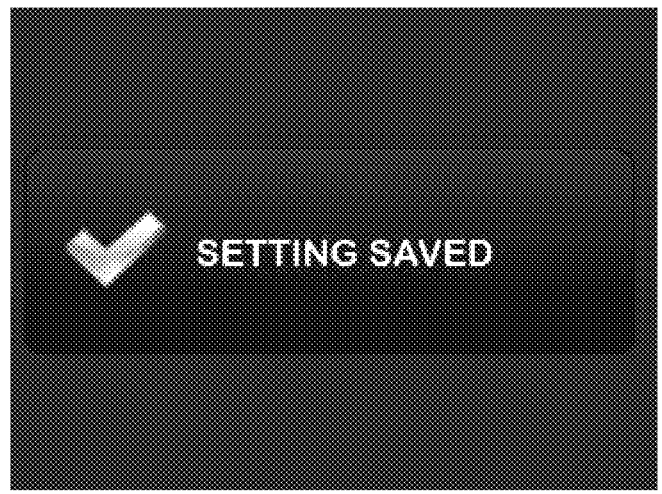

Due to the lack of a display screen on pumps such as pump 102 described above, information relating to the pump including pump AARMs can be conveyed on the display screen of another device such as a remote control device 170, 171. For example, a cartridge alarm is depicted in FIG. 12A. If at any point the push rod of the pump does not operate correctly and a button is pressed on the remote control to move forward in a workflow, the depicted cartridge alarm can display. When the user selects the close item on the screen, the remote control will display the load menu (discussed in more detail below) to reconnect the cartridge. FIG. 12B depicts a site reminder screen. If the site reminder feature that reminds the user to rotate the user's infusion site after a set amount of time (e.g., 2 days) is on, when the set amount of time has elapsed, this reminder can appear on the screen of the remote controller. The pump timeout screen depicted in FIG. 12C is displayed on the remote to indicate that the pump cannot connect to the remote controller. This screen can display if the pump goes out of range of the controller and a button is pressed on the remote to save settings or confirm a delivery state. In some embodiments, a connecting screen depicted in FIG. 12D can be displayed while the remote is attempting to detect the pump. If the remote does successfully connect to the pump, a setting saved screen in FIG. 12E can be displayed to indicate the successfully saved programming operation.

Snooze Feature

Figure 13A:
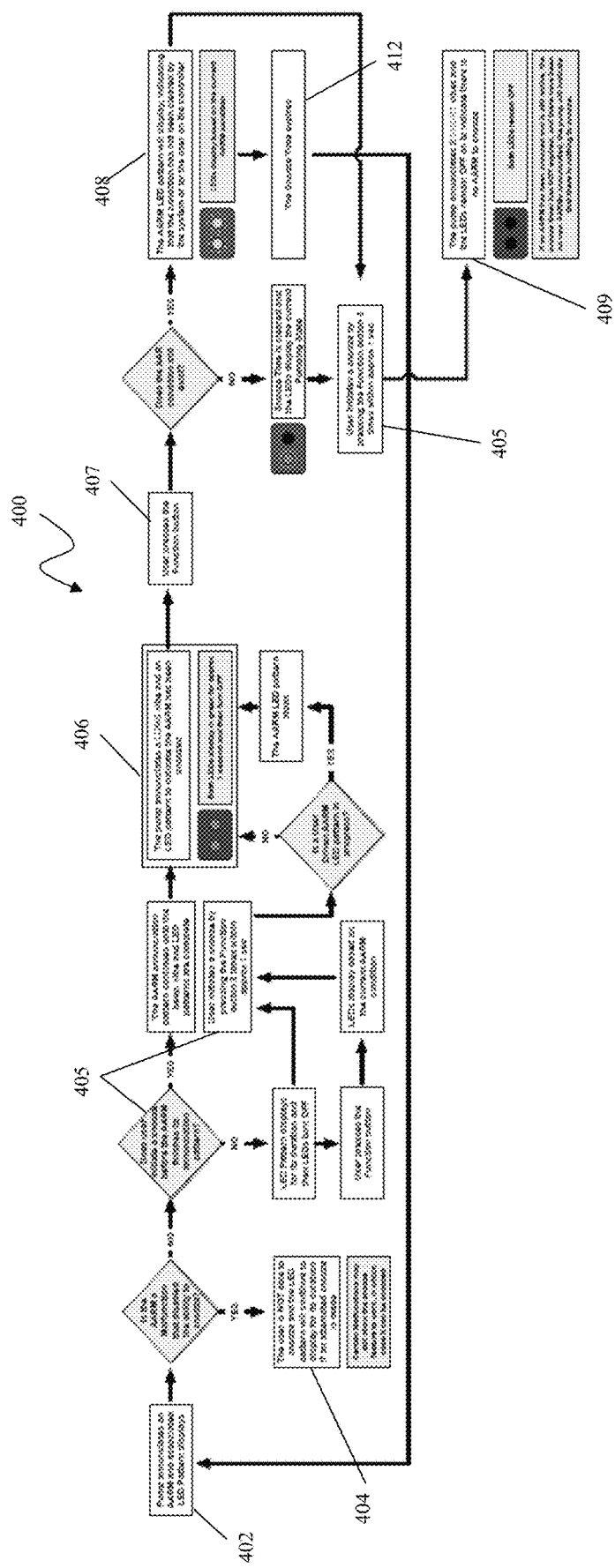
FIGS. 13A-13B depict procedures for executing a snooze feature of an infusion pump system according to the disclosure.

FIG. 13A depicts steps for executing a snooze feature 400 that may be available in certain embodiments of infusion pump systems as described herein. The snooze feature becomes potentially available when, at step 402, the pump annunciates an AARM with a corresponding indicator light and/or beep/vibration pattern. In some embodiments, if the AARM is a malfunction, the snooze feature may be disabled at step 404 such that the annunciation of the malfunction will continue to display. In some embodiments, certain malfunctions may still allow use of the snooze feature, such that the method would continue as depicted in FIG. 13A as if the AARM were not a malfunction. The snooze feature can be activated with a predefined interaction with the button 172 on the pump at step 405. In one embodiment, the snooze feature is activated by the user pressing the button three times within a short period of time, such as one second. This can be done either during the original annunciation pattern or if the user presses the button to check the current status and the pattern is displayed to indicate the AARM as the current device status. In some embodiments, an AARM can be snoozed at any time the AARM is active, not only when the AARM is being annunciated In some embodiments, the AARM annunciation will finish prior to executing the snooze function that will then keep the AARM from repeating. If the AARM is not a malfunction (or a malfunction that permits the snooze feature), the pump will annunciate a unique indicator light, beep and/or vibration pattern predefined as corresponding to the snooze feature to indicate that the AARM has been snoozed at step 406.

After the snooze feature has been activated, the user may again press the pump button 172 at step 407. If the AARM condition no longer exists, the snooze feature is cleared and the pump with annunciate the current pumping state as described above. If the user then enters the snooze activation input in an attempt to snooze the AARM that is no longer present, the pump can annunciate a unique indicator light, beep and/or vibe pattern that indicates there is no AARM to snooze at step 409. If the AARM condition is still active when the user presses the button at step 407, the annunciation pattern corresponding to the AARM will be displayed at step 408 to indicate that the condition has not been cleared by the system or by the user on the controller. The snooze feature is set to last for a predetermined period of time. When the period of time expires without the AARM being cleared at step 412, the system reverts back to step 402 and again annunciates the AARM. In some embodiments, only the pump can be used to activate the snooze feature in response to an AARM such that the remote controller cannot activate the snooze feature.

Figure 13B:
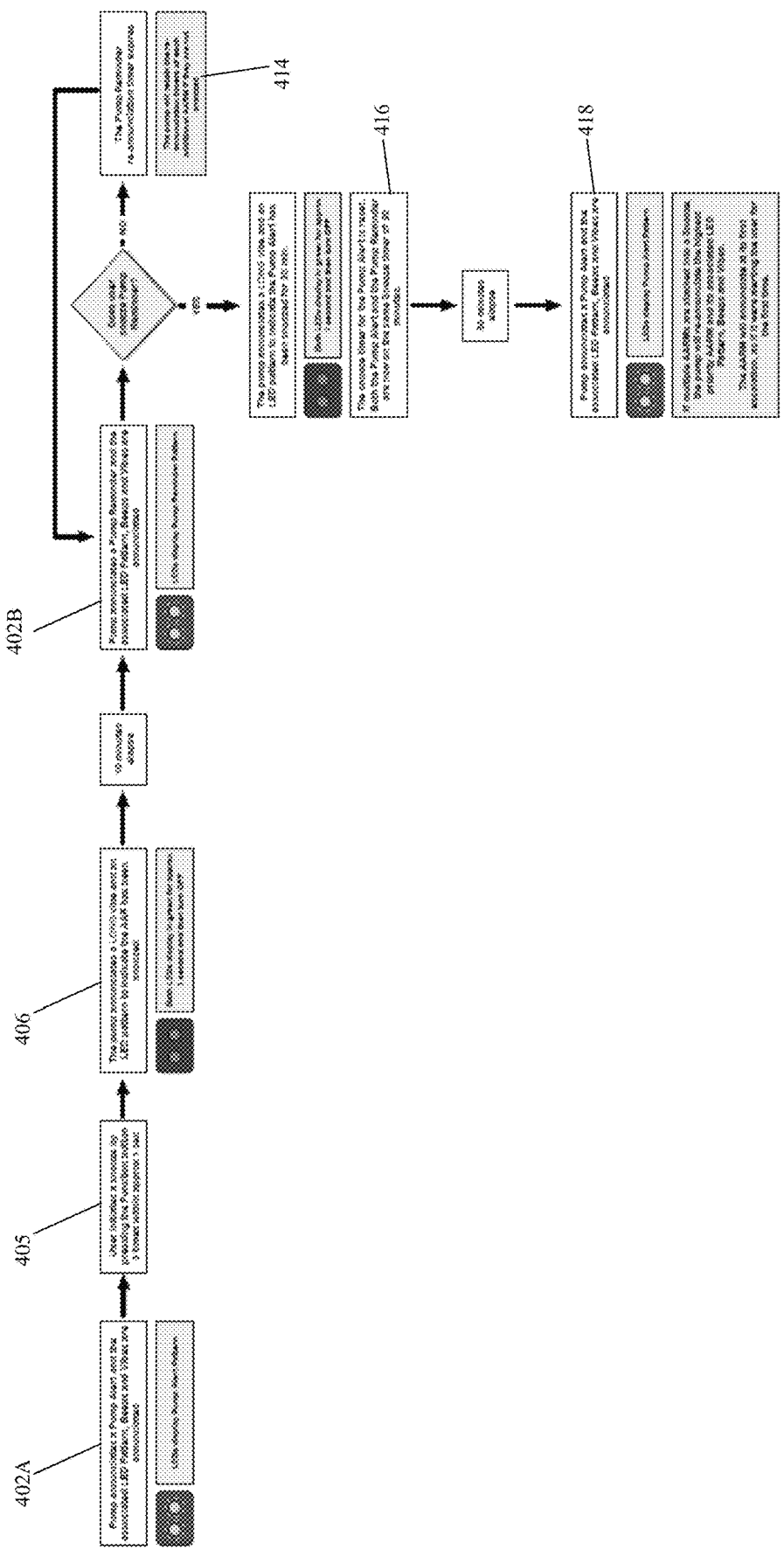

FIG. 13B depicts steps for executing a snooze feature 400 when there are multiple AARMs present. If the pump annunciates a first alarm, alert or reminder, such as an alert, at step 402A and the user enters the snooze activation input at step 405, then the pump will issue the snooze annunciation at step 406 as indicated above. When a second alarm, alert or reminder, such as a reminder, is later annunciated at step 402B (e.g., 10 minutes later or any time less than the programmed snooze time), the system determines if the user has entered the snooze activation input for the reminder. If not, the pump will retain the re-annunciation timer of each reminder, alert and alarm at step 414. In the described example in which the initial alert at step 402A was snoozed for 30 minutes and 10 minutes had passed, the alert would be annunciated again after another 20 minutes. If the reminder of step 402B is snoozed, the pump will issue the snooze annunciation pattern and reset the snooze timer for the alert at step 416 such that now the alert from step 402A and the reminder from step 402B will be on the same preprogrammed snooze time (e.g., 30 minutes.) After the snooze period elapses, both the alert and the reminder will be annunciated at step 418. When multiple AARMS are snoozed, the pump with annunciate the highest priority AARM first, and so on.

Figure 14:
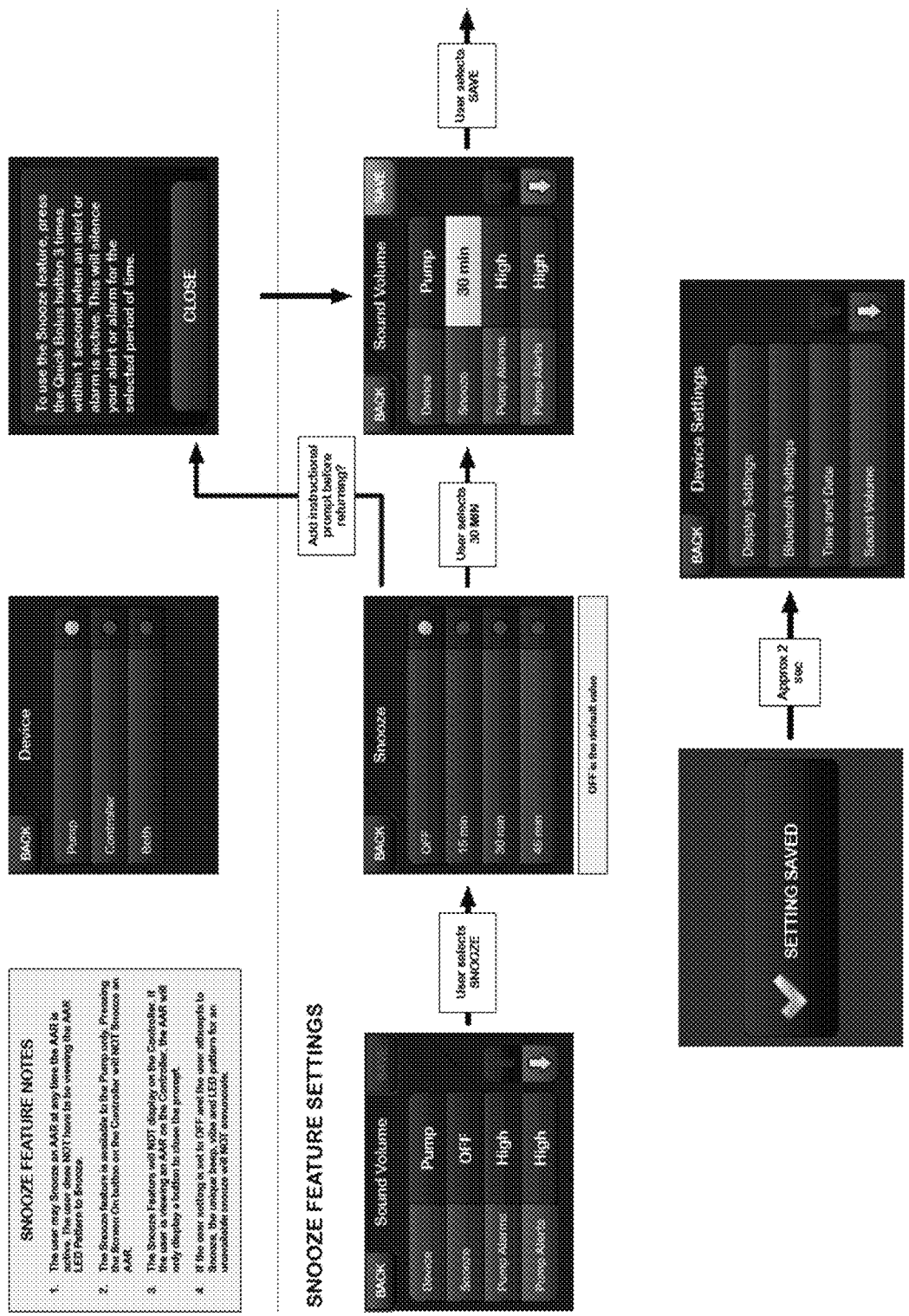
FIG. 14 depicts various screens that can be displayed on a remote control device for an infusion pump system according to the disclosure.

The snooze feature of the pump described with respect to FIGS. 13A-13B above will only occur if the remote controller has been used to set the snooze feature to ON. FIG. 14 depicts a series of screens that can be navigated on the remote controller to activate the snooze feature. These menu screens enable the user to turn the snooze feature on or off as well as to set a time period for the snooze feature. In some embodiments, no screens announcing or providing status relating to the snooze feature are displayed on the remote controller when the snooze feature is activated to snooze a pump AARM.

Controller Shutdown

Figure 15A:
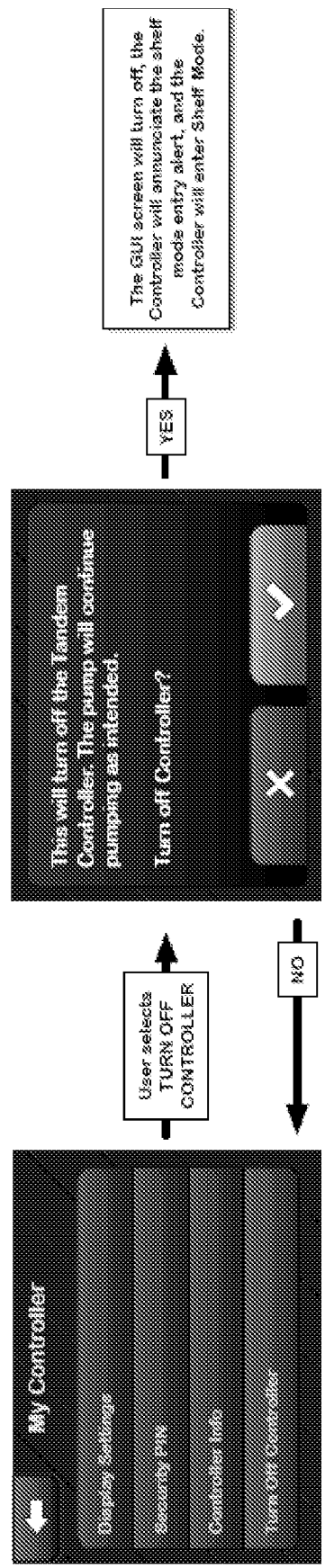
FIG. 15A depicts various screens that can be displayed on a remote control device for an infusion pump system according to the disclosure.
Figure 15B:
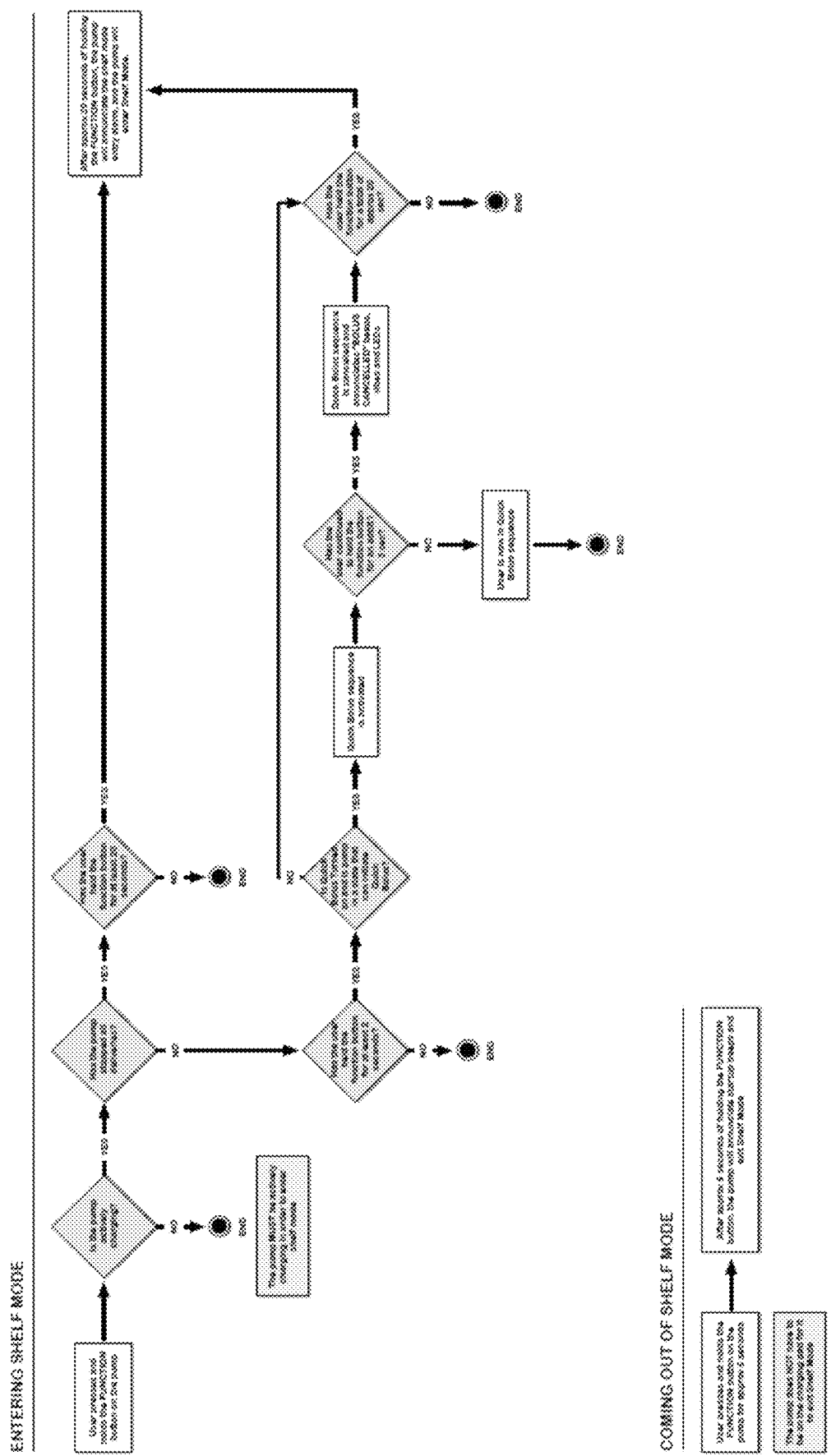
FIG. 15B depicts procedures for entering and exiting a shelf mode of an infusion pump according to the disclosure.

Although in embodiments described herein, the remote control device 170, 171 is the primary means for programming and controlling the pump 102, if the controller is shut down the pump can continue to operate according to the programming instructions existing at the time the controller is shut down. FIG. 15A depicts menu screens that can be navigated on the controller to turn off the remote control device, upon which the remote control device will enter the shelf mode. FIG. 15B depicts procedures for entering and exiting shelf mode.

Pump Functions

For user-wearable infusion pumps utilizing refillable and/or replaceable cartridges, a number of functions including replacing and/or refilling the cartridge, filling the infusion tubing and filling the cannula must be regularly carried out for continual use of the pump. Typically, instructions for carrying out these functions are presented on the display screen of the pump to guide the user through proper execution of each function. However, a pump such as pump 102 does not include a display screen. Guidance for carrying out pump functions can therefore be provided on the display of the corresponding remote control device 170, 171.

Figure 16A:
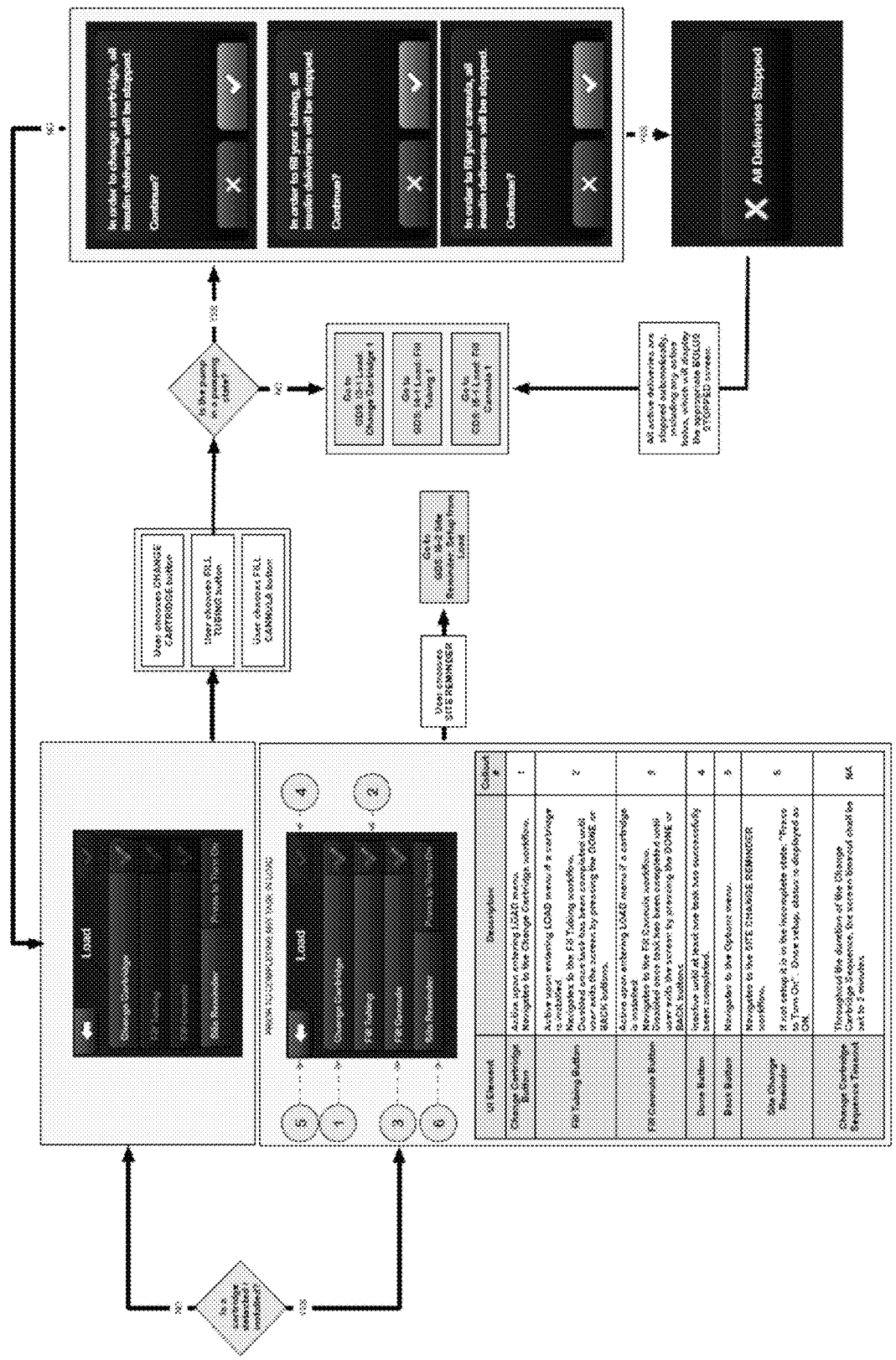
FIGS. 16A-16D depict various screens that can be displayed on a remote control device for an infusion pump system according to the disclosure.
Figure 16B:
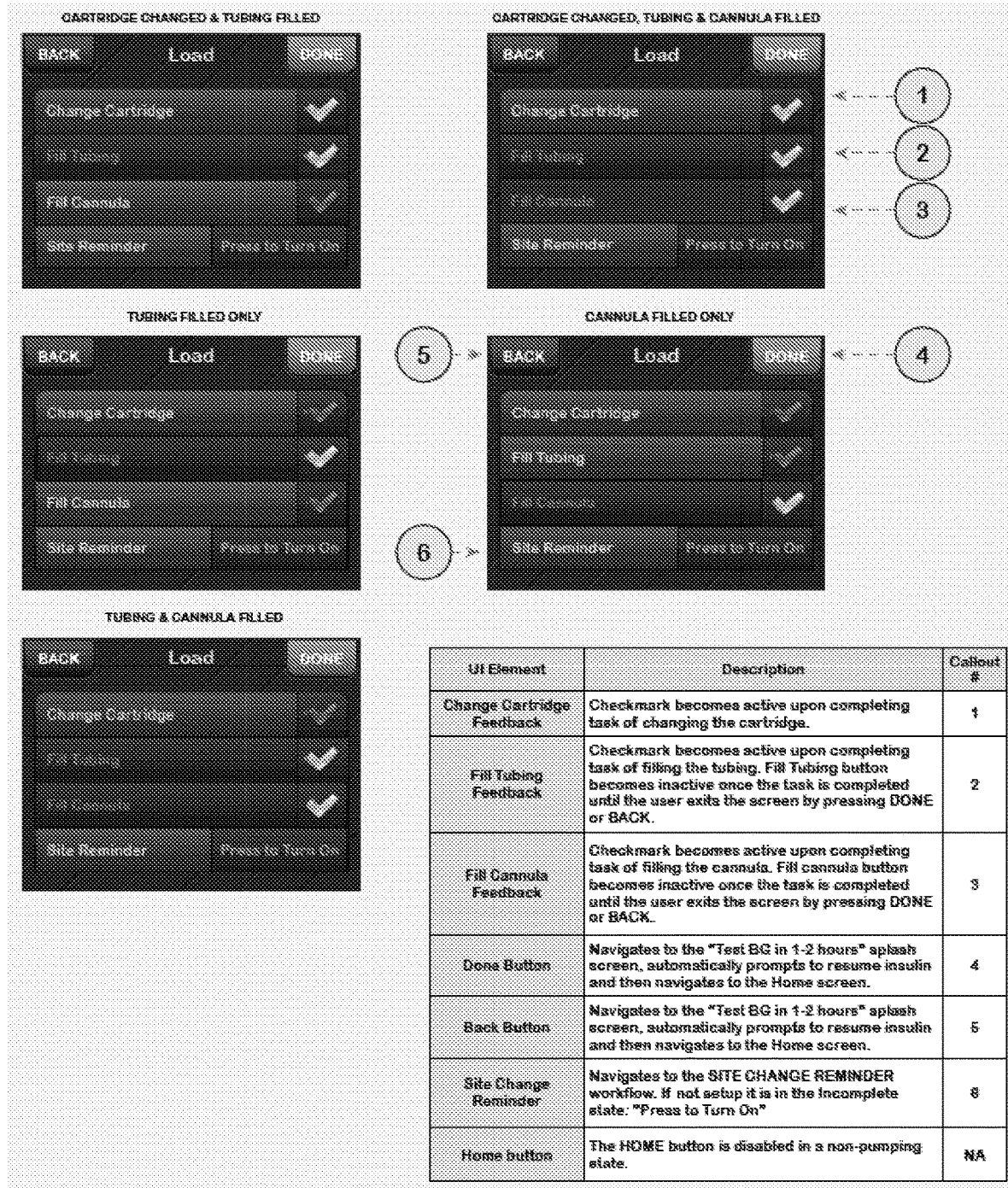
Figure 16C:
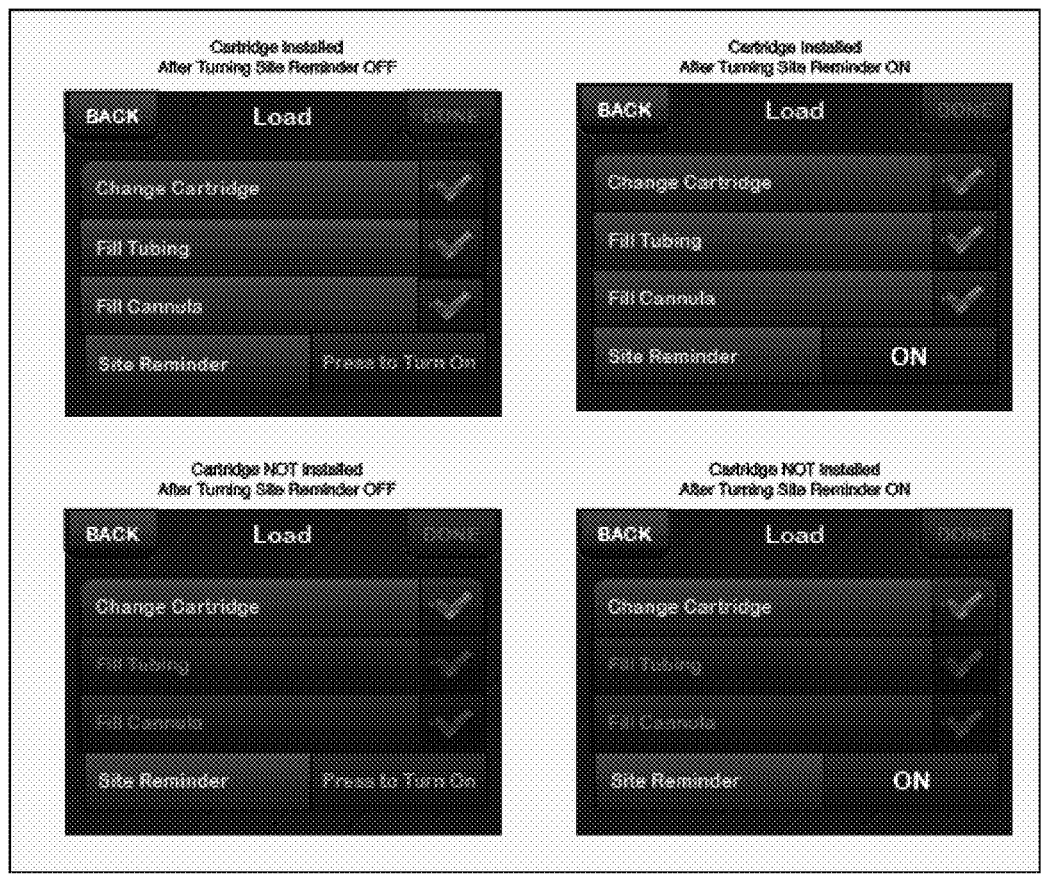
Figure 16D:
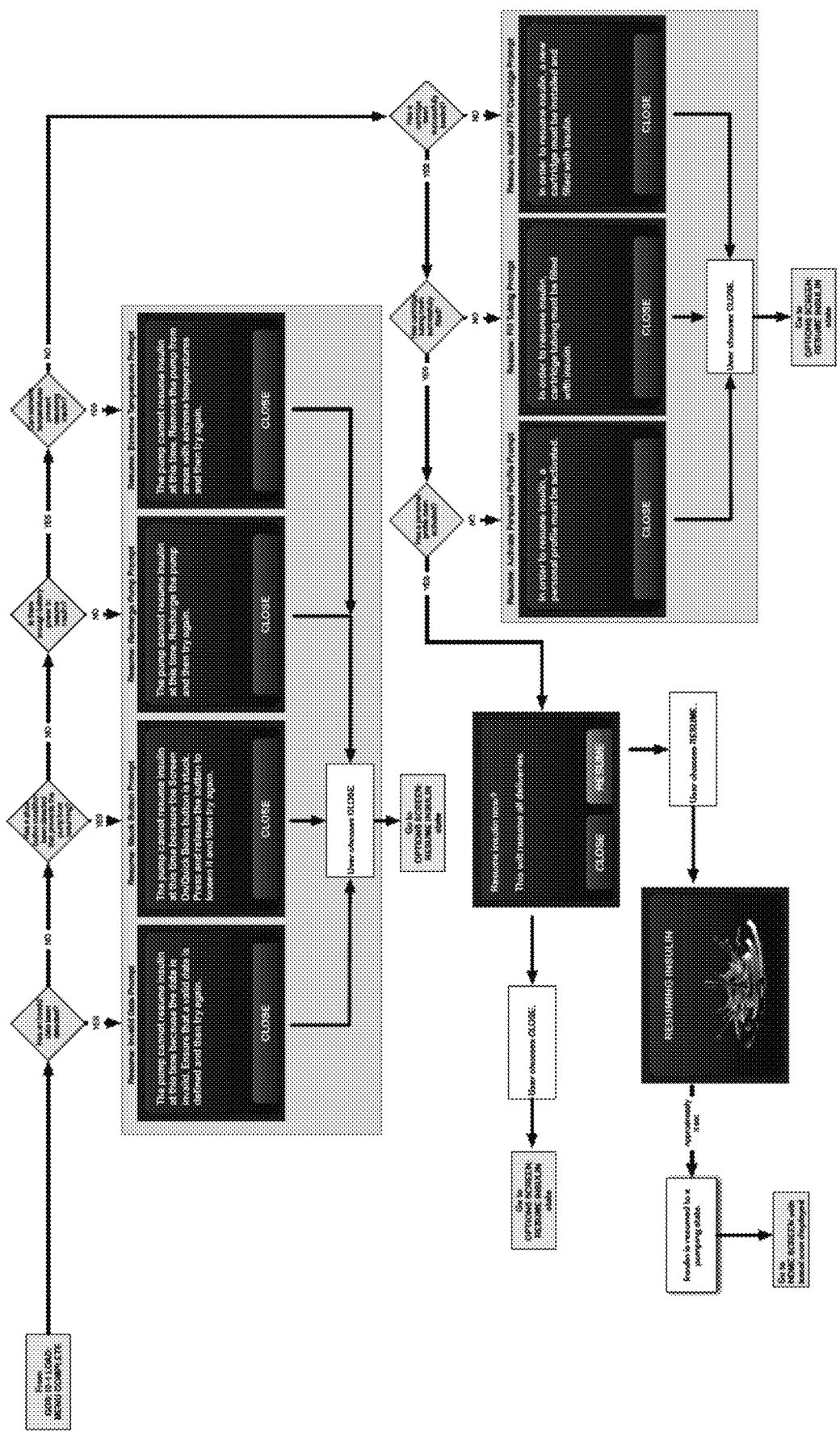

FIGS. 16A-20B depict display screens that can be displayed on a remote control device 170, 171 for guiding the user through various pump functions according to embodiments. FIG. 16A depicts a load menu prior to the user completing the required cartridge loading tasks. As indicated in the figure, certain menu items (e.g., fill tubing) are only available for selection after certain prerequisite items are completed (e.g., installation of a cartridge). FIG. 16B depicts a progression through the load menu as the user completes the required tasks. Additional load screens are depicted in FIG. 16C. FIG. 16D depicts a flow diagram and series of menu screens for display on the remote controller for resuming insulin following completion of one or more cartridge change tasks.

Figure 17A:
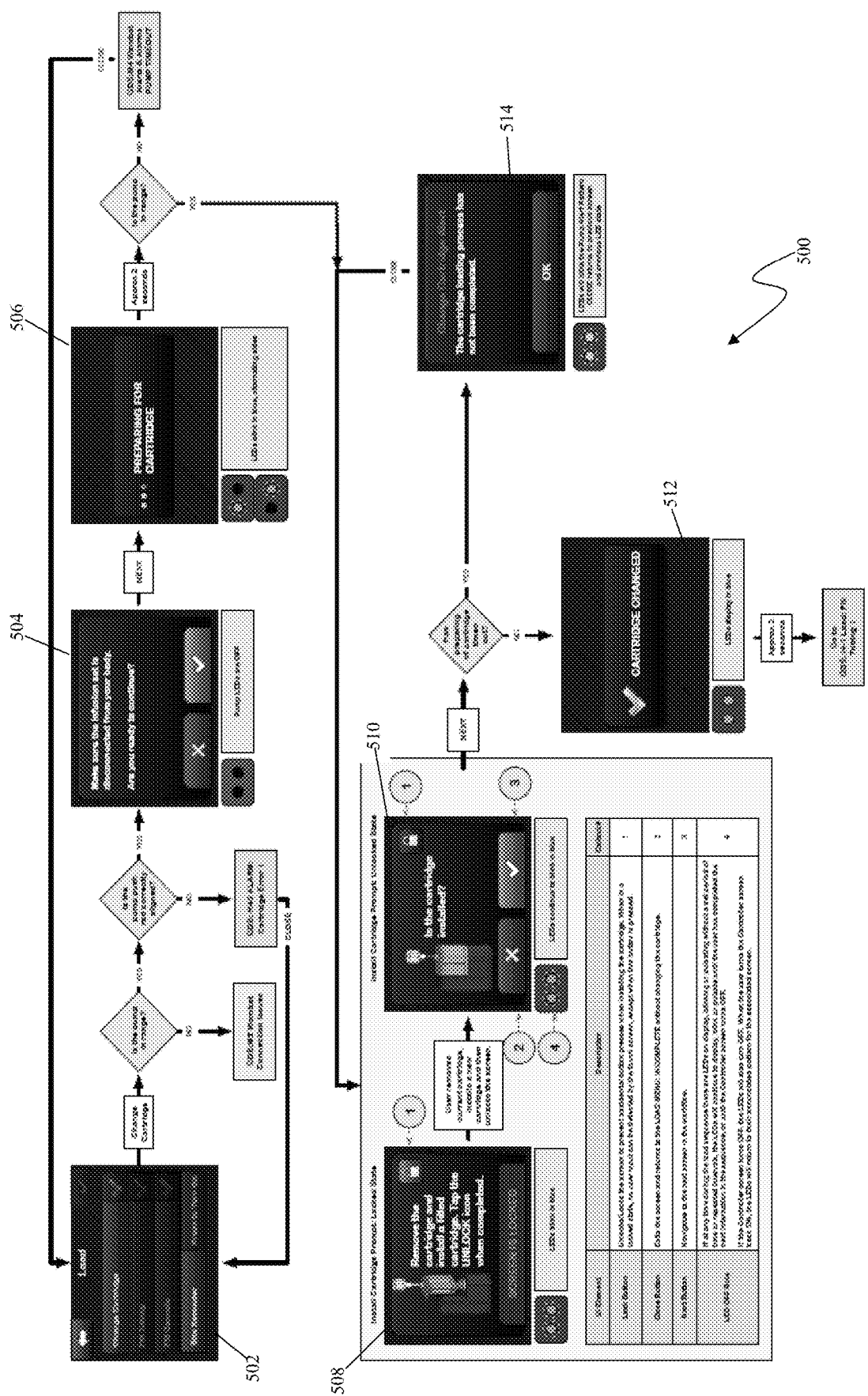
FIGS. 17A-17B depict a procedure for changing a cartridge of an infusion pump system and corresponding menu screens according to the disclosure.

FIG. 17A depicts a series of display screens that can be presented on the remote controller to guide the user through a cartridge changing process 500 according to an embodiment. At step 502, the user selects the change cartridge item from the load menu on the remote controller. The controller then determines if the pump is in range and if the pump push rod is correctly aligned to remove the cartridge and receive a new/refilled cartridge. If the pump is not in range, the pump timeout alarm of FIG. 12C or other message notifying the user of a connection error is displayed and if the push rod is not correctly aligned the cartridge alarm of FIG. 12A or other cartridge error message is displayed, and the change cartridge sequence 500 cannot be continued until the issue causing the alarm is rectified. If both inquiries are satisfied, the controller displays an instruction for the user to disconnect the infusion set from the user's body at step 504. When the user confirms the disconnection, the controller at step 506 presents a screen indicating that the cartridge is being prepared to be removed. The indicator lights 174 of the pump can also provide an indication that the cartridge is being prepared to be removed as shown in FIG. 17A.

Once the cartridge is prepared, the user can be prompted to remove the current cartridge and install a filled cartridge at step 508. At this stage, the remote controller screen can be locked to prevent accidental button presses while the cartridge is installed. In the locked state, no user input can be detected by the touch screen, except when the lock icon is pressed. The indicator lights can also provide an indication of the locked state. After the cartridge has been changed and the user presses the lock icon, the screen is unlocked at step 510. If the user selects the close item ("X"), the controller will revert to the load menu incomplete screen of FIG. 16A without completing the cartridge change process. If the user selects the next item (check mark), the system will determine if the cartridge change timed out, and, if not, display a cartridge changed screen and corresponding indicator light pattern at step 512. The system can then proceed to the fill tubing process described below. If the cartridge change did time out, the cartridge change alert screen and a corresponding indicator light pattern can be displayed at step 514. In one embodiment, the process times out if three or more minutes pass without user interaction with the pump and/or remote control.

Figure 17B:
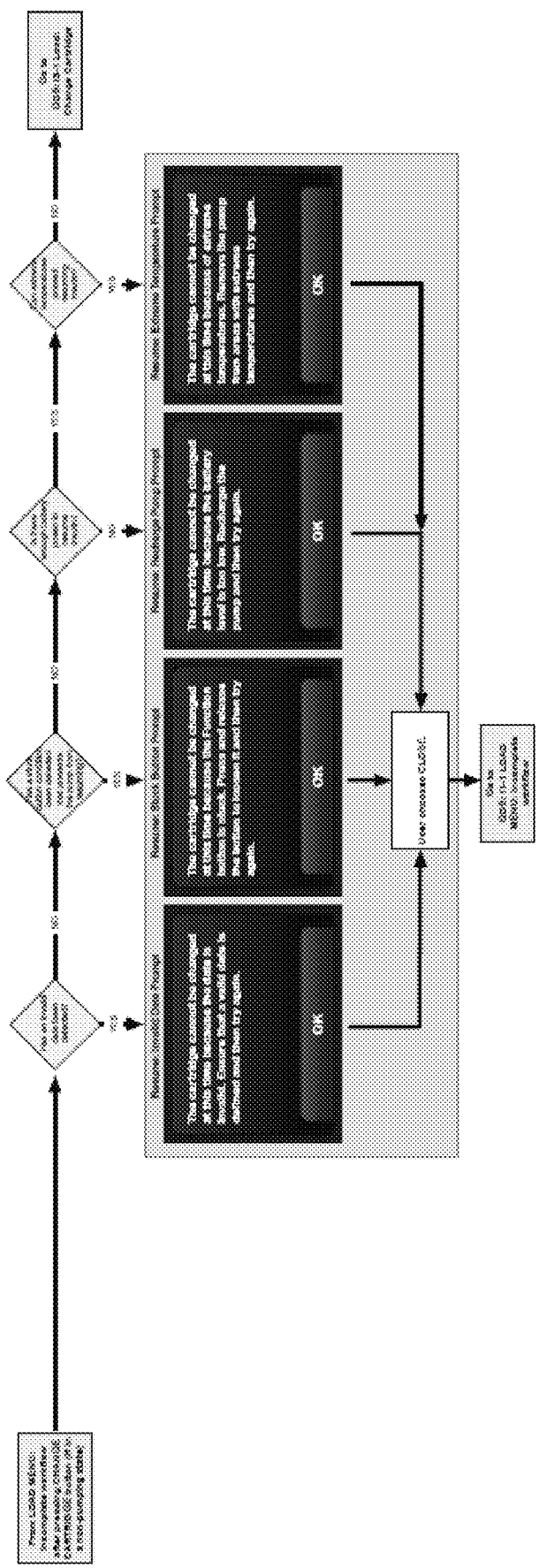

There are a number of devices errors than can prevent the remote controller from entering the cartridge change menu sequence 500 described above when the change cartridge item is selected. These include, for example, the date set on the remote controller being invalid, the function button on the pump being stuck, the battery power of the pump being too low and detection of an extreme temperature. Corresponding screens for these errors that can be displayed on the remote controller are depicted in FIG. 17B.

Figure 18A:
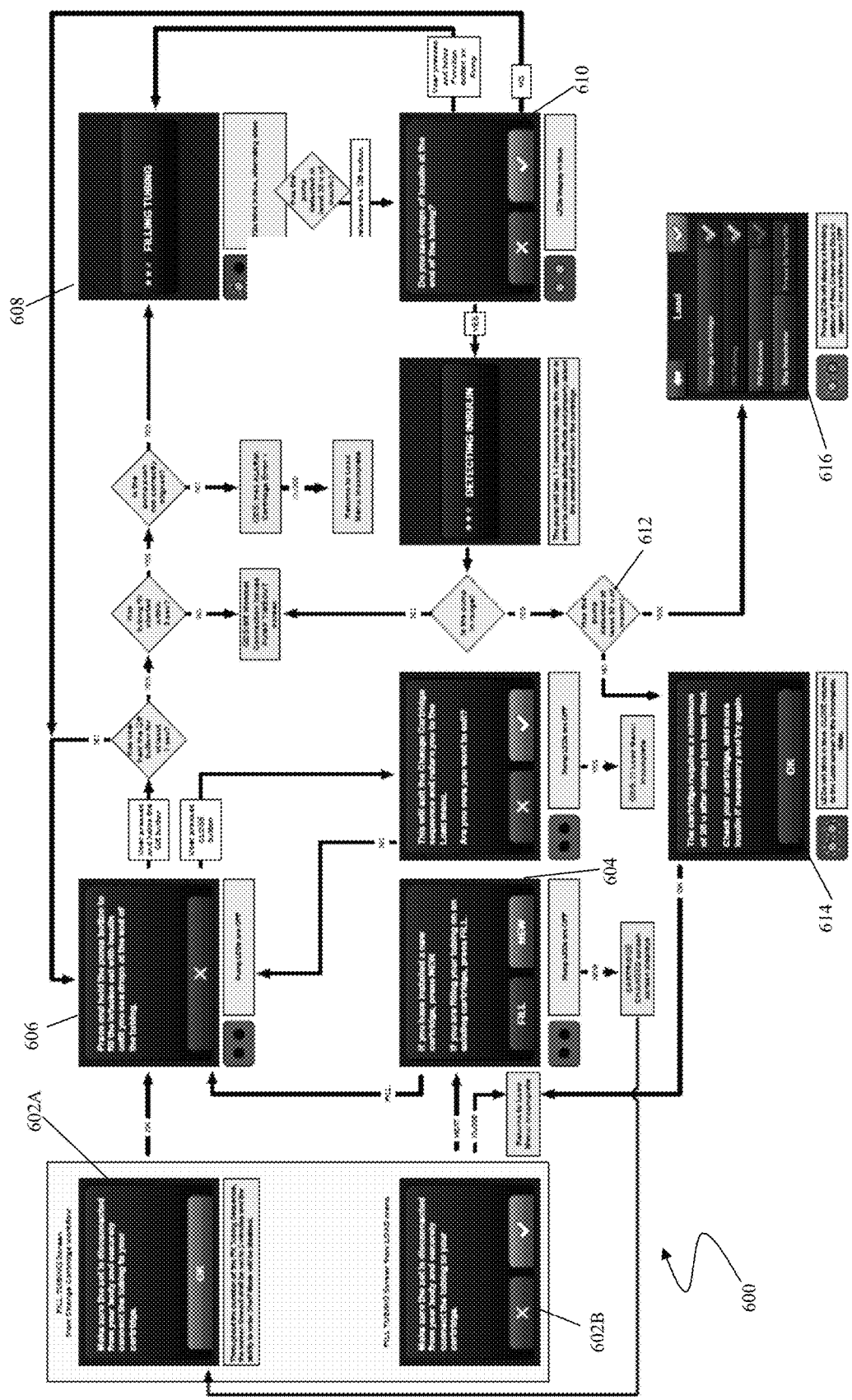
FIGS. 18A-18B depict a procedure for filling tubing of an infusion pump system and corresponding menu screens according to the disclosure.
Figure 18B:
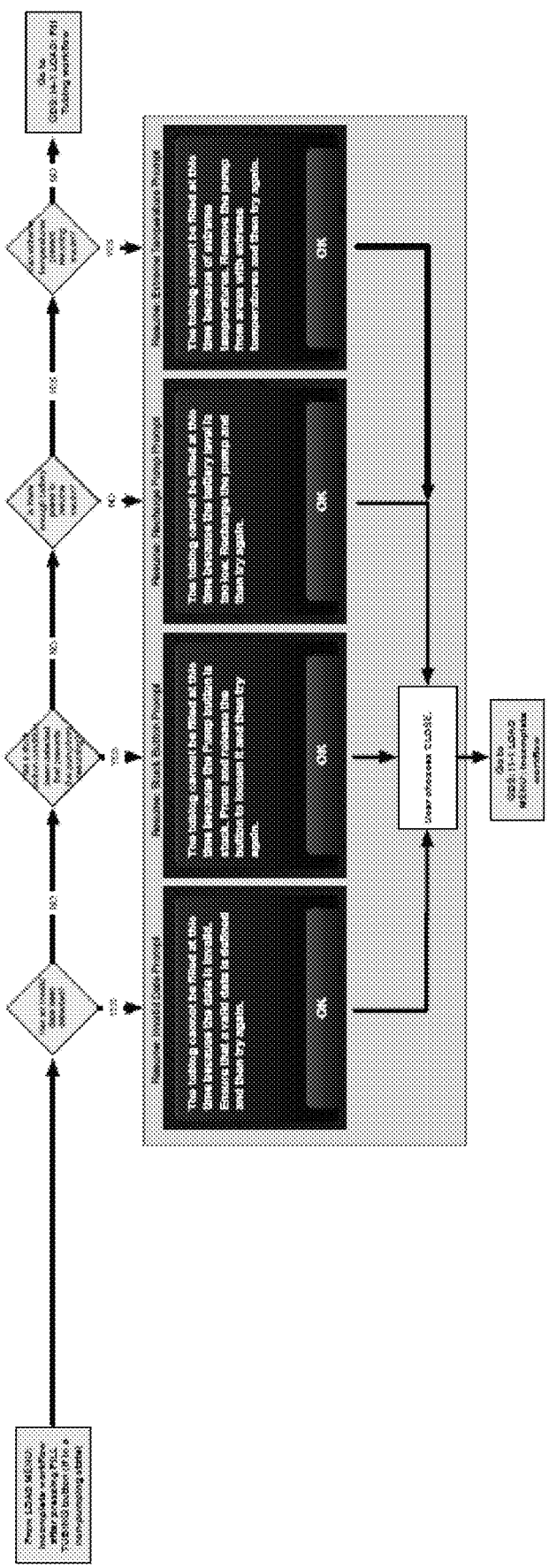

A fill tubing sequence 600 and corresponding display screens that can be entered following a cartridge change according to an embodiment is depicted in FIG. 18A. The fill tubing sequence can be entered either following the cartridge change sequence 500 at step 602A or from the load menu at step 602B. If the user enters the fill tubing sequence from the load menu in step 602B, then at step 604 the user is requested to enter whether a new cartridge has been installed or the user is filling the tubing on an existing cartridge. If the user selects the new item, the user is diverted to step 602A for entering the fill tubing sequence from the change cartridge sequence. If the user selects the fill item at step 606 instructions for filling the tubing are displayed. The instructions at step 606 are also displayed when the user proceeds from the initial fill tubing screen entered from the cartridge change sequence at step 602A.

In this embodiment, the instructions for filling the tubing include pressing and holding the button 172 on the pump until drops of insulin can be seen at the end of the tubing. If the device is properly functioning to fill the tubing, at step 608 a screen on the remote controller and corresponding indicator light pattern on the pump can indicate that the tubing is being filled. When the user releases the pump button, at step 610 a screen can be displayed asking the user if drops of insulin can be seen at the end of the tubing. If the user selects the NO or "X" item, the sequence will revert back to step 606 for filling instructions. If the user selects the YES or check mark item, the system will determine if there are at least 50 units of insulin in the cartridge at step 612. If not, the user will be notified at step 614 that the cartridge requires a minimum number units, such as, for example, 30 units, 50 units, etc., after the tubing has been filled and the system will exit the fill tubing sequence back to the load screen indicating that the fill tubing item has not been completed. If there are greater than the minimum number of units, the system at step 616 will return to the load menu with the fill tubing item marked as completed. As indicated in FIG. 18A, a number of additional safety and/or error checks can occur throughout the fill tubing sequence 600 that can cause the system to exit the sequence, with corresponding error screens such as those depicted in FIG. 18B.

Figure 19A:
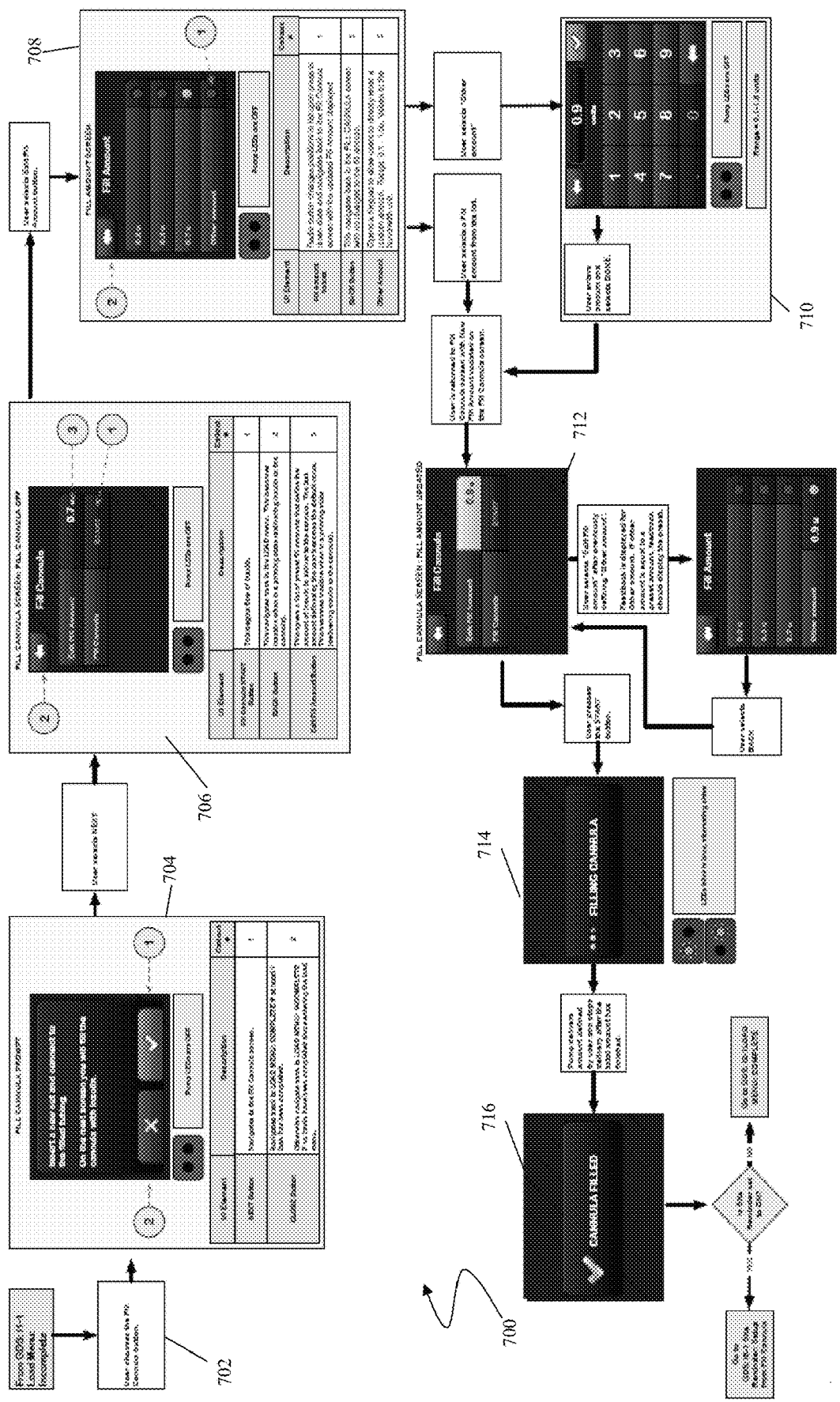
FIGS. 19A-19B depict a procedure for filling a cannula of an infusion pump system and corresponding menu screens according to the disclosure.
Figure 19B:
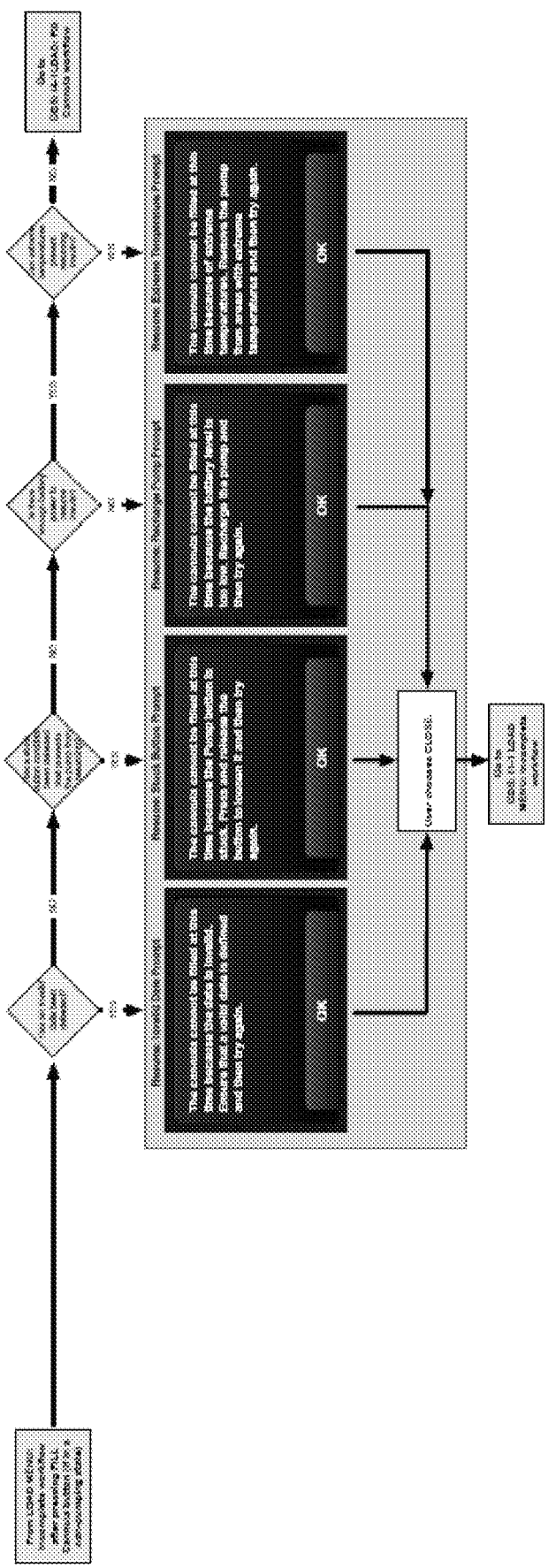

A fill cannula sequence 700 and corresponding display screens that can be entered following a cartridge change according to an embodiment is depicted in FIG. 19A. At step 702, the user initiates the fill cannula sequence by selecting the fill cannula item from the load menu. At step 704, the user is instructed to insert a new infusion set and connect the infusion set to the filled tubing. After connecting the infusion set and selecting the next (or check mark) item, the user is presented with a fill cannula screen at step 706. The fill amount can be edited by selecting the edit fill amount item and selecting an amount on a fill amount screen at step 708. If the user wishes to enter a different amount than those displayed, the user can select the other amount item and enter an amount using a numeric keypad at step 710. The user is then returned to the fill cannula screen at step 712 with the updated fill amount displayed. Selection of the start item at step 712 will then start filling the cannula and a notification screen and indicator light pattern can display at step 714. After completion of the fill process, a Cannula Filled screen can be presented to the user at step 716.

In another embodiment, prior to providing the Cannula Filled screen, an amount filled item can display to the user the amount that has been filled at any given time, counting up to the total fill amount previously entered. Progress indicators can also indicate that the fill is in progress by changing colors. If the user selects a stop item on the fill cannula page, a screen notifying the user that the fill has been stopped can be displayed.

After the cannula has been filled, if the site reminder function is not set to on, the system then reverts to a completed load menu. If the site reminder function is on, the system will proceed to a site reminder sequence described below. As with previous sequences, a number of additional safety and/or error checks can occur throughout the fill cannula sequence 700 that can cause the system to exit the sequence, with corresponding error screens such as those depicted in FIG. 19B.

Figure 20A:
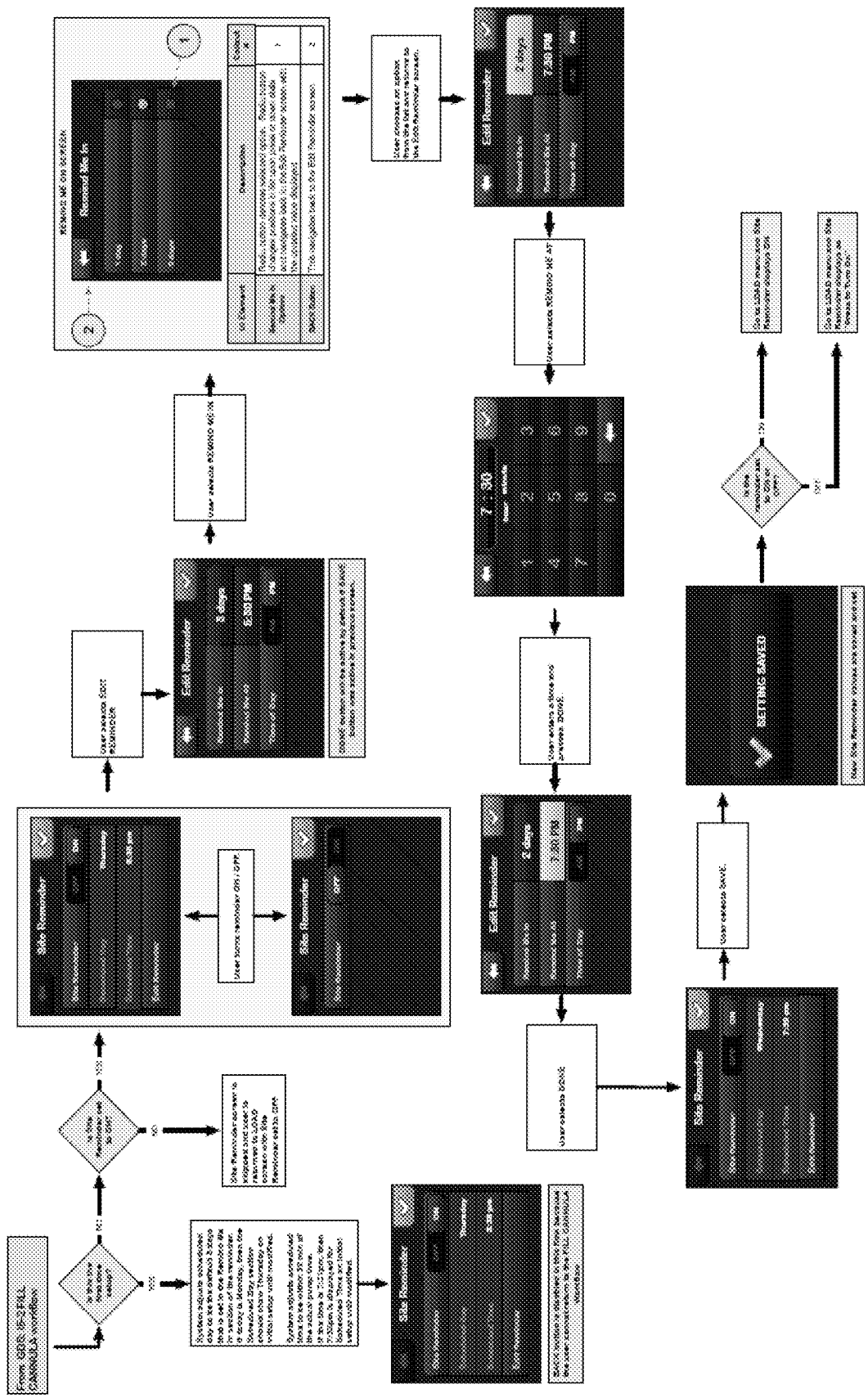
FIGS. 20A-20C depict a procedure for executing a site reminder function of an infusion pump system and corresponding menu screens according to the disclosure.
Figure 20B:
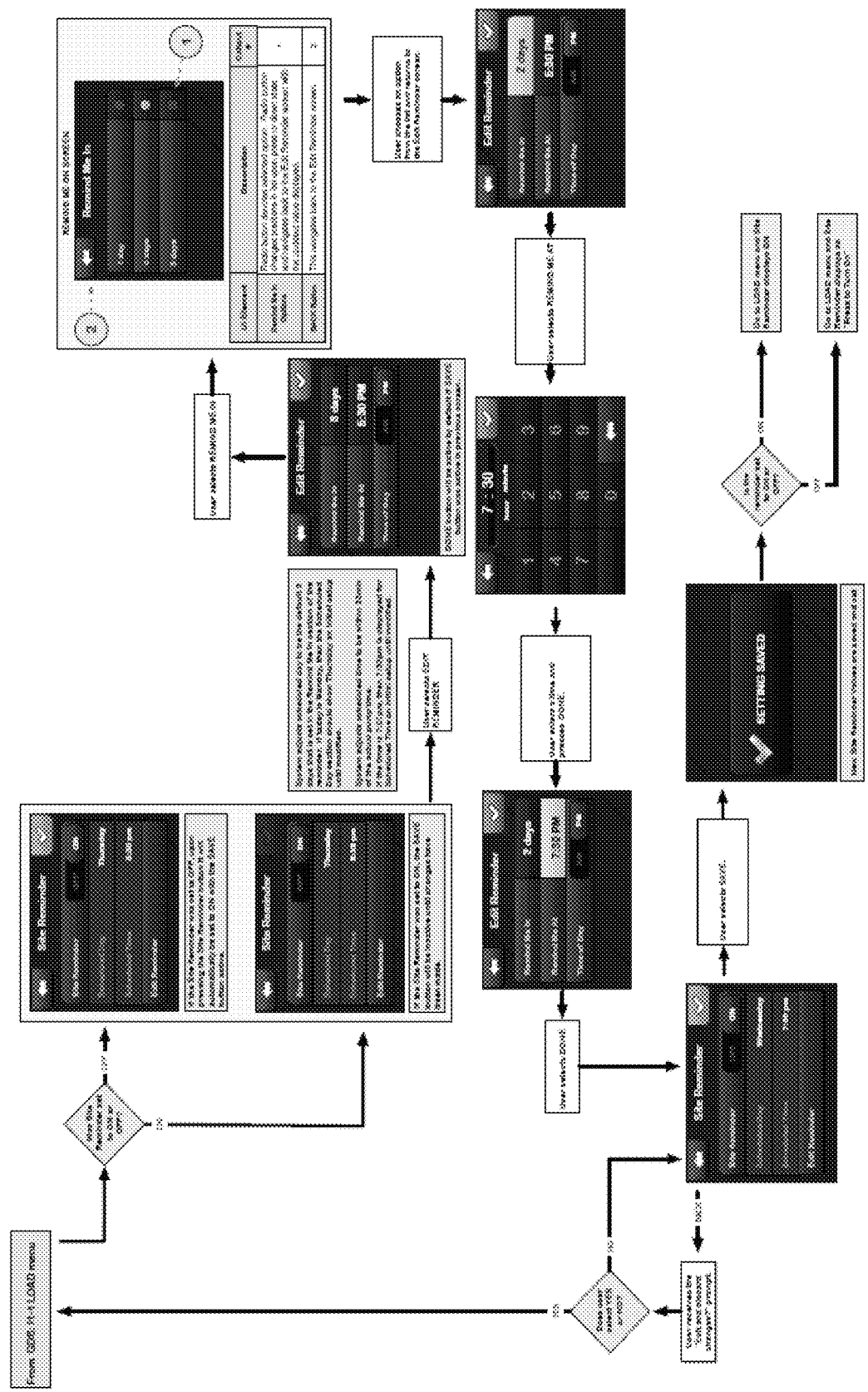
Figure 20C:
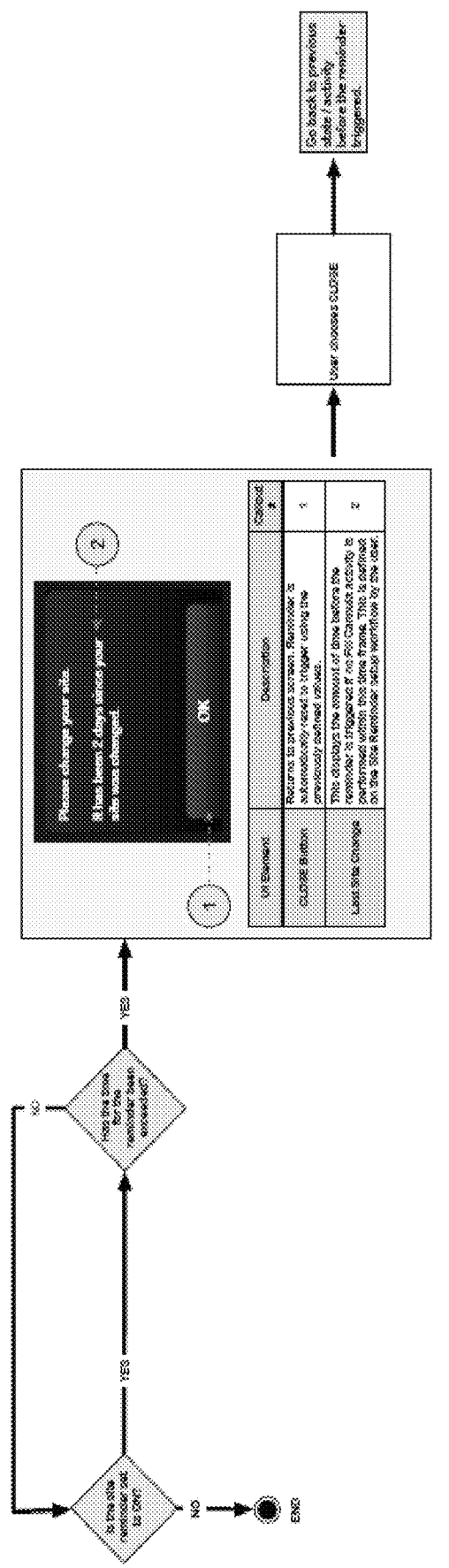

In some embodiments, the site reminder feature noted above and further discussed with respect to the alarm screen depicted in FIG. 12B can be accessed in two different ways. One way for the feature to be accessed is directly after the user completes the fill cannula procedure described in FIGS. 19A-19B. FIG. 20A depicts a procedure for activating the site reminder function from the fill cannula procedure according to an embodiment. The feature can also be accessed be selecting the site reminder item in the load menu (see, e.g., FIG. 16B). FIG. 20B depicts a procedure for activating the site reminder function from the Load menu according to an embodiment. FIG. 20C depicts a site reminder alert that can be displayed on the remote control when the user has programmed and turned on a site reminder.

Volume Settings

Figure 21:
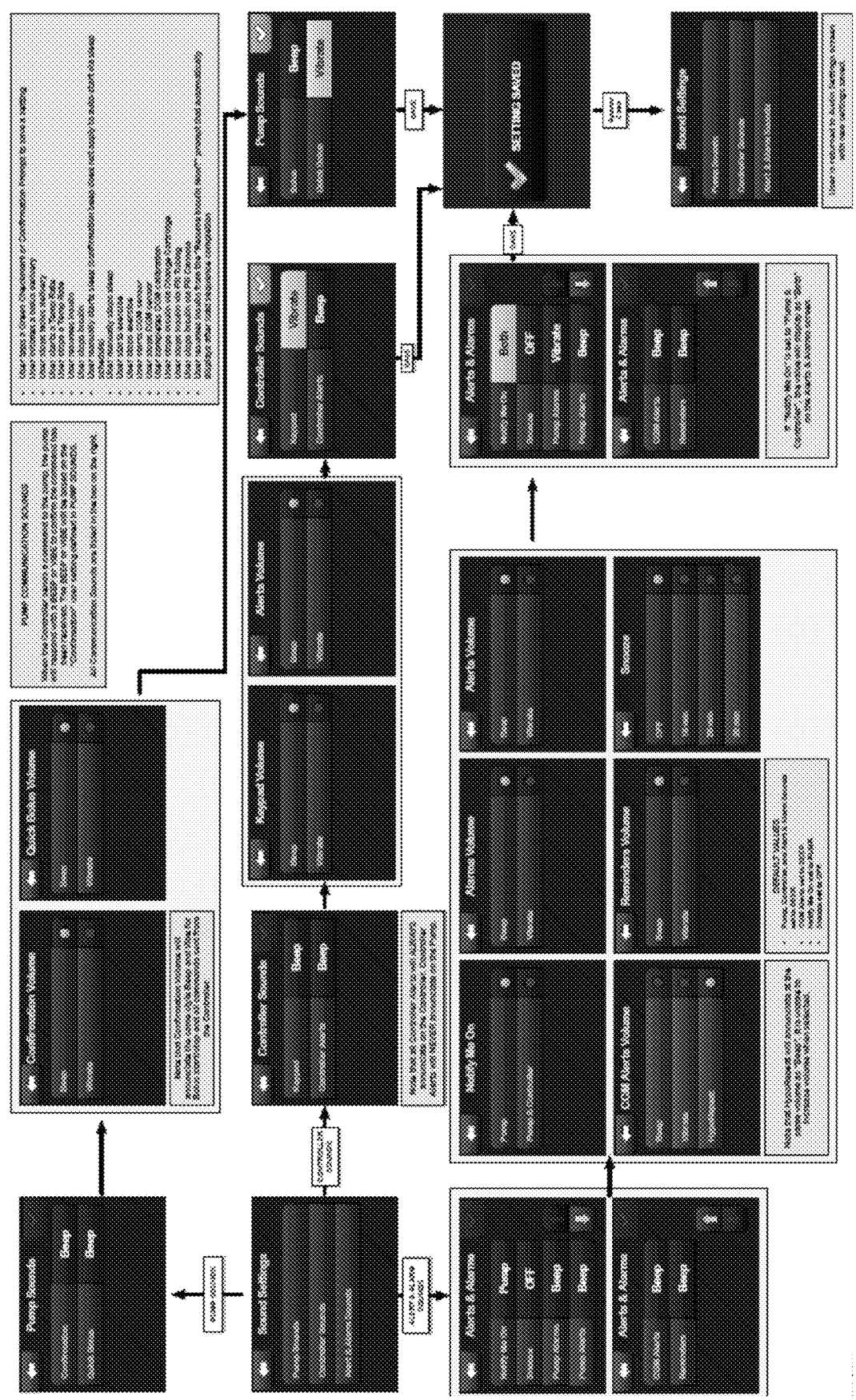
FIG. 21 depicts various display screens for programming these volume controls according to an embodiment.

Due to the lack of a display on pump 102, the remote control device 170, 171 used to control the pump can also be used to set various volume controls for the pump. Different volume levels can be set for different annunciations including pump alarms, alerts and reminders, CGM alerts, bolus deliveries, quick bolus programming, fill tubing procedures as well as audible beeps corresponding to button presses on the pump. FIG. 21 depicts various display screens for programming these volumes according to an embodiment. Once programmed on the remote control, a command can be sent from the remote controller to the pump instructing the pump to issue sounds at the corresponding levels.

Connection Issues

Figure 22A:
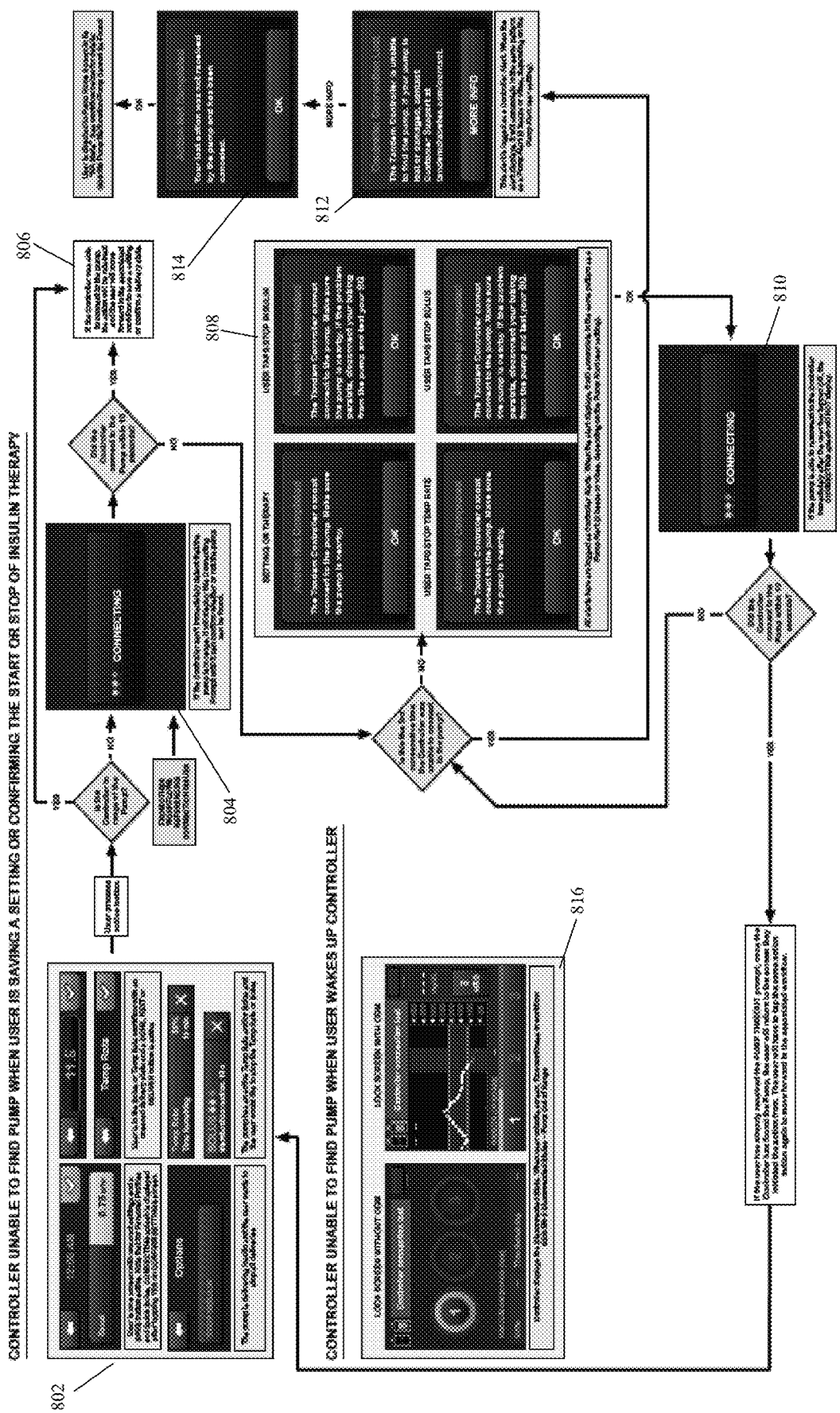
FIGS. 22A-22C depict various screens that can be displayed on a remote control device for an infusion pump system according to the disclosure.
Figure 22B:
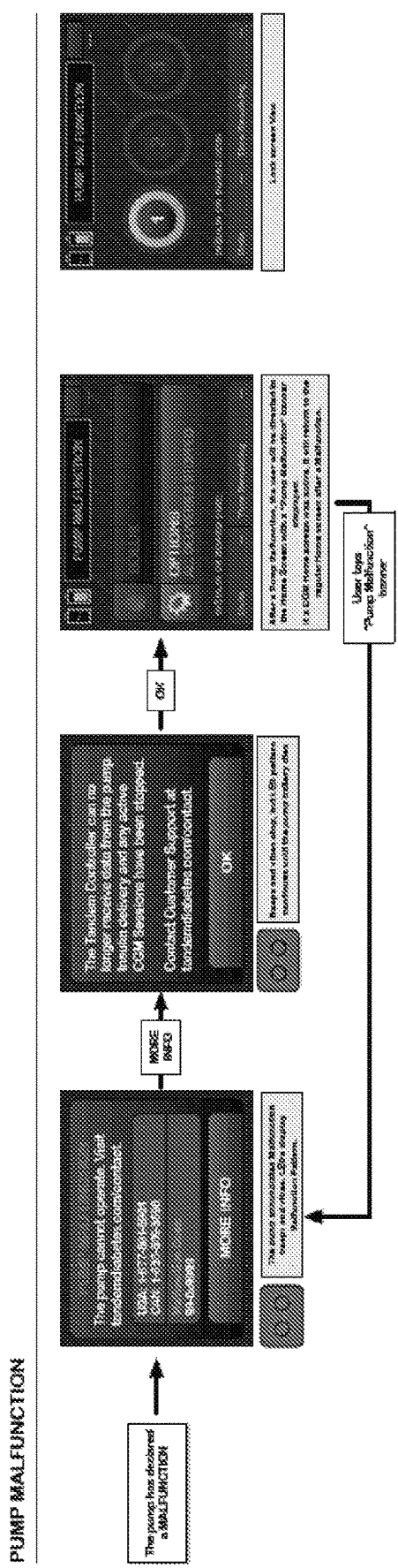
Figure 22C:
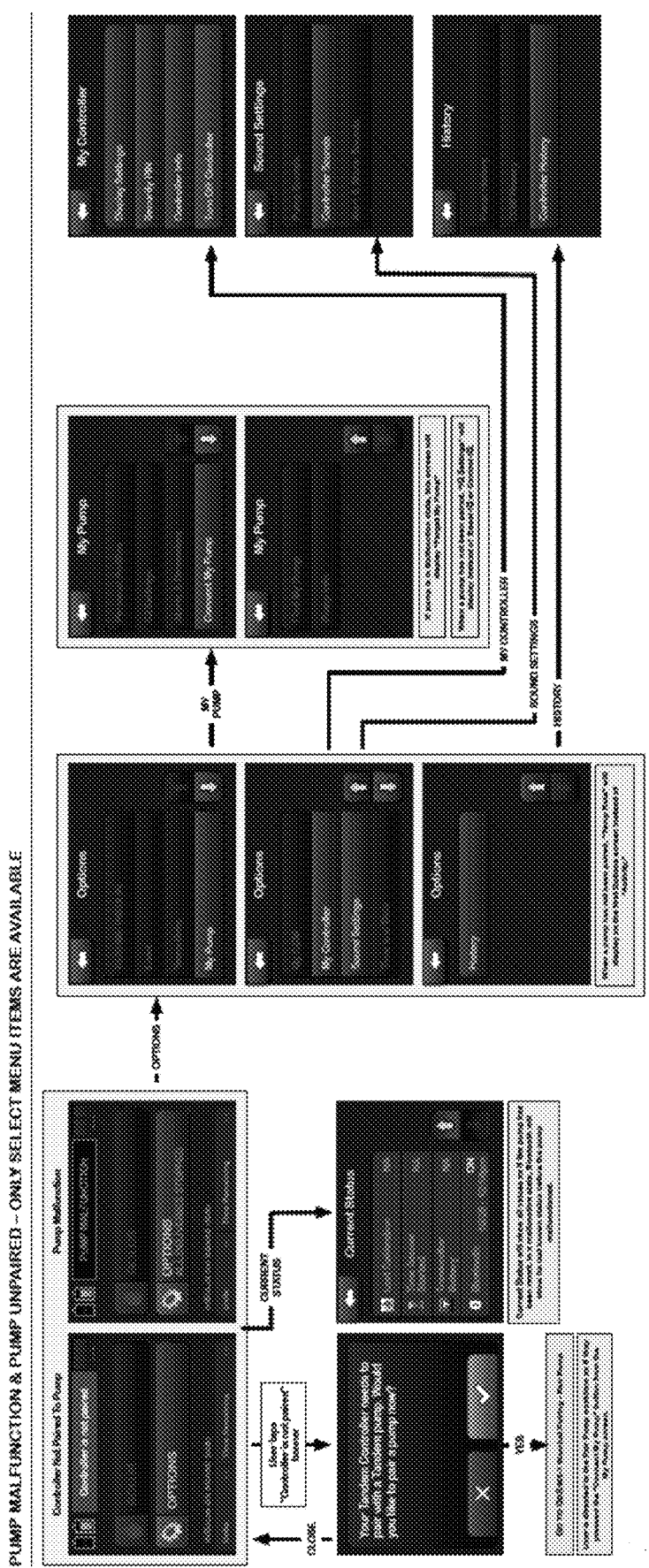

As discussed above, programming and operation of user-wearable pump with remote control device requires a paired connection between the pump and the remote control. However, during device operation the remote control device may move out of range of the pump or otherwise become disconnected from and/or unable to communicate with the pump. FIGS. 22A-22C depict various remote control device screens and operations that can be carried out when connection issues are preventing communications between the remote control device and the pump.

Referring to FIG. 22A, at step 802 the remote controller may be unable to locate the pump when the user is confirming any number of settings, such as, for example, starting insulin delivery, stopping insulin delivery, etc. If that occurs, a "Connecting" screen can be displayed at step 804 while the remote controller attempts to locate the pump. If the controller is able to locate the pump, at step 806 the setting can be saved and operations can continue as normal. If the controller is not able to locate the pump, an Action Not Completed error message can be displayed at step 808. After the user clears the error message, the controller may again at step 810 attempt to connect to the pump. After a predetermined number of attempts to connect to the pump, such as, for example, 3 attempts, if the controller does not connect to the pump a Controller Connection Lost screen can be displayed at step 812 notifying the user that the controller cannot locate the pump. The user can then be provided with a further Action Not Completed screen at step 814 indicating that the attempted action was not completed. The remote controller may also be unable to locate the pump when the controller is awoken from a sleep state. The controller may then display a notification on the home screen that connection has been lost at step 816.

FIG. 22B depicts a series of display screens that can be displayed on the remote control device when a pump malfunction has been determined because the controller connection is lost. The Pump Malfunction screen can notify the user that the pump cannot operate and provide information for seeking support, such as a website, phone number, etc. The indicator lights on the pump may also annunciate a malfunction as described above. If the user selects the More Info tab, an additional information screen can inform the user that insulin delivery has been stopped because the controller can no longer receive data from the pump. In this embodiment, the malfunction light pattern remains on. When the user returns to the home screen and/or lock screen a Pump Malfunction banner can be displayed. In some embodiments, the user can select the Pump Malfunction banner to return to the Pump Malfunction information screens.

A series of menu screens that can be displayed when there is a pump malfunction due to connection issues with the remote control and when the controller is not paired with the pump are depicted in FIG. 22C. In such circumstances, only limited menu items are available such the user is not able to select certain menu items that would be available during normal operations. For example, while the user may select the Options item from the home screen, the Bolus item for programming a bolus delivery is unavailable. If the remote control has not been paired with the pump, but a malfunction has not been determined, a banner indicating Controller is not paired can be displayed. If the user selects the Controller is not paired banner, the user can be directed to a screen enabling the issue to initiate a pairing procedure to pair the remote control with the pump. Further detail regarding such a pairing procedure can be found in U.S. patent application Ser. No. 16/507,146, which is hereby incorporated by reference herein in its entirety. If the user selects the Options item from the home screen the user will be able to navigate the menu hierarchy of the remote controller, but certain items will not be selectable due to the disconnection between the pump and the controller. Disabled menu items can include, for example, those relating to medicament delivery, pump data and CGM data.

Figure 23A:
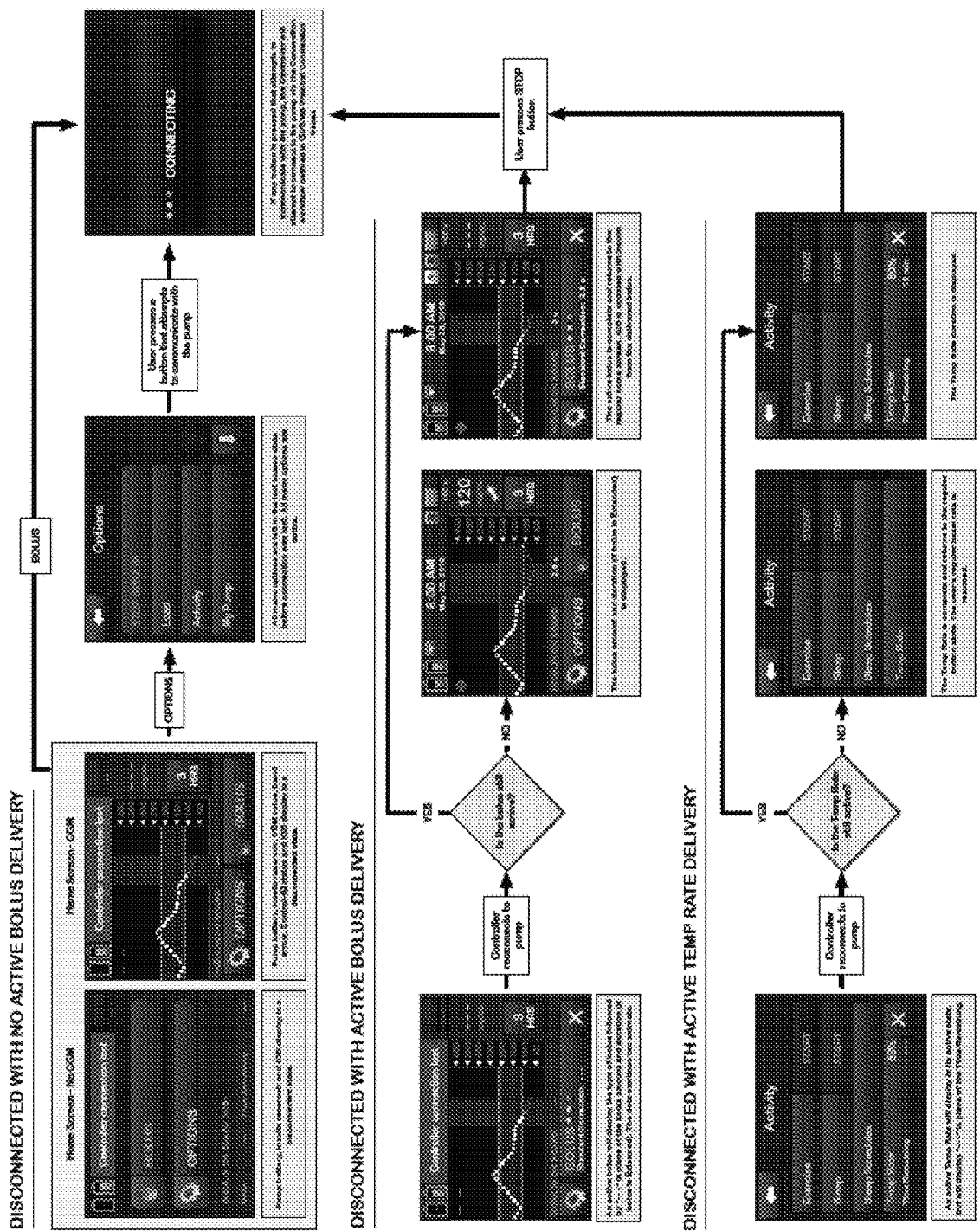
FIGS. 23A-23B depict various screens that can be displayed on a remote control device for an infusion pump system according to the disclosure.

FIG. 23A depicts displays screens that the remote control device can display when the controller has become disconnected from the pump without an active bolus delivery, with an active bolus delivery, and with an active temporary basal rate being delivered. The home screen can display the Controller connection lost banner and display icons and menu items relating to the pump and CGM in a disconnected state, such as the pump battery indicator, medicament reservoir indicator, insulin on board, CGM value and CGM trend arrow. If the user selects the Options items all options can be displayed, but if the user selects an option that requires communication with the pump, rather than executing the option the controller will display the Connecting screen and attempt to connect with the pump. Similarly, if the user selects the active Bolus item on the home screen, the controller will attempt to connect with the pump. If the controller is unable to connect with the pump, it will follow the connection procedure discussed above.

Figure 23B:
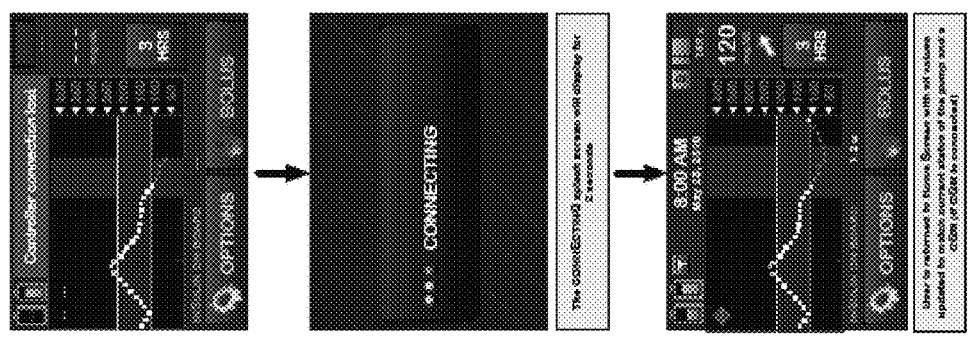

If a bolus was active when the controller connection was lost, the home screen will display the type of bolus followed by "---" in place of the bolus amount and duration (for an extended bolus) that would be displayed during normal operation. If the controller subsequently reconnects with the pump, it determines if the bolus is still being actively delivered by the pump. If the bolus is still ongoing, the amount of the bolus (and duration if needed) is again displayed. If the bolus has completed, no indication of the bolus is displayed, but the insulin on board is updated with the insulin delivered in the bolus. If a temporary basal rate was active when the connection was lost, the temporary rate will similarly display "---" in place of the time remaining that would be displayed during normal operation. When the connection is reestablished, the time remaining will again be displayed if the temporary rate is still active. If not, the regular basal rate is resumed and no indication of a temporary rate is displayed. Referring to FIG. 23B, if the pump comes back into range with the controller when the screen is on, the remote control will display the Connecting screen and then return the home screen to its normal state.

Figure 24:
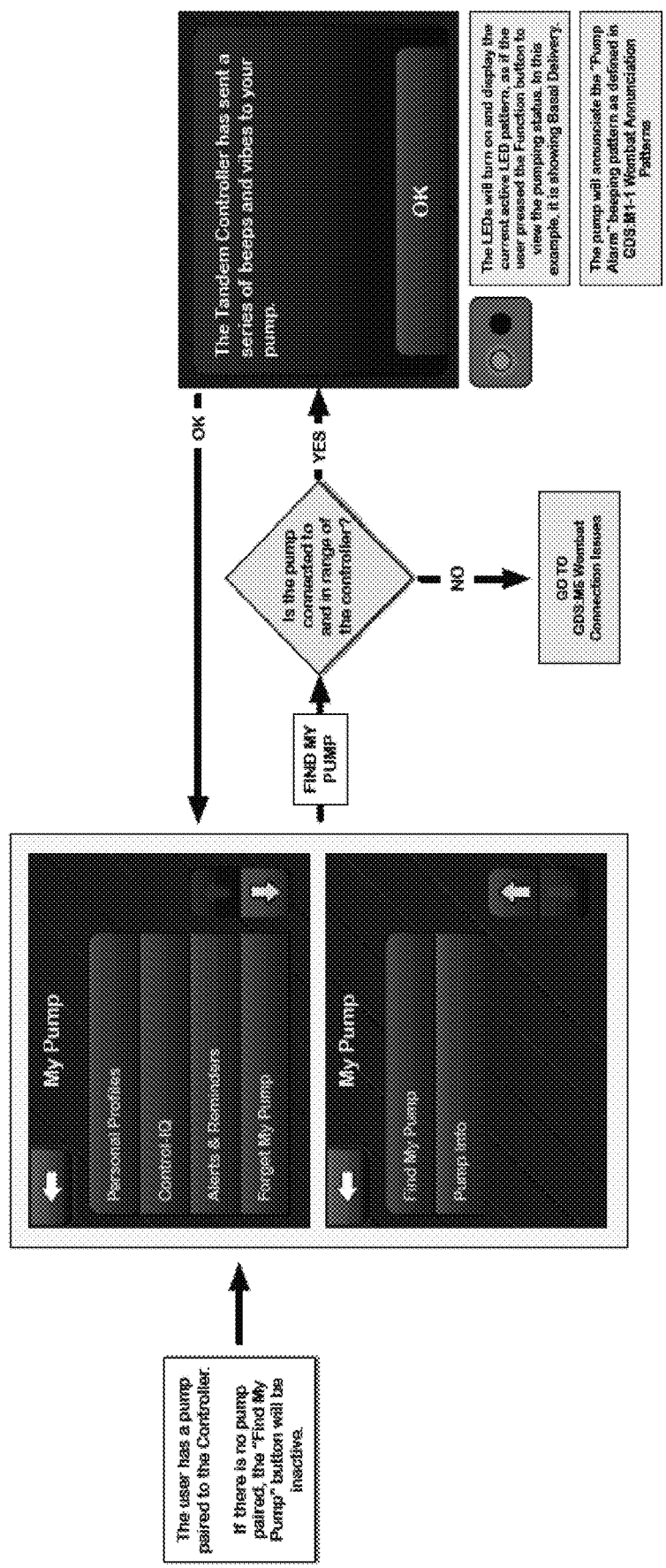
FIG. 24 depicts various screens that can be displayed on a remote control device for an infusion pump system according to the disclosure.

FIG. 24 displays a Find My Pump feature that can be executed with a remote controller. The feature can be selectable from the My Pump menu that can be accessed with the Options item on the home screen. If no pump is paired to the controller, the feature will not be selectable. If the user selects the Find My Pump feature, the controller determines if the pump is in range and if not executes the connection issues workflows described above. If the pump is in range, the controller will send a series of beeps and/or vibrations to the pump to enable the user to locate the pump. The indicator lights on the pump may also activate to indicate the current pump status and/or to annunciate a pump alarm as described above.

Figure 25A:
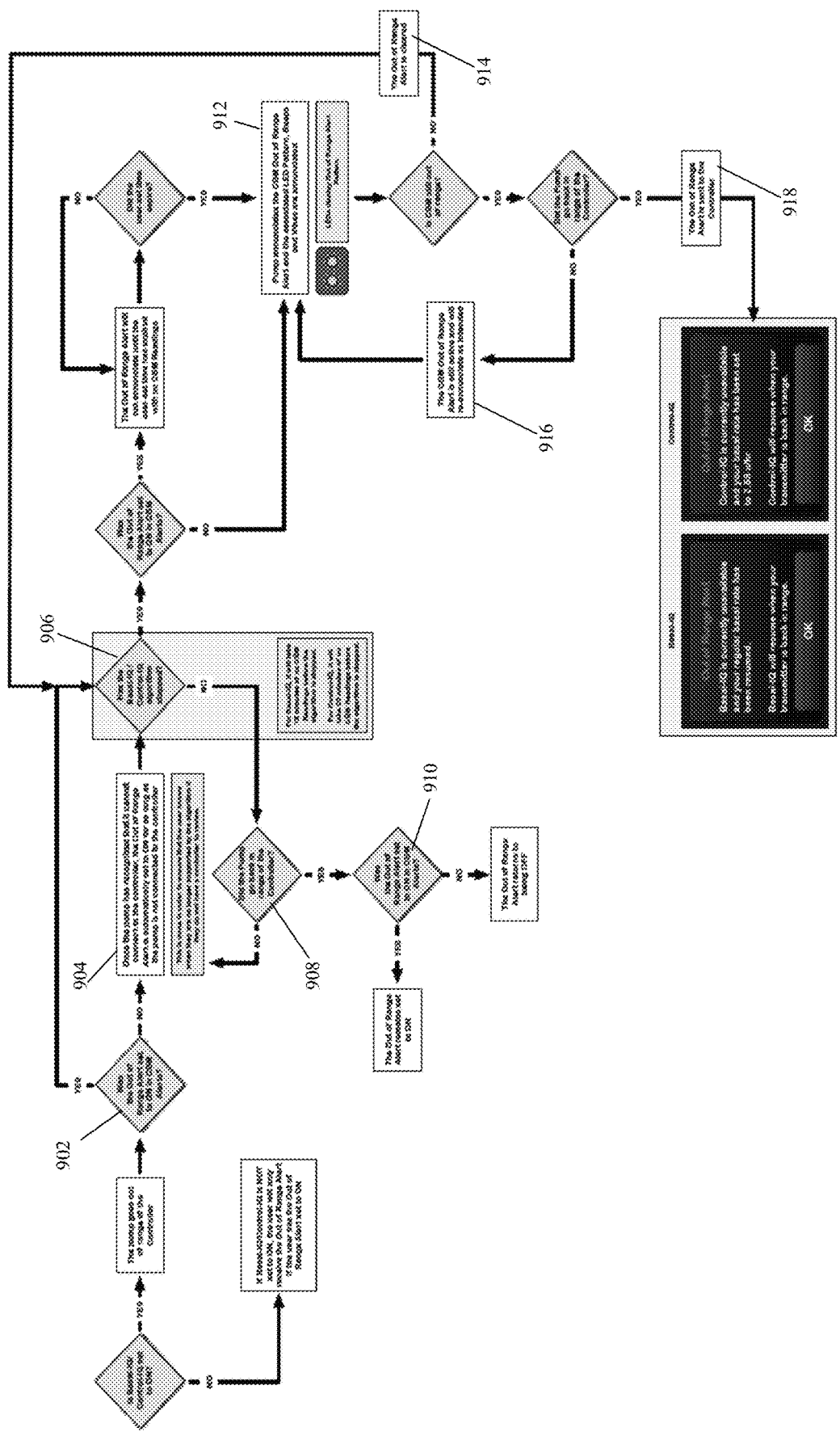
FIGS. 25A-25B depict procedures for when a pump goes out of range of a remote control according to an embodiment of the disclosure.
Figure 25B:
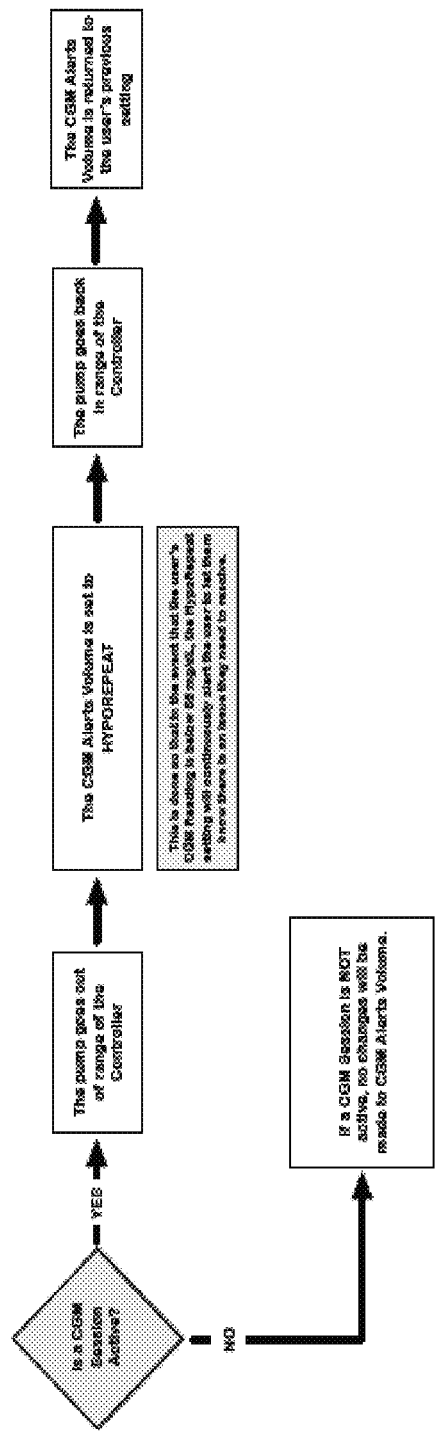

FIG. 25A depicts a procedure for operating the pump when the pump goes out of range of the remote control when the remote control is operating an algorithm that utilizes CGM data to automatically determine therapy parameters for the user. If the pump goes out of range of the remote control device when such an algorithm is turned on, at step 902 it is determined if the Out of Range Alert was set to on in CGM Alerts on the controller. If not, the Out of Range Alert is automatically set to on at step 904. The system then determines if the algorithm has stopped executing at step 906. This may occur because the algorithm may stop operating if no CGM data is received for a predetermined period of time. If the algorithm has not stopped, the system continues to check if the pump has come back into range of the controller at step 908. If the pump does come back into range, the Out of Range Alert can be returned to its previous state and no alert is given. If the algorithm stops operating and the pump does not come back into range of the controller, the system determines at step 910 if the Out of Range Alert was initially on. If the alert was off, the pump annunciates the CGM Out of Range Alert with the associated light, sound and/or vibration pattern at step 912. If the Out of Range Alert was on, the pump waits to execute the alert at step 912 until the user-set time for the alert expires. Following the alert, the controller will check if the CGM is still out of range and if the pump is still out of range. If the CGM is back in range, the Out of Range Alert is cleared at step 914. If the CGM and the pump are both still out of range, the CGM Out of Range will re-annunciate at step 916. If the pump is back in range of the controller but there is still no CGM data, the controller will display an Out of Range alert at step 918 informing the user that the algorithm is unavailable and will resume from a default basal level when the CGM transmitter is back in range. FIG. 25B depicts a Hyporepeat feature that sets the CGM Alerts volume to a Hyporepeat level (See FIG. 21) that continuously alerts the user. This feature is activated if the pump goes out of the range of the controller when the user's last CGM reading was below a predetermined low threshold, such as, for example, 55 mg/dL.

Power Features

Both the remote control device and the pump require a power supply to maintain continuous operation. In embodiments, the power supply can be one or more rechargeable and/or replaceable batteries. The system can therefore include various features that monitor and/or inform a user regarding the system power supplies.

Figure 26A:
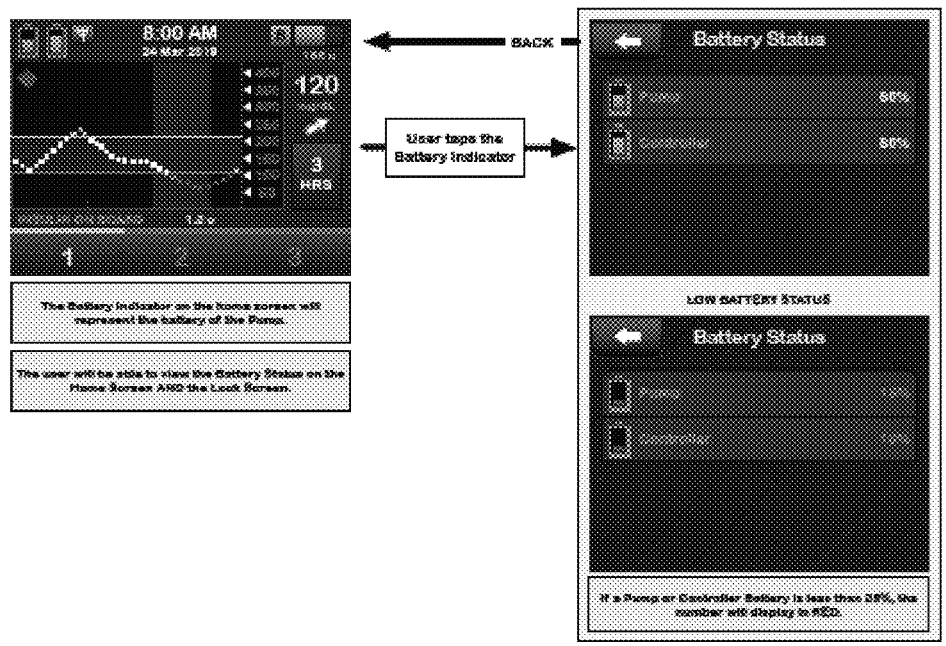
FIGS. 26A-26E depict various screens that can be displayed on a remote control device for an infusion pump system relating to battery power according to the disclosure.
Figure 26B:
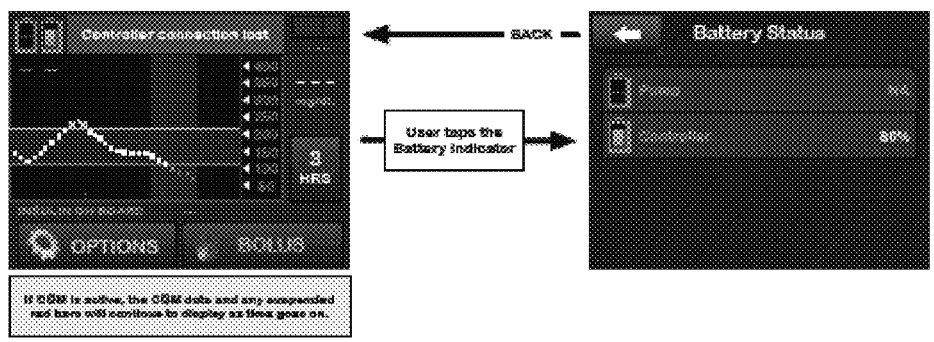
Figure 26C:
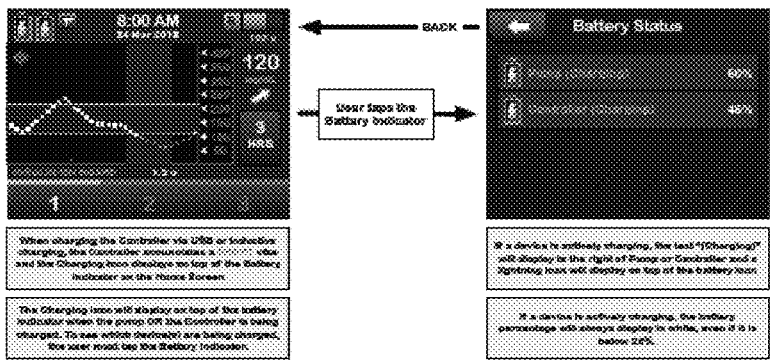
Figure 26D:
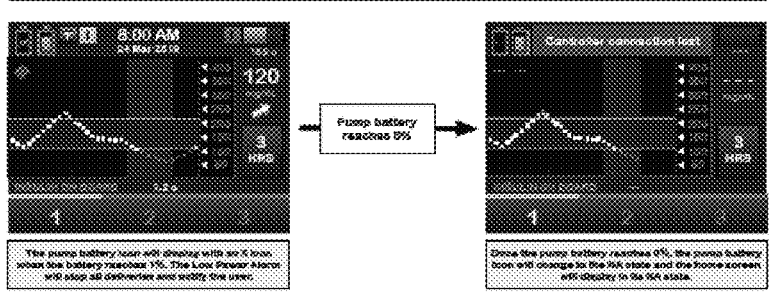
Figure 26E:
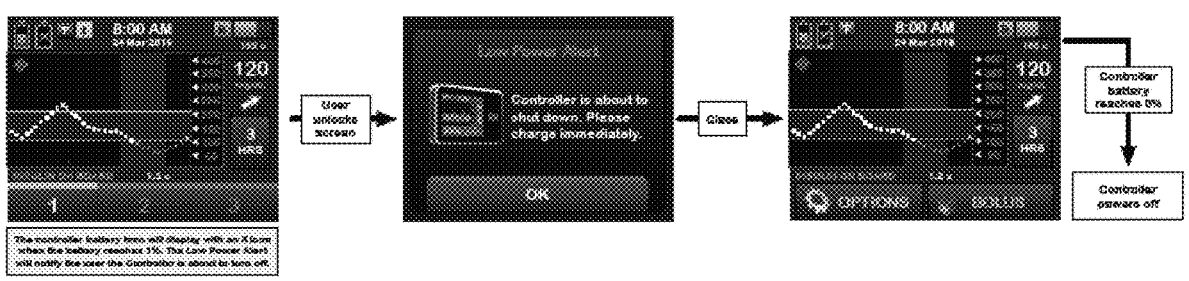

FIGS. 26A-26E depict various display screens relating to battery power that can be accessed on the remote control device. Referring to FIG. 26A, if the user selects the Battery Indicators in the upper left of the home screen, the user will be taken to a Battery Status screen that shows the battery level of both the pump and the controller. If the pump is not connected to the controller, the pump level will be empty and only the actual battery level of the controller is displayed as depicted in FIG. 26B. If the pump and/or controller are actively charging, a charging indicator (e.g., a lightning bolt) can be displayed over the battery level icon on both the home and lock screens and in the Battery Status screen as depicted in FIG. 26C. Referring to FIG. 26D, when the pump battery is down to 1%, a low power icon (e.g., an "X") can be displayed on the pump battery indicator on the home and lock screens. Once the pump battery reaches 0% the battery icon will change to the blank (" . . . ") state and a banner indicating Controller connection lost will be displayed. Similarly, as shown in FIG. 26E, when the controller battery reaches 1% an icon such an "X" can be displayed on the controller battery indicator on the lock screen. If the user unlocks the screen a Low Power Alert instructing the user to charge the controller immediately can be displayed.

Figure 27A:
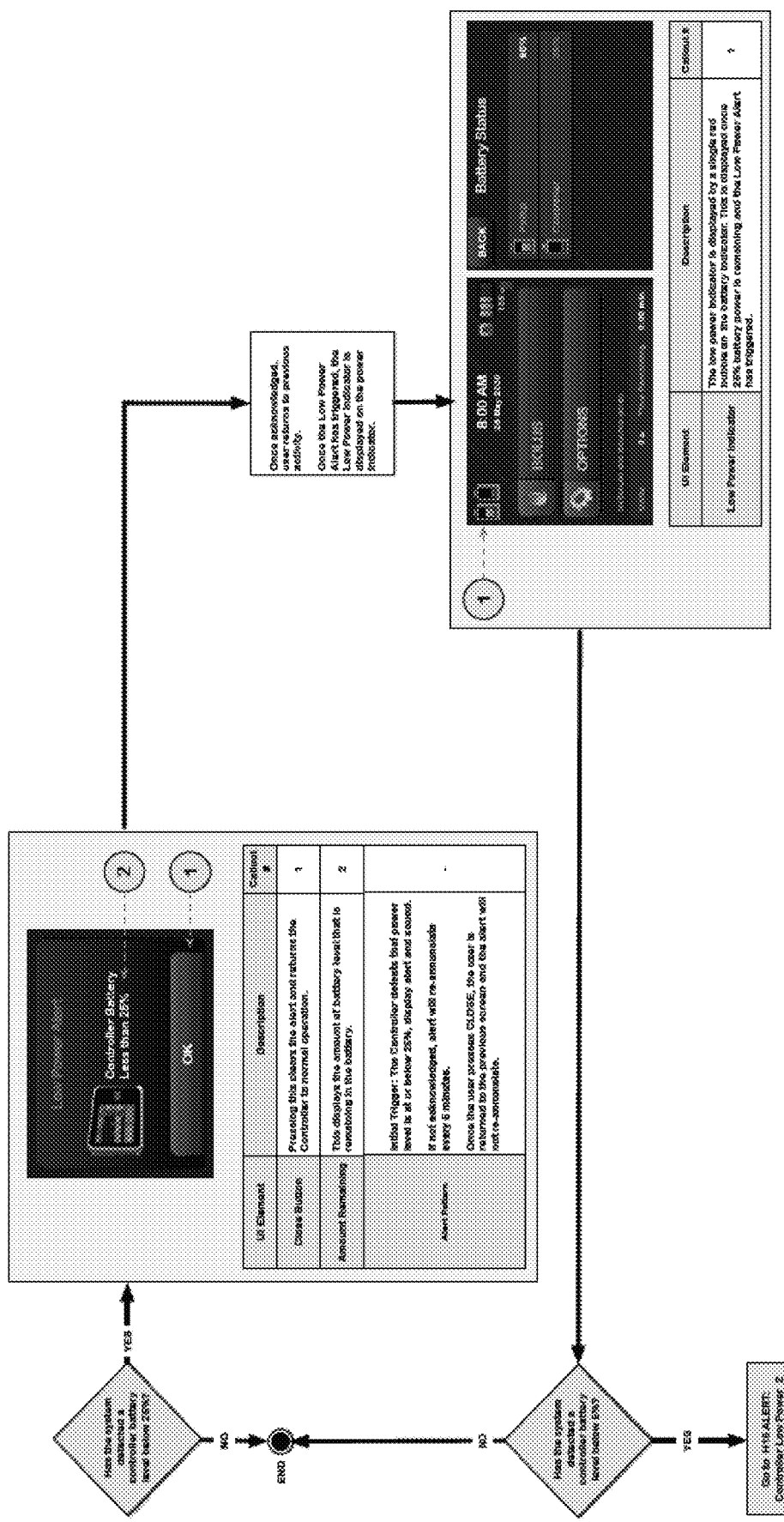
FIGS. 27A-27D depict a workflow and various screens that can be displayed on a remote control device for an infusion pump system relating to controller batter power according to the disclosure.
Figure 27B:
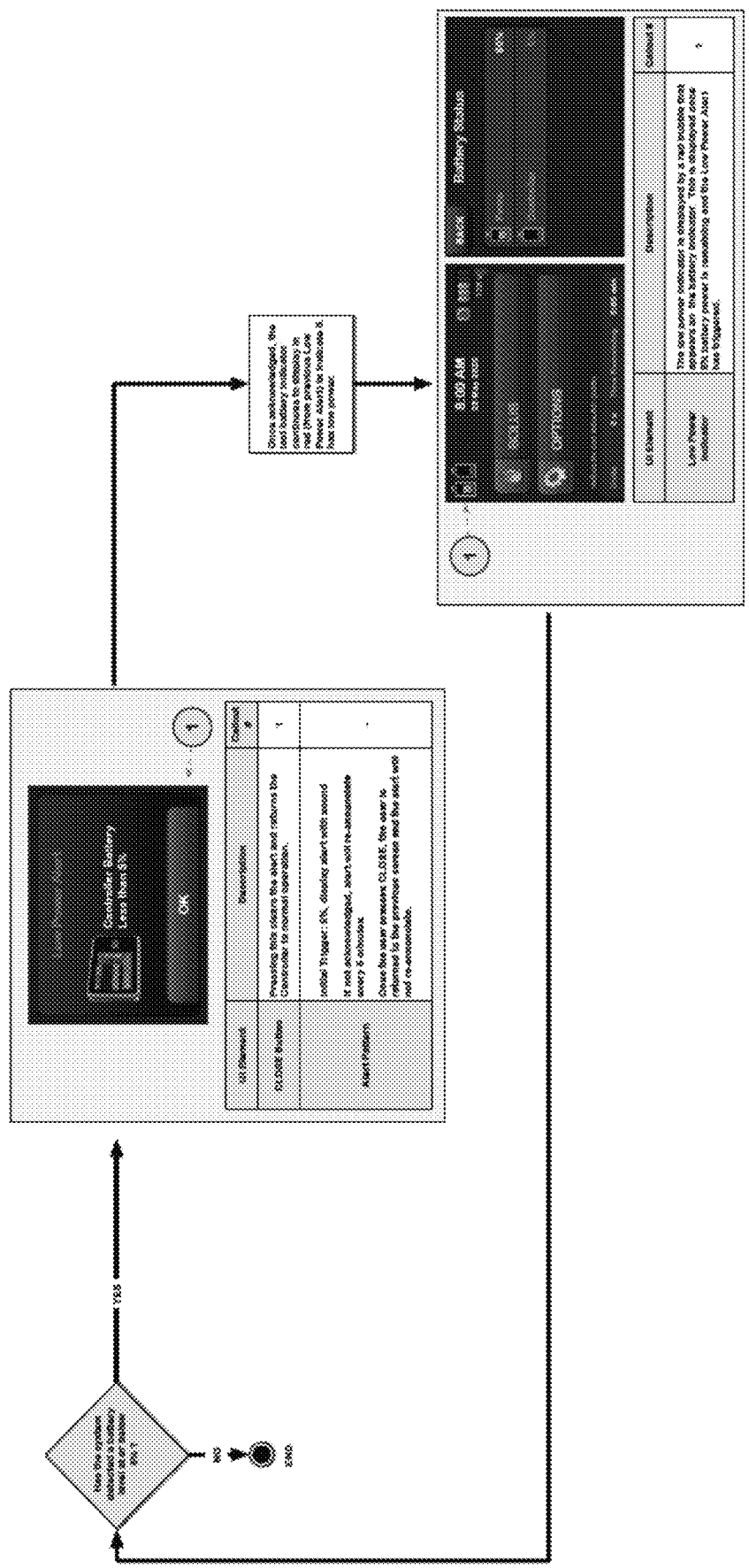
Figure 27C:
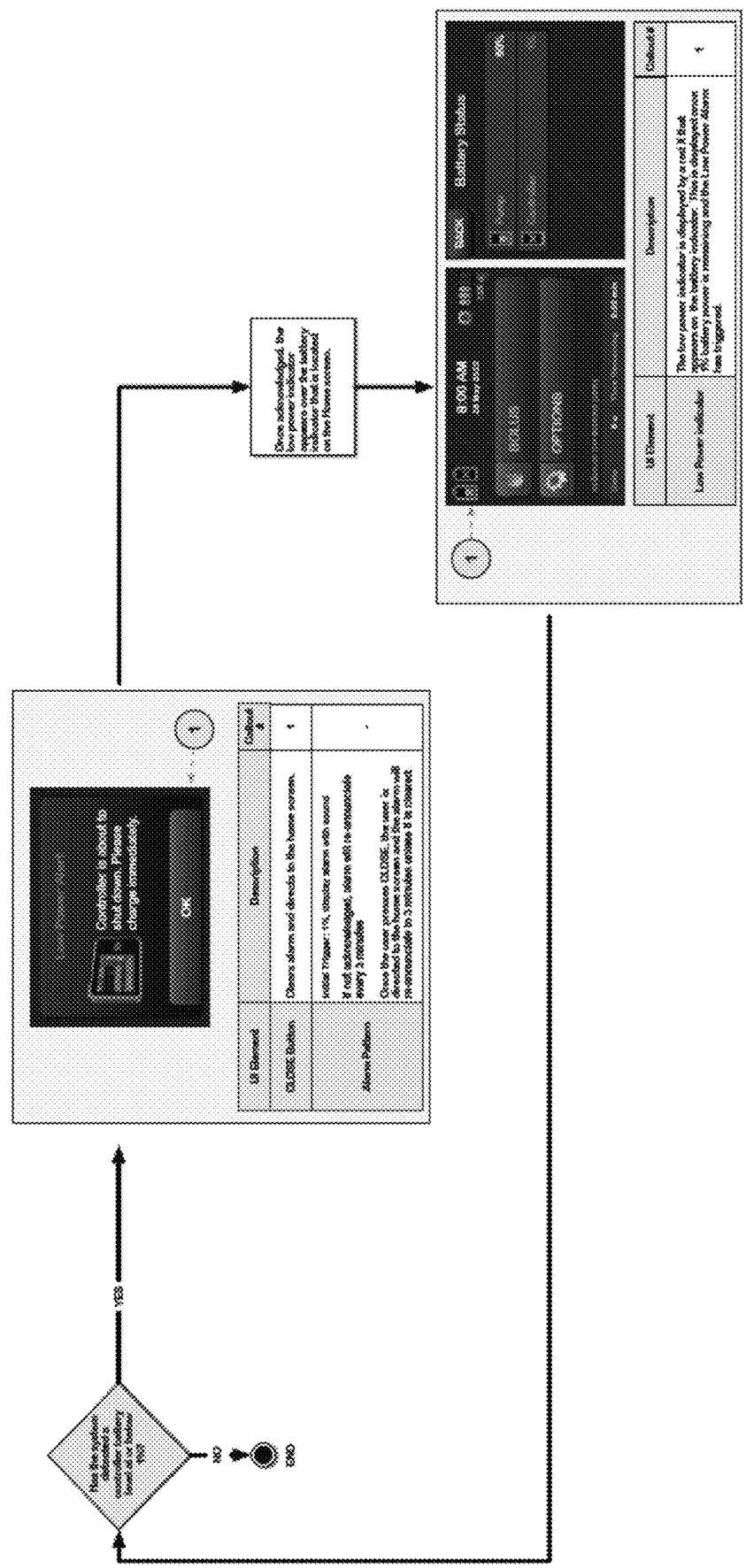
Figure 27D:
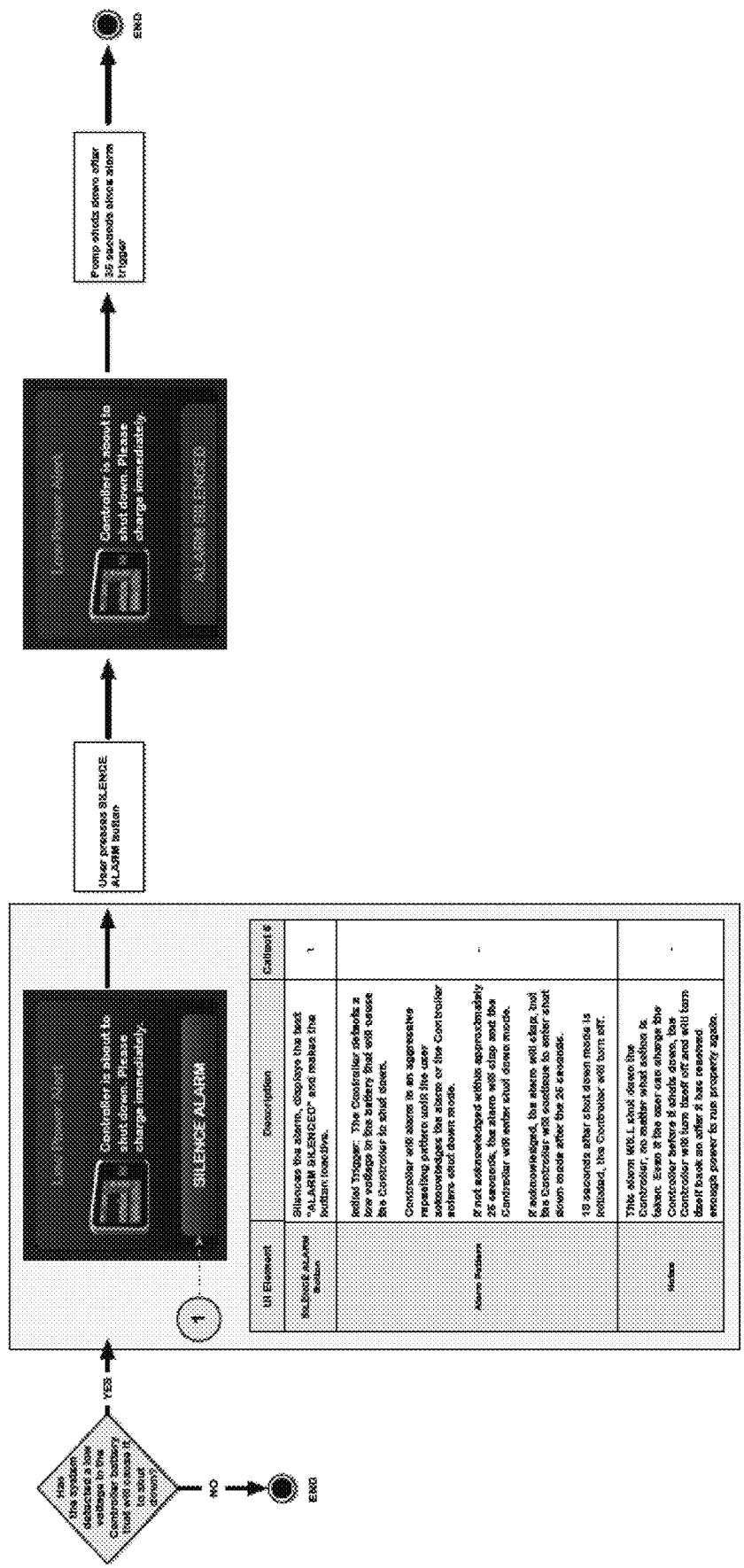

A number of different alerts can be provided to indicate to a user that the battery power of the remote control device is low. For example, alerts can be provided at different power levels. FIG. 27A depicts an initial Low Power alert workflow that can be provided at a first low power threshold, such as, for example, at 25% battery power. The user can close the alert to return to normal operation with a lower power indicator displayed. Otherwise, the alert can re-annunciate periodically until the alert is closed. If the battery falls below a second, lower threshold, such as, for example, 5%, a second Low Power Alert such as depicted in FIG. 27B can be displayed. This alert can be closed and generally functions the same as the previous alert, with the exception of the low power amount being indicated. A third low power alert as depicted in FIG. 27C can be issued if the controller battery is at or below 1%. This alert indicates that the controller is about to shut down and that charging is needed immediately. The alert may continue to re-annunciate periodically until the controller is charged. Referring to FIG. 27D, if the system detects a low voltage in the battery that will cause the controller to shut down (e.g., close to 0%), the Low Power Alert will be displayed and a loud, repeating alarm sound will be issued. The alarm will then cause the controller to shut down.

Figure 28A:
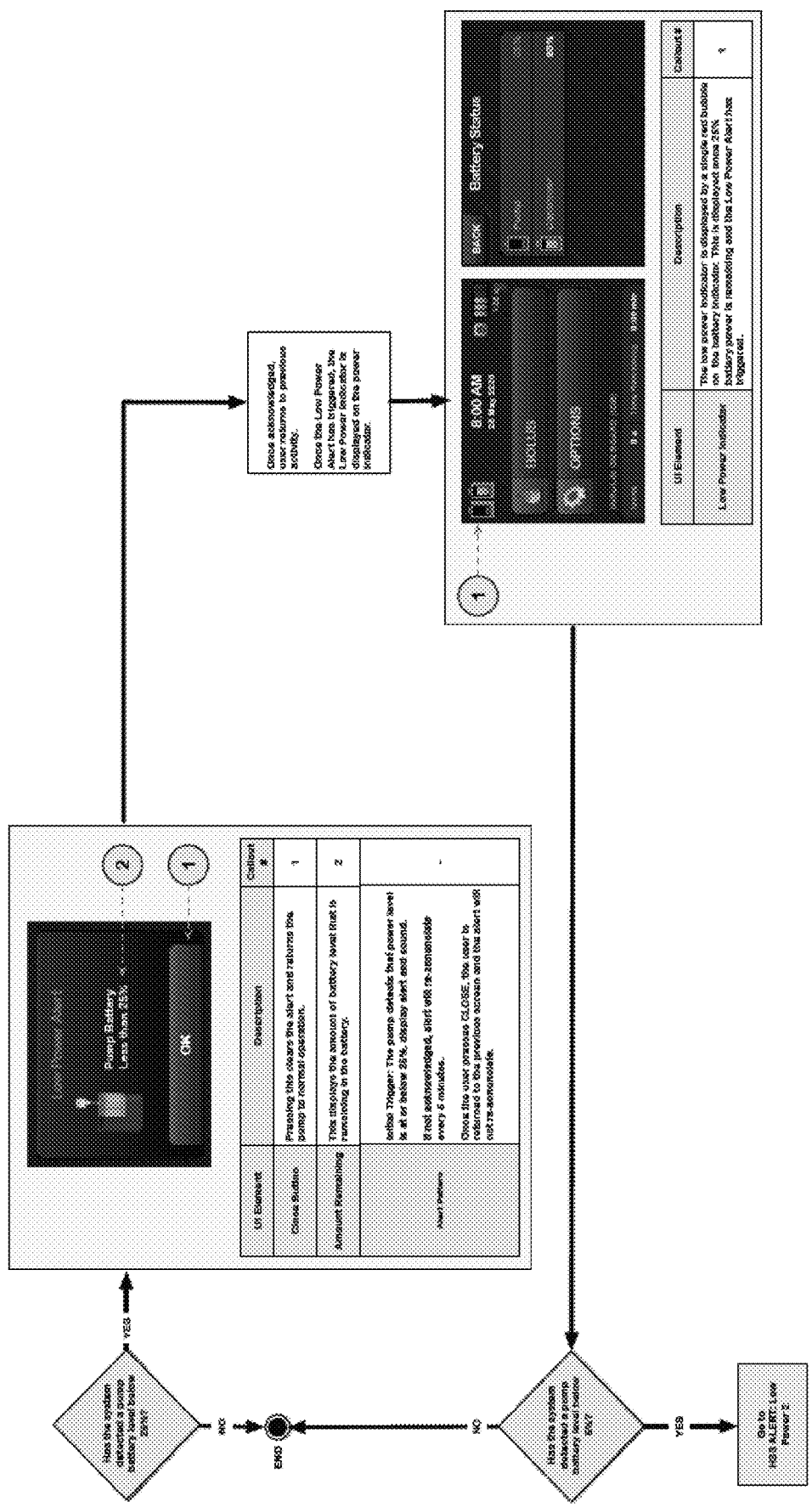
FIGS. 28A-28D depict a workflow and various screens that can be displayed on a remote control device for an infusion pump system relating to pump battery power according to the disclosure.
Figure 28B:
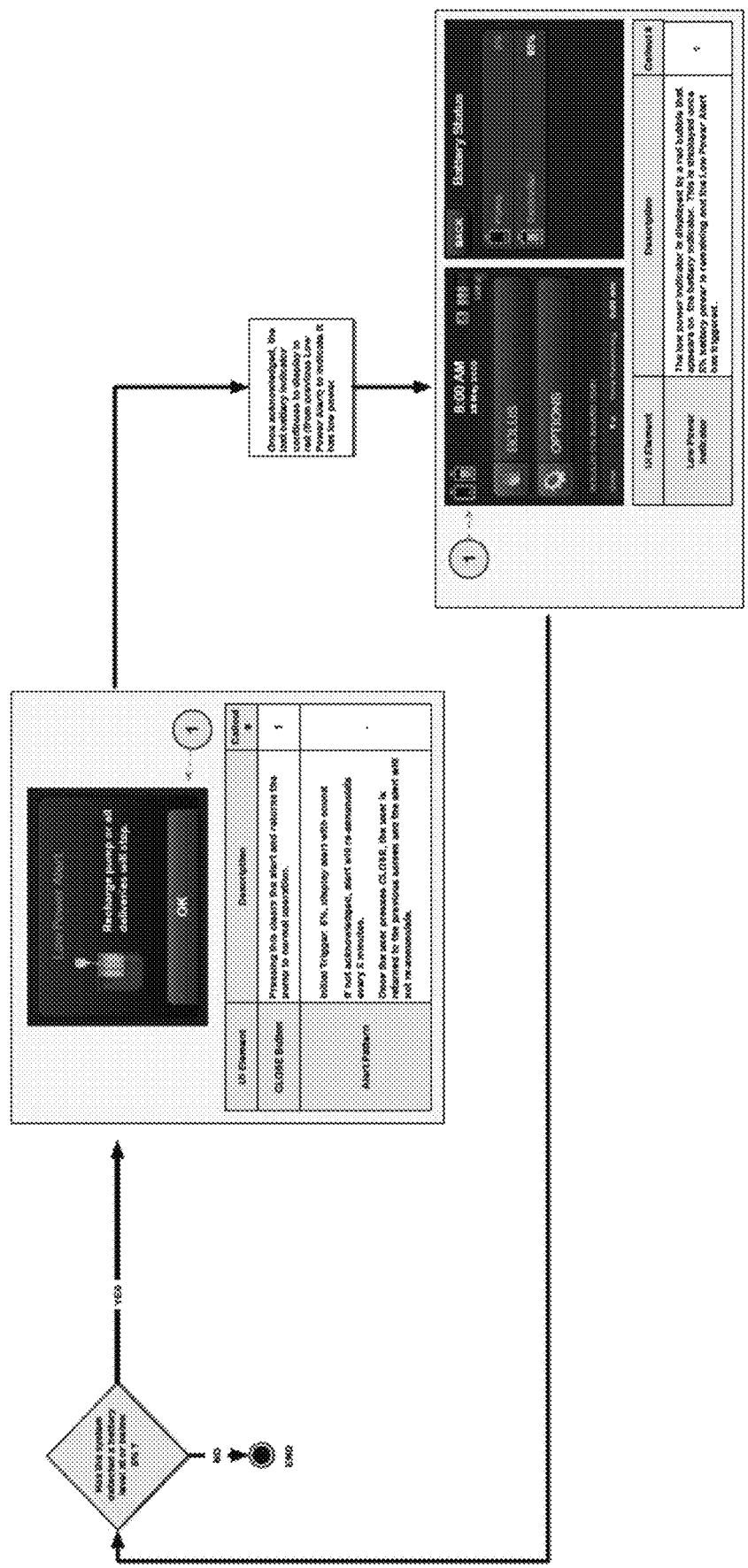
Figure 28C:
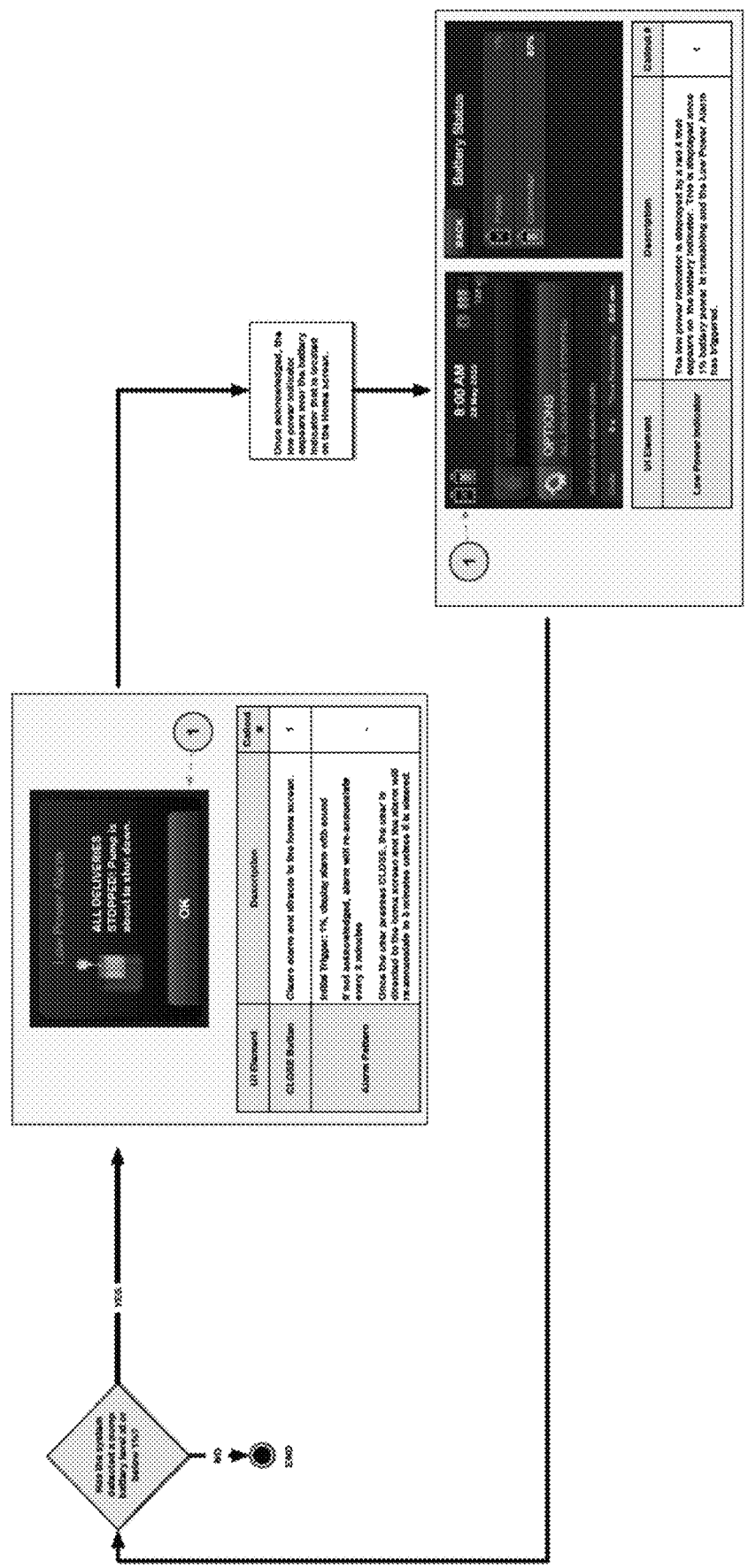
Figure 28D:
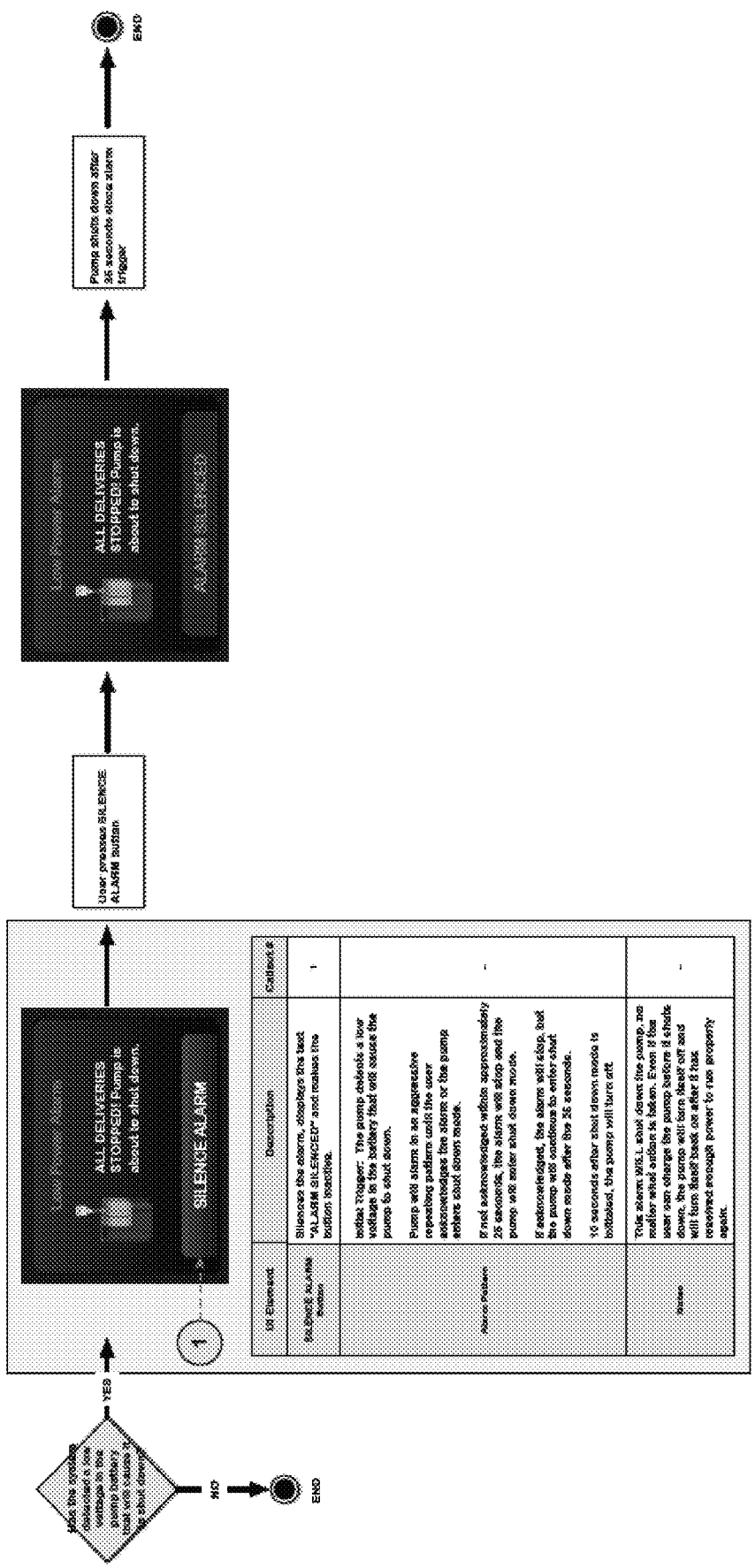

FIGS. 28A-28D depict workflows and corresponding display screens for notifying the user when the battery on the pump is low. FIG. 28A depicts a first Low Power Alert for the pump battery that can be issued when the pump battery reaches a first low threshold level, such as, for example, 25%. The user can acknowledge and close the alert by selecting the OK item, which will clear the alert and update the home and lock screens as well as the battery status screen to indicate the low battery status. Otherwise, the alert can be periodically re-annunciated after a predetermined period of time until the alert is acknowledged. When the pump battery reaches a second low battery level, such as, for example, 5%, a second Low Power Alert can be issued as depicted in the workflow of FIG. 28B. This alert can inform the user that the pump battery must be charged or all deliveries will stop. This alert can also be acknowledged and closed or will re-annunciate periodically. If the pump battery falls further, such as, for example to at or below 1%, the remote control can issue a Low Power Alarm as depicted in FIG. 28C indicating that all deliveries have been stopped and the pump is about to shut down. Even if the user closes the alarm to return to the home screen, the alarm will re-annunciate until the battery is charged. The home screen, lock screen and battery status screen will be updated to indicate that the pump battery is at or near dead. Referring to FIG. 28D, if the system detects a low voltage in the battery that will cause the pump to shut down (e.g., close to 0%), the Low Power Alert will be displayed and a loud, repeating alarm sound will be issued. The alarm will then cause the pump to shut down.

Figure 29:
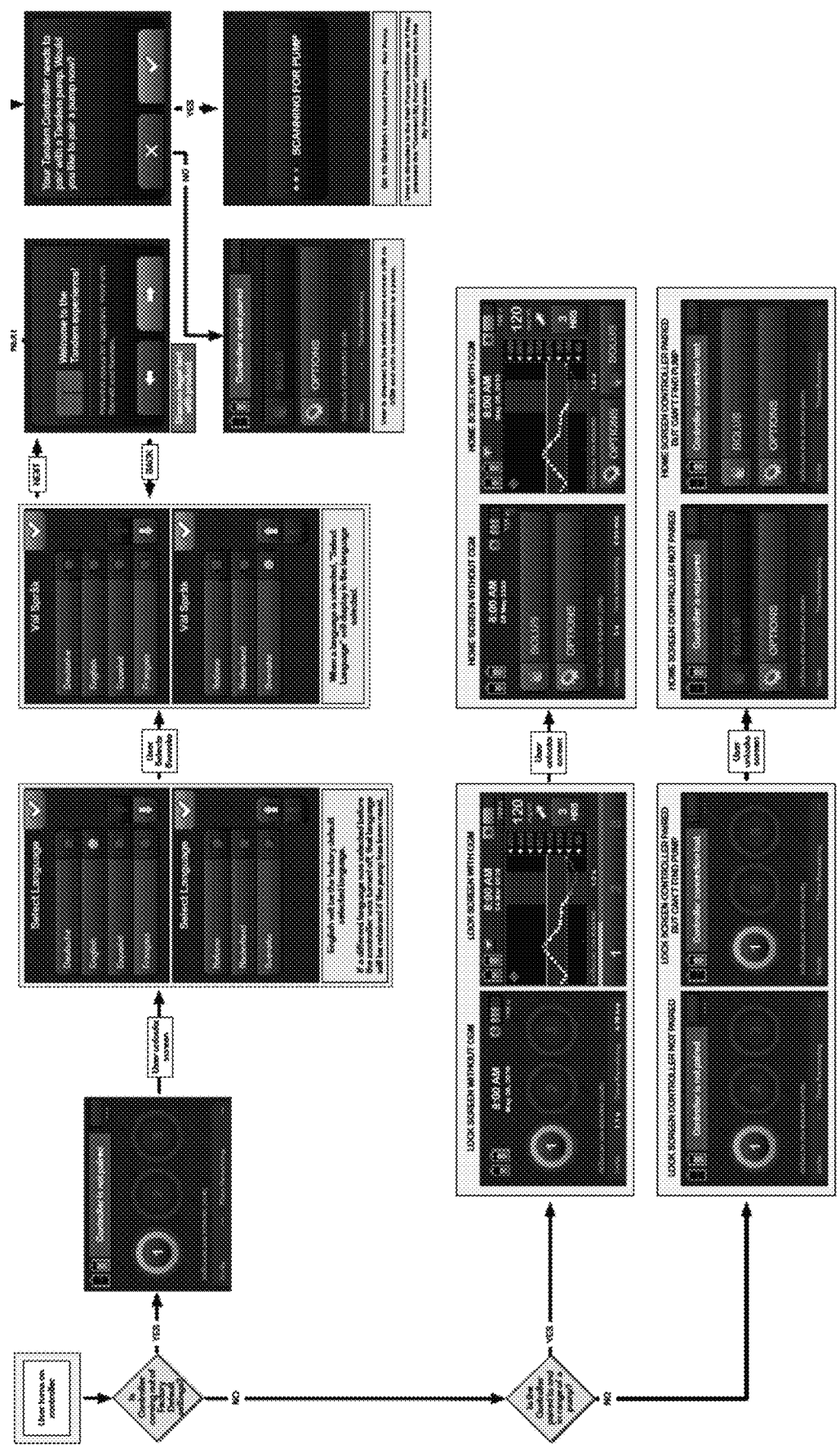
FIG. 29 depicts a workflow and various screens that can be displayed on a remote control device for an infusion pump system relating to a controller reset according to the disclosure.

FIG. 29 depicts a workflow for a procedure for when the remote control device is powered on from an off state. Initially, it is determined if the controller is being opened with factory default settings (i.e., when the controller is turned on for the first time or if the controller has been reset to factory defaults). If so, the user sets initial pump settings such as language and pairing with a pump. If the controller does not have factory default settings, it is determined whether the controller is paired with and in range of a pump. If so, the lock screen and home screen are displayed for normal operation. If the controller is not paired with and in range of the pump, the Controller connection lost banner is displayed on the lock screen and home screen.

Safety Features

Figure 30A:
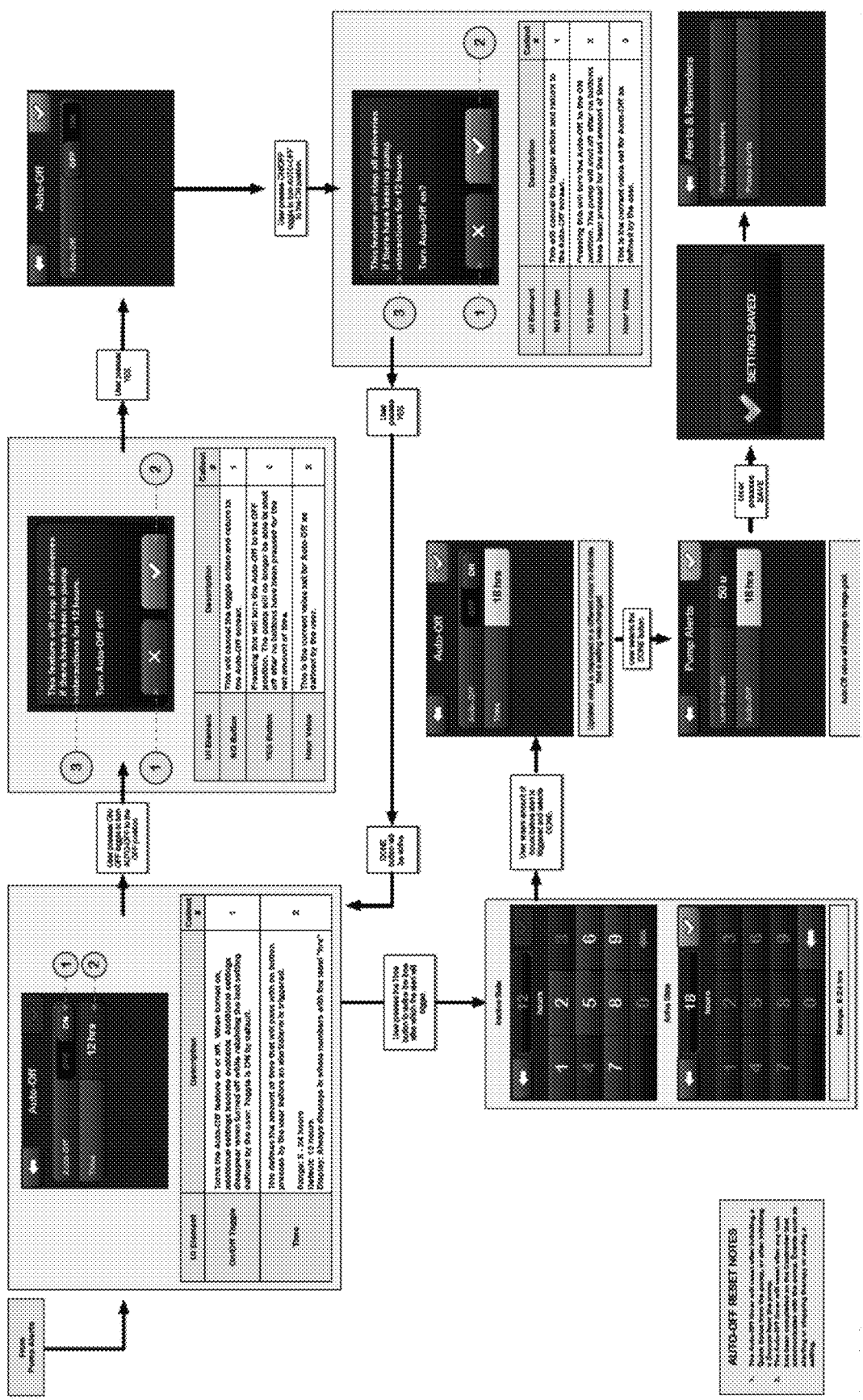
Figure 30B:
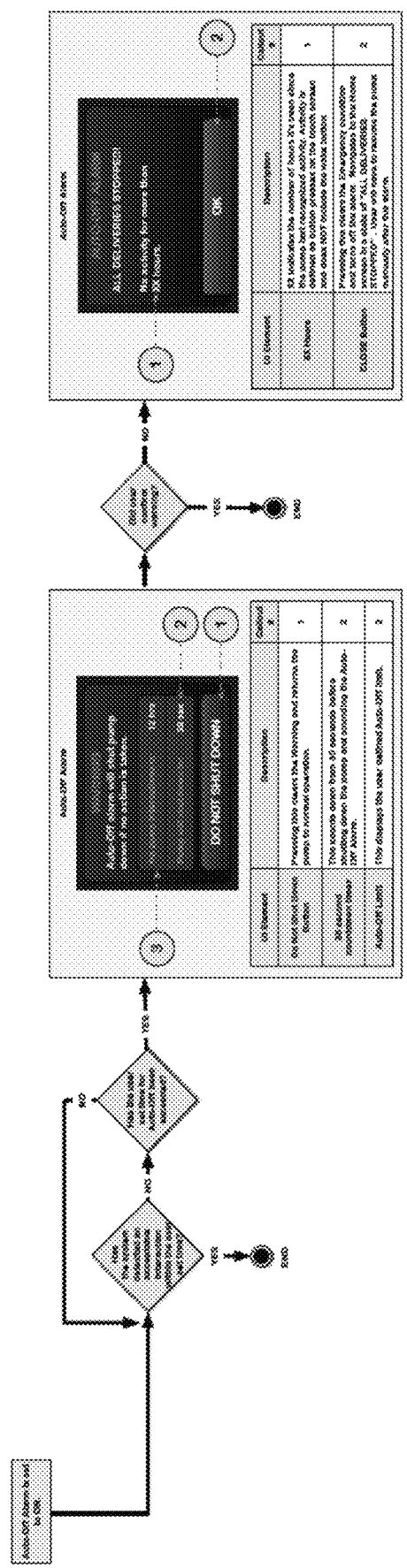

Referring to FIGS. 30A-30C, a programmable safety of the remote control is an auto-off feature. The auto-off feature can automatically turn off and stop delivering medicament with the pump when there has been no interaction with the remote controller or pump for a set period of time. This feature is provided to prevent medicament delivery in case someone is unable to interact with the controller and pump to due to extreme low glucose levels. Referring to FIG. 30A, the auto-off feature can be turned on and a time period for the feature set by accessing an Auto Off display screen from the Pump Alerts menu. If the user selects to turn the auto-off feature on, the user can enter a time period of the auto-off feature into a numeric keypad. A confirmation screen can then be presented informing the user that the feature will stop all deliveries after the set period of time and requiring a user to confirm the setting. Similarly, if the user turns the auto-off feature off, the user must confirm the setting change.

In operation, as depicted in FIG. 30B, when the auto-off feature is turned on the system continually checks to see if the user has been interacting with the controller or pump and, if not, if the programmed auto-off time has been reached since the last interaction. If the auto-off time is reached without user interaction, an Auto-Off Warning is displayed informing the user that the pump will be shut down because the auto-off time has been reached without user interaction. The user can select the Do Not Shut Down item to cancel the auto-off feature, otherwise the pump will automatically shutdown within a predetermined period of time, such as, for example, 30 seconds. When the pump is shutdown, the Auto Off Alarm indicating that the pump has been shutdown and all deliveries have been stopped. Even if the user acknowledges the alarm at this point, the user will need to manually turn the pump back on. FIG. 30C depicts a table listing the various controller and pump interactions that will reset the timer for the auto-off feature.

Figure 31:
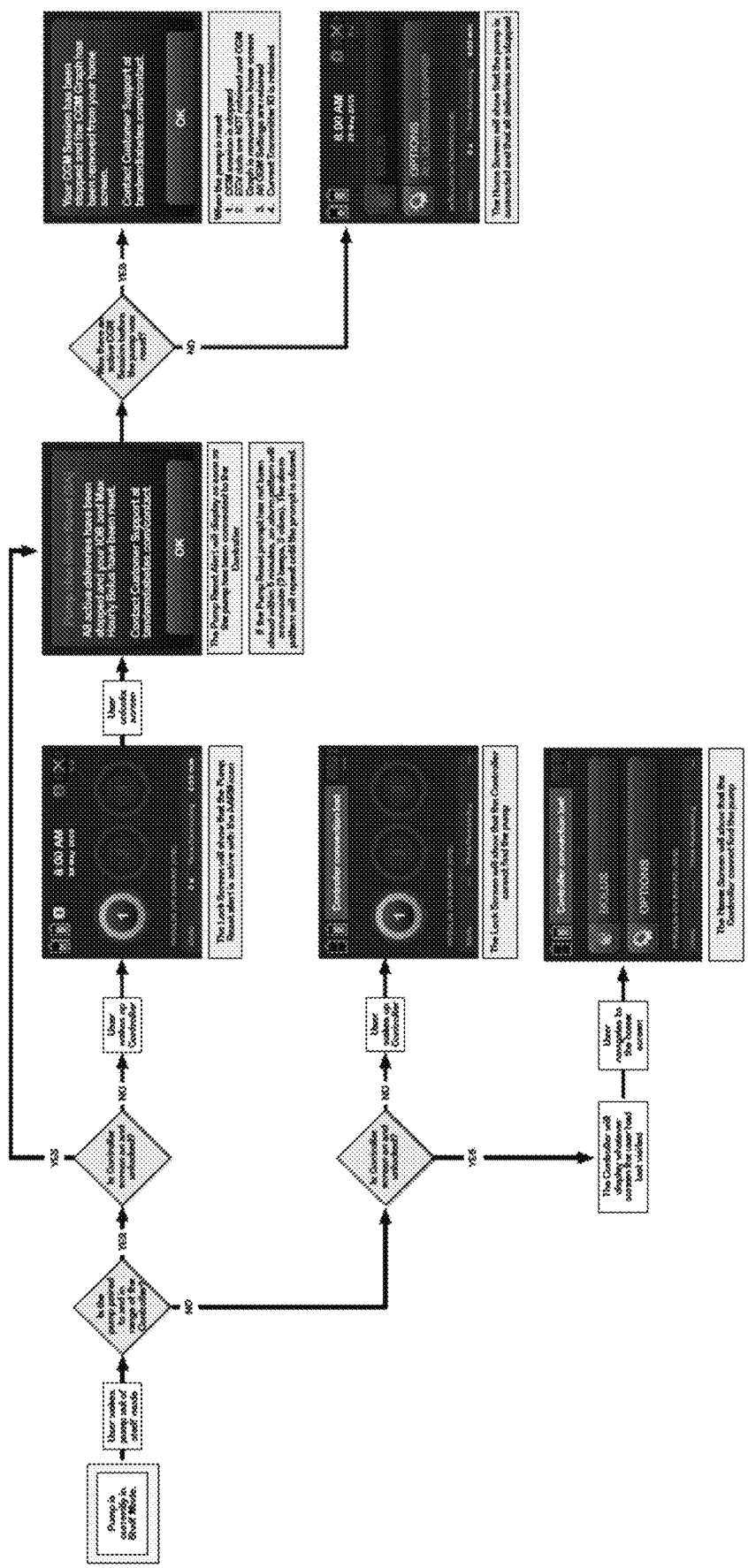
FIG. 31 depicts a workflow and various screens that can be displayed on a remote control device for an infusion pump system relating to a pump reset according to the disclosure.

Referring now to FIG. 31, if the controller detects that one of the pump processors has been reset, a Pump Reset Alert can be displayed to notify the user in case of an unexpected reset or an intentional reset not acknowledged by the user. One example when this may occur is when the pump has been rebooted after a software update, but the user forgot to resume pumping after the update. When the pump is activated from shelf mode, first it is determined if the pump is paired with and in range of the controller. If not, the Controller connection lost banner is displayed. If the pump is paired and in range, the controller will display the Pump Has Been Reset Alert, either immediately or after unlocking the screen, informing the user that all active deliveries have been stopped and the IOB and max hourly basal reset, and instructing the user to contact customer support. If there was an active CGM session when the pump was reset, the user is informed that the CGM session has been stopped and further instructed to contact customer support. The home screen will then be updated to indicate that all deliveries have been stopped and the bolus menu item disabled.

Figure 32A:
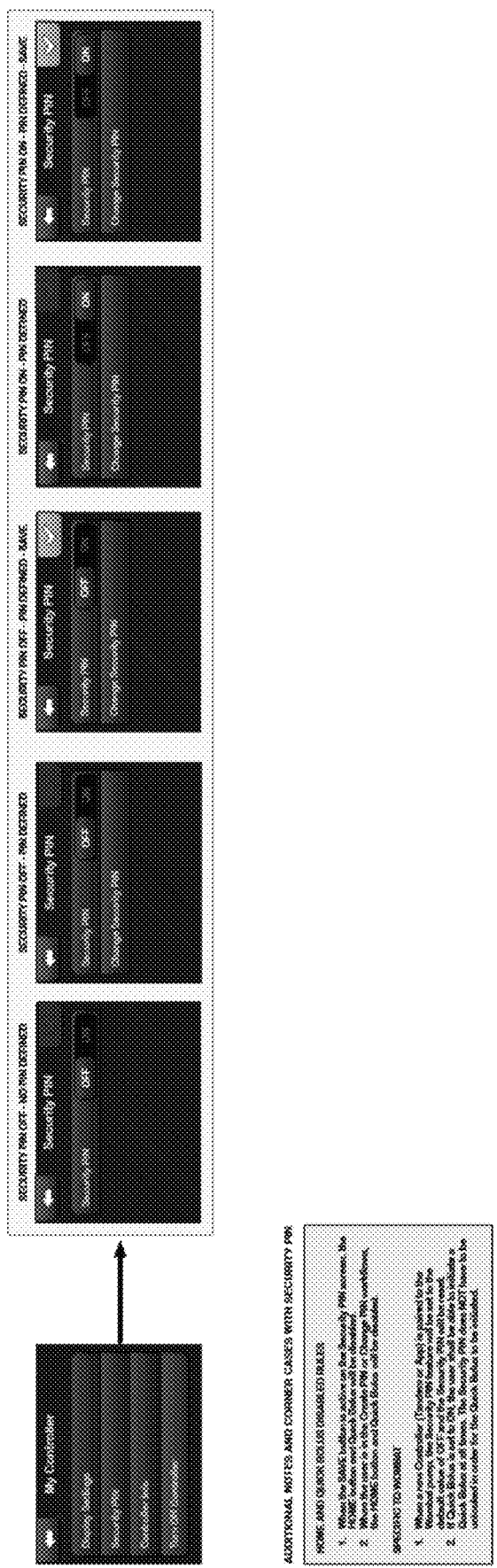
FIGS. 32A-32C depict a workflow and various screens that can be displayed on a remote control device for an infusion pump system relating to a security PIN feature according to the disclosure.
Figure 32B:
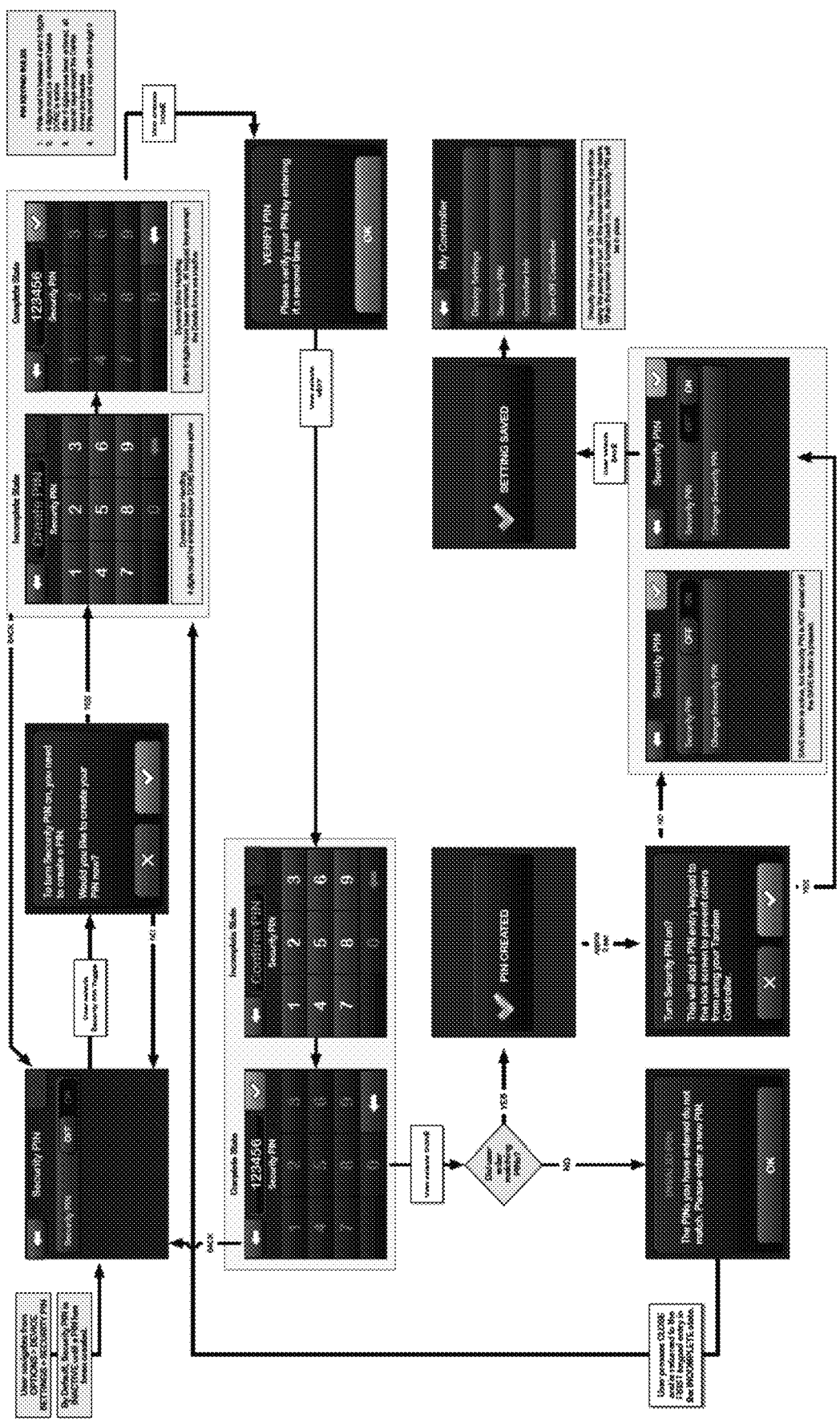
Figure 32C:
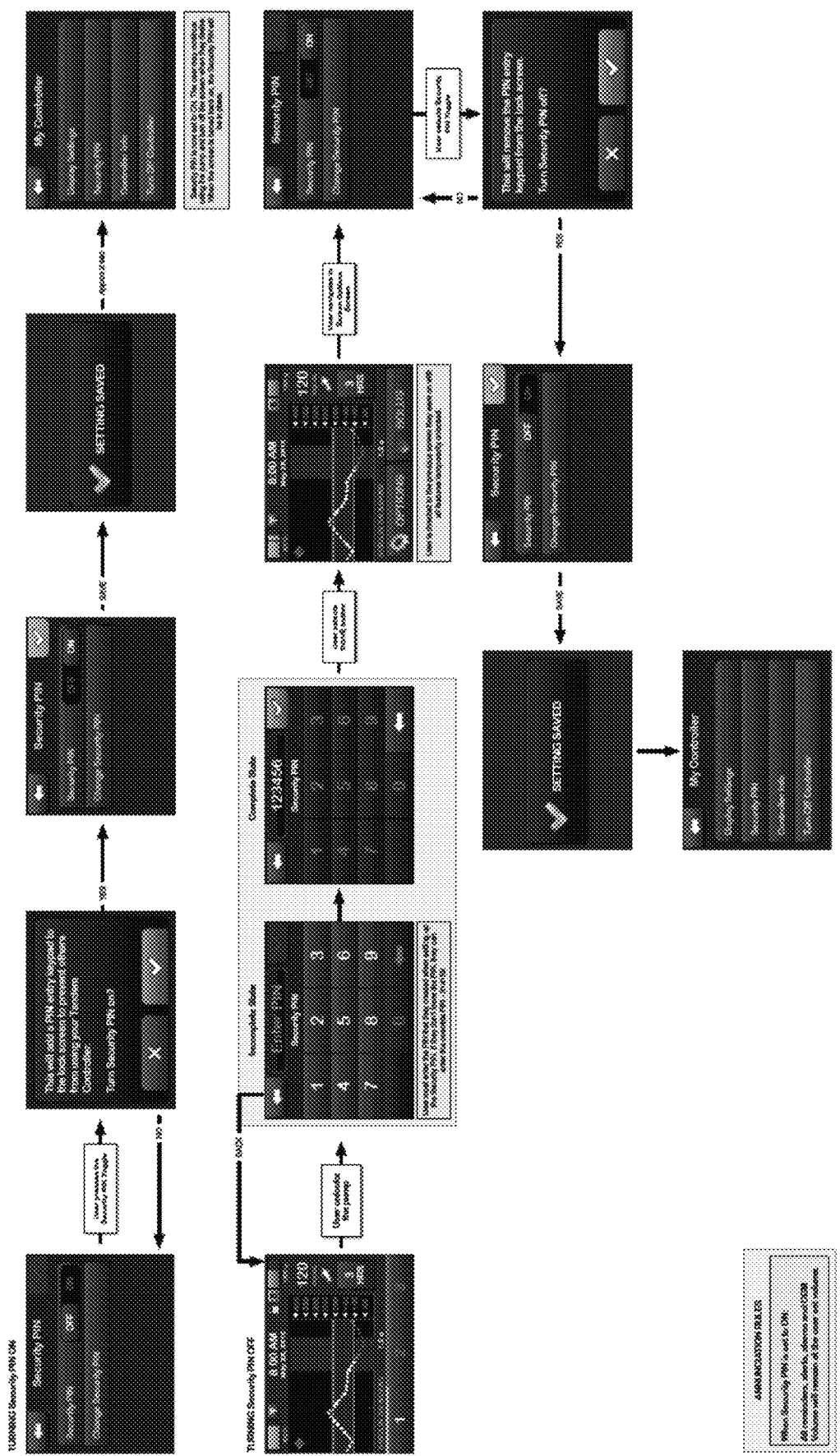

Referring now to FIGS. 32A-32C, the remote control device can include a security PIN feature to enhance device security by preventing others from using the controller. FIG. 32A depicts that the security PIN can be turned off or on from a Security PIN menu accessible from the My Controller menu. Referring to FIG. 32B, if the user selects to turn the security PIN on, a confirmation screen is displayed and if the user confirms a keypad is presented for the user to enter the desired security PIN. In the depicted embodiment, the PIN is a numeric sequence between four and six numbers long. The user is then requested to enter the PIN a second time to confirm the number. If the PIN numbers do not match, an error occurs and the user must restart the PIN creation process. If the PIN numbers do match, the PIN is created and the user is asked to confirm creation of the PIN, after which the PIN number and ON setting are now saved. The user will now be required to enter the PIN in order to access controller functions. As can be seen in FIG. 32C, once a PIN is stored, the security PIN setting can be turned off and on without having to reset the PIN number itself.

Status and History

Figure 33:
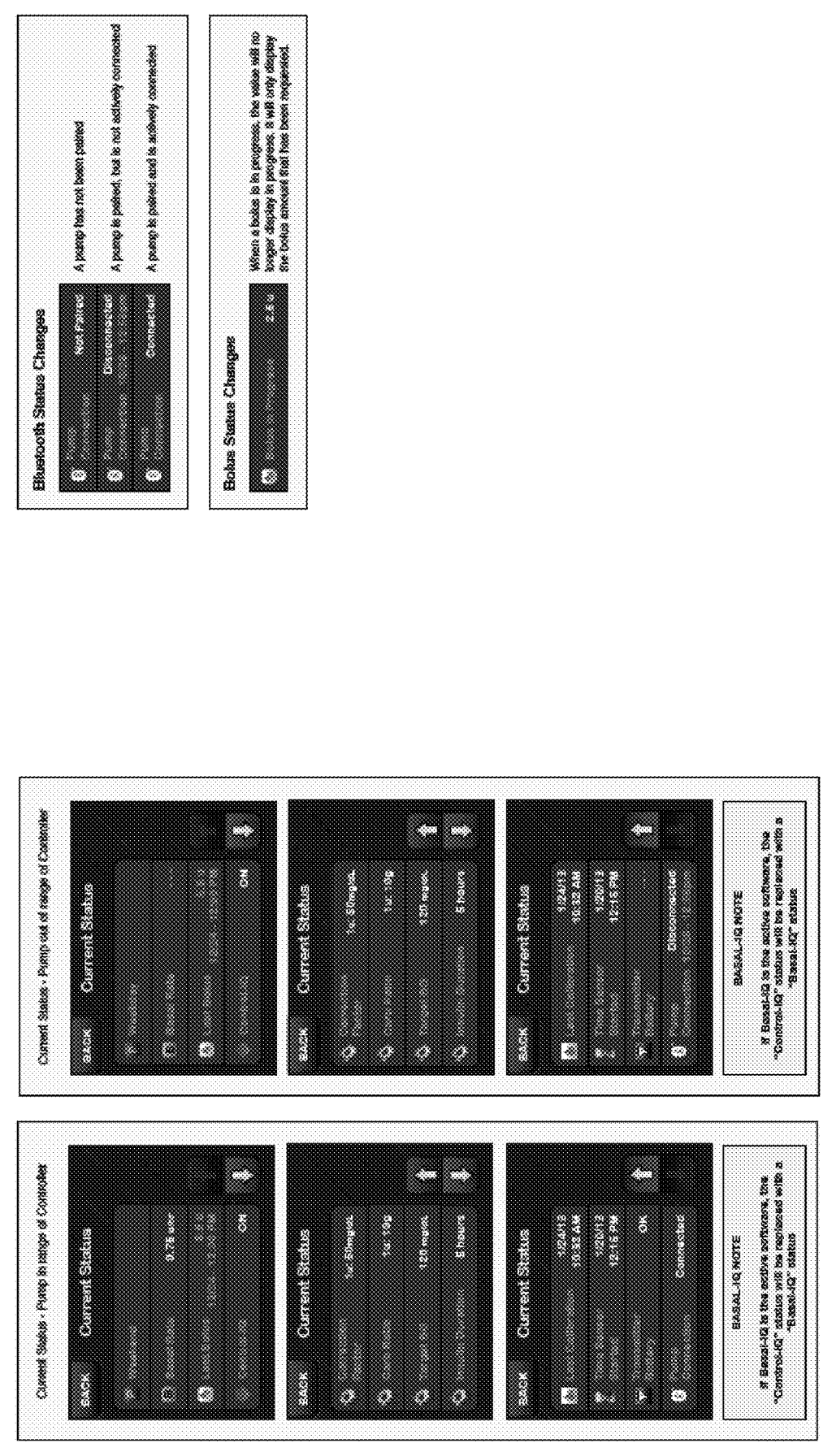

A user can review current status of various aspects of the system by accessing a Current Status screen as depicted in FIG. 33. Current status items that can be viewed include, for example, a current basal rate setting, a most recent bolus amount delivered, whether an algorithm that automatically determines medicament delivery is on or off, the currently programmed correction factor, carb ratio, target BG and insulin duration values, the last time the CGM sensor was calibrated, when it was last started and the transmitter battery status, and the status of the connection between the pump and the controller.

Figure 34:
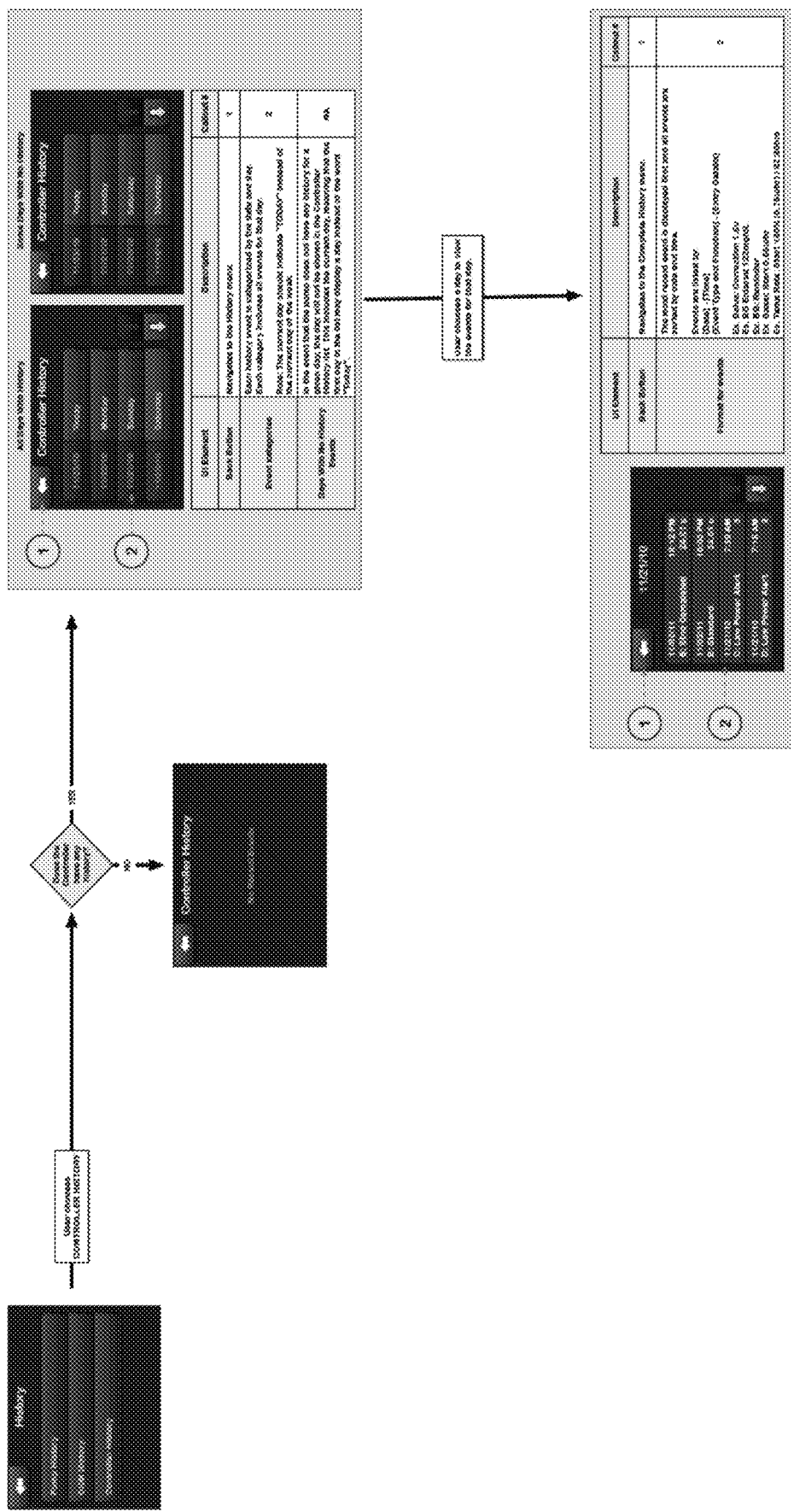
FIG. 34 depicts various screens that can be displayed on a remote control device for an infusion pump system for accessing Bluetooth settings according to the disclosure.

The remote control device can be used to access pump history, CGM history and controller history. The controller history can be accessed as depicted in FIG. 34 from the History Menu. If the controller does not have any recent history to display, a message indicating that there is no recent history can be displayed. If there is recent history, the history can first be displayed by day, with only days having relevant history being displayed. If the user selects a day, individual events that occurred on that day can be displayed by time of day and listing the time of event and relevant parameters.

The examples given above with respect to various colors, illumination patterns and combinations, etc. are illustrative only and it should be understood that different information can be conveyed by varying the output of indicator lights 174 in any number of ways.

Although the pump system described herein is described as a user-wearable pump system that has no display or user interface and is primarily controlled by a remote device, it should be understood that aspects of the present disclosure can be incorporated into other types of infusion pumps. For example, full-featured user-wearable infusion pumps having display and input capabilities, such as a touchscreen display on the pump housing, one example of which is disclosed in U.S. Pat. No. 8,287,495, which is hereby incorporated by reference herein, can incorporate aspects of the present disclosure.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; and 10,569,016. commonly owned U.S. Patent Publication Nos. 2009/0287180; 2012/0123230; 2013/0053816; 2014/0276423; 2014/0276569; 2014/0276570; 2018/0021514; 2018/0071454; 2019/0240398; 2019/0307952; and 2019/0365997 and commonly owned U.S. patent application Ser. Nos. 16/507,146; 16/598,343; 16/725,278; 16/725,337; and 16/793,662 Although the embodiments herein have been specifically described with respect to an ambulatory infusion pump, the inventions disclosed herein could be employed with any other type of programmable medical device capable of receiving and executing remote commands. Such devices include, for example, implantable pumps, defibrillators, spinal cord stimulation systems, etc. Embodiments could further include non-medical applications.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of operating a user-wearable infusion pump having no display screen with a remote control device, comprising:
   presenting a plurality of menus on a display screen of the remote control device, the plurality of menus including menu items enabling programming of operating parameters for the user-wearable infusion pump;
   detecting a current status of the infusion pump;
   providing an indication of the current status of the infusion pump with a light pattern provided by one or more indicator lights disposed on the infusion pump, the light pattern of the current status being selected from a plurality of different light patterns stored in memory each indicating a different type of pump status;
   presenting information relating to the current status of the infusion pump indicated by the light pattern of the current status on the display screen of the remote control device.

2. The method of claim 1, wherein the light pattern of the current status of the infusion pump corresponds to an alarm and the information presented on the display screen of the remote control device notifies the user of an actual or potential stopping of medicament delivery with the infusion pump.

3. The method of claim 1, wherein the light pattern of the current status of the infusion pump corresponds to an alert and the information presented on the display screen of the remote control device notifies the user of a safety condition relating to use of the infusion pump.

4. The method of claim 1, wherein the light pattern of the current status of the infusion pump corresponds to a malfunction and the information presented on the display screen of the remote control device notifies the user of an error stopping delivery of medicament.

5. The method of claim 1, wherein the light pattern of the current status of the infusion pump corresponds to a reminder and the information presented on the display screen of the remote control device notifies the user of an optional notification set by the user.

6. The method of claim 1, wherein the light pattern of the current status of the infusion pump relates to a current delivery of medicament with the infusion pump and the information presented on the display screen includes a status of the current delivery of medicament.

7. The method of claim 1, wherein the information presented on the display screen includes textual information.

8. The method of claim 1, wherein the information presented on the display screen includes graphical information.

9. The method of claim 1, wherein the light pattern varies one or more of a color of the one or more lights, a frequency of illumination of the one or more lights, a duration of illumination of the one or more lights and an intensity of illumination of the one or more lights.

10. The method of claim 1, further comprising receiving input at the infusion pump with an input button disposed on the infusion pump.

11. A system for operating an infusion pump with a remote control device, comprising:
- a user-wearable infusion pump including one or more indicator lights and no display screen, wherein the one or more indicator lights are configured to provide an indication of a current status of the infusion pump by displaying a light pattern corresponding to the current status selected from a plurality of different light patterns each indicating a different type of pump status; and
- a remote control device including a display screen configured to present a plurality of menus including menu items enabling programming of operating parameters for the infusion pump to remotely control the user-wearable infusion pump, wherein the remote control device is configured to display on the display screen information relating to the current status of the infusion pump indicated by the light pattern displayed by the one or more indicator lights of the infusion pump.

12. The system of claim 11, wherein the light pattern corresponding to the current status of the infusion pump corresponds to an alarm and the information presented on the display screen of the remote control device notifies the user of an actual or potential stopping of medicament delivery with the infusion pump.

13. The system of claim 11, wherein the light pattern corresponding to the current status of the infusion pump corresponds to an alert and the information presented on the display screen of the remote control device notifies the user of a safety condition relating to use of the infusion pump.

14. The system of claim 11, wherein the light pattern corresponding to the current status of the infusion pump corresponds to a malfunction and the information presented on the display screen of the remote control device notifies the user of an error stopping delivery of medicament.

15. The system of claim 11, wherein the light pattern corresponding to the current status of the infusion pump corresponds to a reminder and the information presented on the display screen of the remote control device notifies the user of an optional notification set by the user.

16. The system of claim 11, wherein the light pattern corresponding to the current status of the infusion pump relates to a current delivery of medicament with the infusion pump and the information presented on the display screen includes a status of the current delivery of medicament.

17. The system of claim 11, wherein the information presented on the display screen includes textual information.

18. The system of claim 11, wherein the information presented on the display screen includes graphical information.

19. The system of claim 11, wherein the light pattern varies one or more of a color of the one or more lights, a frequency of illumination of the one or more lights, a duration of illumination of the one or more lights and an intensity of illumination of the one or more lights.

20. The method of claim 1, wherein the infusion pump includes an input button.

\* \* \* \* \*